(12) United States Patent
Levine et al.

(10) Patent No.: US 7,756,722 B2
(45) Date of Patent: Jul. 13, 2010

(54) CLINICAL MANAGEMENT SYSTEM FROM CHRONIC ILLNESSES USING TELECOMMUNICATION

(75) Inventors: Betty A. Levine, Bethesda, MD (US); Stephen C. Clement, McLean, VA (US); Seong Ki Mun, McLean, VA (US); Adil Alaoui, Fairfax Station, VA (US); Tang Ming-Jye Hu, Springfield, VA (US)

(73) Assignee: Georgetown University, Washington, DC (US)

( * ) Notice: Subject to any disclaimer, the term of this patent is extended or adjusted under 35 U.S.C. 154(b) by 1452 days.

(21) Appl. No.: 09/967,923

(22) Filed: Oct. 2, 2001

(65) Prior Publication Data

US 2003/0011646 A1 Jan. 16, 2003

Related U.S. Application Data

(60) Provisional application No. 60/265,306, filed on Feb. 1, 2001.

(51) Int. Cl.
*G06Q 10/00* (2006.01)

(52) U.S. Cl. .............................. 705/2; 705/3; 600/300; 715/866; 345/952

(58) Field of Classification Search .................. 705/2–3; 600/300
See application file for complete search history.

(56) References Cited

U.S. PATENT DOCUMENTS

| | | | | |
|---|---|---|---|---|
| 5,833,623 A * | 11/1998 | Mann et al. | ................. | 600/523 |
| 5,879,163 A | 3/1999 | Brown et al. | | |
| 6,032,119 A | 2/2000 | Brown et al. | | |
| 6,039,688 A | 3/2000 | Douglas et al. | | |
| 6,151,581 A * | 11/2000 | Kraftson et al. | ................ | 705/3 |
| 6,234,964 B1 * | 5/2001 | Iliff | ............................ | 600/300 |
| 6,416,471 B1 * | 7/2002 | Kumar et al. | ............... | 600/300 |
| 6,850,889 B1 * | 2/2005 | Zayas, Jr. | ....................... | 705/3 |
| 2001/0039503 A1 * | 11/2001 | Chan et al. | ..................... | 705/2 |
| 2006/0161459 A9 * | 7/2006 | Rosenfeld et al. | .............. | 705/3 |

OTHER PUBLICATIONS

"DCCT and EDIC: The Diabetes Control and Complications Trial and Follow-Up Study," National Diabetes Information Clearinghouse, NIH Publication No. 08-3874, May 2008, pp. 1-6.

(Continued)

*Primary Examiner*—Vanel Frenel
(74) *Attorney, Agent, or Firm*—Blank Rome LLP

(57) ABSTRACT

Patients with chronic illnesses resist using conventional automated healthcare management systems to supply necessary clinical data because such systems feel impersonal, preferring to actually visit a clinic where the patient interacts with various healthcare practitioners. In this invention, the patient interacts with a clinical management system via a series of initial GUI screens that replicate the experience of actually visiting the clinic. Additional screens allow the patient to submit clinical information, to communicate with that patient's healthcare practitioner and other healthcare practitioners, to access management information that aids the patient in managing that patient's chronic illness, and to access educational information regarding that chronic illness. The clinical management system may be used to manage a plurality of different chronic illnesses while providing a consistent look and feel to the screens. At least one appearance characteristic can be altered to indicate the particular chronic illness to which a screen applies.

36 Claims, 96 Drawing Sheets

OTHER PUBLICATIONS

"Diabetes Control and Complications Trial (DCCT)," Principal Investigator: John M. Lachin, Sc.D., The George Washington University Biostatistics Center, 2008, pp. 1-4.

LifeChart.com: Monitoring Diabetes: The LifeChart Way [online]. LifeChart [retrieved Oct. 9, 2002]. Retrieved from the Internet: <URL: http://web.archive.org/web/20010418055211/www.lifechart.com/webpage_templates/te . . . >. (3 pps).

LifeChart.com: Managing Diabetes: [online]. [retrieved Oct. 9, 2002]. Retrieved from the Internet: <URL: http://web.archive.org/web/200012190207001/www.lifechart.com/webpage_templates/te . . . >. (1 pps).

Diabetes: DiabetesWell—The Program: [online]. [retrieved Oct. 9, 2002]. Retrieved from the Internet: <URL: http://web.archive.org/web/20001202164100/www.diabeteswell.com/program/index.asp>. 3 pps.

Diabetes: DiabetesWell—Personal Web Page: [online]. [retrieved Oct. 9, 2002]. Retrieved from the Internet: <URL: http://web.archive.org/web/20001202175900/www.diabeteswell.com/program/personal>. 2 pps.

* cited by examiner

Insulin prescription: 1714

Date prescribed: 4/18/00 7:04:59 AM

| Insulin | | Pre-Breakfast | Pre-Lunch | Pre-Dinner | Bed Time |
|---|---|---|---|---|---|
| Long Acting | nph | 20 | | | 20 |
| Short Acting | Lispro | 10 | 5 | 8 | |

Oral medication: 1724

Date prescribed: 4/20/00 10:54:57 PM

| Medication | | Dose Selection (mg) | # of Tabs for each dose | Frequency |
|---|---|---|---|---|
| Drugs which decrease glucose production by the liver | Glucophage | 500 | 2 | AM and PM |

Other medication:

Last modified: 4/12/00 3:58:29 PM

| Medication | Date | | Dosage | Frequency | Purpose of medicine |
|---|---|---|---|---|---|
| | Start | Stop | | | |
| Claritin | 2/1/00 | 2/1/01 | | 1x | Allergy |

Brown_Charlie 10/2/50

2100

2120

| Date | Avg BG | SD | # Hypos | % in Target | Avg # Readings | # of days | Patient Comments | Physician Comments |
|---|---|---|---|---|---|---|---|---|
| 7/18/98 | 131 | 71.43 | 9 | 63 | 3.5 | 14 | On Vacation and had stressful week at work beforehand | Try to stay on your meal plan, even while on vacation |
| 7/5/98 | 210 | 84.6 | 15 | 45 | 3 | 21 | Nothing unusual overall, good week | Good Job, no change needed |
| 6/14/98 | 145 | 60.1 | 4 | 69 | 4 | 9 | Nothing unusual | Good work. |
| 6/6/98 | 115 | 57 | 5 | 62 | 3 | 7 | | |

Submit  Reset messages  clinical data  medication  contact  logout

Figure 27

Aksys Reports First Patients Dialyze at Home on PHD(TM) System

LINCOLNSHIRE, Ill., March 14 /PRNewswire/ via NewsEdge Corporation

Aksys, Ltd. (Nasdaq: AKSY), a pioneer in innovative dialysis systems, announced today that, for the first time, patients are dialyzing at home using the Personal Hemodialysis (PHD(TM)) System. The first three of the twenty-four patients participating in the Company's clinical trial have entered the third and final stage of the study, during which they will dialyze at home for eight weeks.

Patients enrolled in the three-stage study will participate for a minimum of twenty weeks. During the first stage, baseline clinical information on daily hemodialysis is established. In the second stage, patients convert to the PHD System in the clinic where they are trained to operate the unit. During the third stage, patients dialyze at home on the PHD System.

"This is a significant milestone for the Company," stated William Dow, President and CEO. "We have moved one giant step closer to providing a platform that will make the convenience of home dialysis and the clinical benefits of daily dialysis available to end stage renal disease patients worldwide. The hard work of our employees is starting to make our Company's vision a reality."

The Company currently has patients being dialyzed on the PHD System at all three of its clinical sites, which has resulted in nearly 200 treatments being completed on the PHD System to date. Two of the clinical sites have patients dialyzing at home. "The patients in the clinical study are reacting very positively to daily hemodialysis - they feel and look better," stated Dow. "We are pleased with the progress of the clinical trial and remain on track to complete the study by the end of the third quarter."

Figure 33

Dummy Patient 3/23/99                                          3735

Medications                                                 3710

| Medication | Dose | Unit | Frequency | Route | Date Start | Date Stop | Instruction |
|---|---|---|---|---|---|---|---|
| Tylenol | 325 | 2 | 2 | PO | 3/23/00 | 3/29/01 | Keep taking the Tylenol see DR before discontinue |

Other Medications                                           3720

| Medication | Date Start - Stop | Dosage | Frequency | Purpose of medicine |
|---|---|---|---|---|
| PediCare | 6/10/00 - 6/24/00 | 1 ml | 3x | |

Clinic Numbers: 202-342-1127 or 202-333-5211

ALWAYS REMEMBER: If you touch any of your equipment or if you touch your hair or stretch your nose before you've begun your exchange, you will not be working in a sterile environment. You have to wash your hands all over again. If you touch any of these after you've begun your exchange-You have to STOP, throw away your exchange equipment and start over again.

How to do a SAFE EXCHANGE

Checklist for a SAFE Exchange:

Your Unopened Dialysate Bag is

Your Area is

3 Steps to a SAFE Exchange

| DRAIN | FILL | DWELL |
|---|---|---|

| How long does a PD Exchange take? | About 30 minutes for each exchange. The Dialysate should stay in the belly for 4-6 hours |
|---|---|
| Is it working? How do I know? | Talk about lab values and then go to the lab pages |

Always Remember:
If you touch, cough, or sneeze on sterile equipment, you HAVE to throw away the equipment and start all over again.

Problem List

| Cloudy Bag | Unclear but not Cloudy Bag | Leaking Equipment | Cramps | Exit Site Infection |
|---|---|---|---|---|

| Take a look in the Daily Life Section for details on foods to eat - or Not! - to avoid some of these problems and feel good | And Don't forget! Call your Clinic if you need help |
|---|---|

Return to Main Education Page

Figure 41B

Pager: 1-888-600-6844
Clinic Numbers: 202-842-3127 or 202-333-5211

How to do a SAFE EXCHANGE

Checklist for a SAFE Exchange:

3 Steps to a SAFE Exchange

- Your Unopened Dialysate Bag is
- Your Unopened Dialysate Bag is — 4310
- not leaking
- correct size and strength
- current expiration date
- clear not brown
- warmed (if wanted) in sunlight or low setting on heating pad
- NOT warmed in water, on stove, or in microwave

| How long does a PD Exchange take? | About 30 minutes for each exchange. The Dialysate should stay in the belly for 4-6 hours |
| --- | --- |
| Is it working? How do I know? | Talk about lab values and then go to the lab pages |

Always Remember
If you touch, cough, or sneeze on <u>sterile</u> equipment, you HAVE to throw away the equipment and start all over again.

Problem List

Figure 43

How to do a SAFE EXCHANGE

Pager: 1-888-600-6844
Clinic Numbers: 202-842-3127 or 202-333-5211

Checklist for a SAFE Exchange:

Your Unopened Dialysate Bag is

3 Steps to a SAFE Exchange

Your Area is
Your Area is — 4410
clean
well lit
dry
away from drafts, fans, and open windows
quiet
away from pets

DWELL

| How long does a PD Exchange take? | ...utes for each exchange. The Dialysate should stay in the belly for 4-6 hours |
|---|---|
| Is it working? How do I know? | Talk about lab values and then go to the lab pages |

Always Remember
If you touch, cough, or sneeze on sterile equipment, you HAVE to throw away the equipment and start all over again.

Problem List

Figure 44

Exchange - Step 3
DWELL

- Let the fluid stay inside your belly for 4-6 hours
- Then begin your next exchange: Drain, Fill, Dwell again
- Always flush drained fluid down the toilet (Add bleach to the used dialysate if you are HIV positive) and put transfer sets and empty bags in garbage.

AND wash your hands

Click here to close window

FLUIDS - Too Much or Too Little

| Too Much Fluid | Too Little Fluid |
|---|---|
| Signs of it<br>• Increased Weight<br>• Puffy Skin around eyes, ankles & fingers<br>• Higher than usual blood pressure<br>• Shortness of Breath | Signs of it<br>• Dizziness<br>• lower than usual blood pressure<br>• lower than usual body weight |
| What To Do<br>• Take control of how much you eat and drink<br>• Weigh yourself daily<br>• Use stronger solution for a few exchanges<br>• Drink Less until you start feeling better | What to Do<br>• Drink more liquids<br>• Use fewer high solution bags such as 4.25%<br>• Use 1.5% solution bags until you feel better |

Return to Top

What you eat! See what foods give you:

| Protein | Phosphate | Potassium | Sodium | Carbohydrates |
|---|---|---|---|---|
| lean meat | milk<br>ice-cream<br>nuts | oranges<br>grapefruit<br>Bananas<br>cantaloupe<br>broccoli | bacon<br>Ham<br>hot dogs | sugars from sweet foods |

Figure 47B

What you eat! See what foods give you:

| Protein | Phosphate | Potassium | Sodium | Carbohydrates |
|---|---|---|---|---|
| lean meat<br>cheese<br>fish<br>eggs<br>chicken | milk<br>ice-cream<br>nuts<br>cola<br>chocolate<br>beer<br>peanutbutter<br>oatmeal<br>cheese | oranges<br>grapefruit<br>Bananas<br>cantaloupe<br>broccoli<br>brussel<br>sprouts<br>spinach<br>squash<br>tomatoes<br>yams<br>breads<br>cereals | bacon<br>Ham<br>hot dogs<br>can soups<br>can vegies<br>salty chips<br>salt<br>chinese-<br>food | sugars from<br>sweet foods<br>and from<br>starches like<br>bread and<br>cereal |

Return to Top

Weight - Gain or Loss

| Weight Gain | Weight Loss |
|---|---|
| • Weigh yourself everyday<br>• More than 4 pounds in one day, you may have too much fluid weight<br>• If your skin is puffy around your eyes, ankles and fingers you should change your diet: avoid salty foods<br>• See Too Much Fluid above | • Weigh yourself everyday<br>• More than 4 pound in one day, you are probably dehydrated<br>• See Too Little Fluid above |

Return to Top

Figure 47C

These are Special medicines for special needs when you are on PD.

| | |
|---|---|
| Insulin | is used by many diabetics to lower their blood sugar level. Diabetics on PD can inject insulin into the dialysate bag. |
| Heparin | is an anti-clotting drug. It is used when you have fibers (called fibrin) in your drained solution and your catheter is blocked. This is a liquid that will be injected into your dialysis solution bag when you need to use it. (Your nurse will tell you when that time is!) |
| Antibiotics | Fight infections. If you get peritonitis or an exit site infection, your doctor will prescribe antibiotics. These can be taken either as pills or as a liquid that will be injected into your dialysis bag. |
| Blood Pressure Pills | Also called hypertensives. Because your kidneys can no longer hel control your blood pressure, you may need blood pressure pills to help. These should lower your blood pressure so there will be less strain on your heart. |

Return to Top

Eating Out - Here are some tips

This month it's Italian: Salad (no tomatoes!), Italian bread with butter, Veal Marsala
Remember: You want to avoid tomato sauce. This will work!

There's a new brochure, too, called "Dining Out with Confidence: A guide for Renal Patients" from the National Kidney Foundation. It includes great tips for renal patients on ordering from menus at French, Japanese, and other ethnic restaurants. To order your copy of "Dining out with Confidence" call the founation at (212)889-2210

Return to top

Tips for Great exercise - Try Them!

Figure 47F

Clinic Numbers: 202-849-3177 or 202-233-5211

Eating Out – Here are some tips

This month it's Italian: Salad (no tomatoes!), Italian bread with butter, Veal Marsala
Remember: You want to avoid tomato sauce. This will work!

There's a new brochure, too, called "Dining Out with Confidence: A guide for Renal Patients" from the National Kidney Foundation. It includes great tips for renal patients on ordering from menus at French, Japanese, and other ethnic restaurants. To order your copy of "Dining out with Confidence" call the founation at (212)889-2210

Return to Top

Tips for Great exercise – Try Them!

It's safe, it can improve your blood pressure and cholesterol levels, and you'll have more energy to do other things.

Take a stationary bike ride ... or just take a walk

Return to Top

Travel Tips

Arrange for your dialysis solutions to be delivered to your destination, weeks before your arrival. Ask the social worker at the clinic to help you.

Be sure to ask your travel agent, airline, or tour guide for a low sodium diet during your travel times and when ordering at hotels and restaraunts If you like travel, consider ordering the magazine "For Patients Only" at (818)704-5555 which is geared only to kidney patients and their travel needs and plans.

Return to Top

Socializing – Some activities for you

Figure 47G to eat

Order from Amazon.com (www.amazon.com), Under Books, type in the title

Free newsletter: Renal Flash, is produced by the American Association of Kidney Patients, transmitted by email. Go to www.aakp.org/renal.html to subscribe.

News Alert:

Published in February: "Noni", a type of fruit juice sold in health food stores, can be a hidden source of potassium and a hazard for paatients with kidney disease.

Fun News:

"Pez helps fight kidney disease"--On March 31, 2000, the 3rd Annual Pez Convention was held in Los Angeles to raise $5000 for kidney research by auctioning off rare Pez dispensers, which have come in 500 different varieties. Over 1500 visitors were expected to join the auction.

"TINA" the hemodialyzer went to Hollywood, to make a guest appearance on the TV show ER, March 16, 2000. Why TINA? According to the show's decision makers, "As for as we are concerned TINA is the best looking dialysis machine on the market." Who wouldn't bne impressed?

Web Sites to Check Out

Did you know that we found over 14,000 Web Sites about dialysis and kidney disease as we looked to find you other information you may need? We've been to many of them and selected 3 sites as useful for you:

www.coloradohealthnet.org/dialysis/dialmain.html - The Kidney Disease and DIalysis Center has section on news in kidney dialysis and treatment, and details you can follow on what your lab reports mean.

www.renalweb.com - At RenalWeb you can find current news of interest, recipes, and discussion groups that are moderated by nurses and other professionals www.kidneydirections.com - At KidneyDirections you will find basic information about kidney disease, a comprehensive presentation of treatment choices, and many links to further reading and on-line support.

If you also have Diabetes, www.diabetes.org - The American Diabetes Association's site is excellant for home page news articles on stress and diabetes, diabetes drugs in the news, and even take a trip to the virtual grocery store.

Return to Top

Return to Main Education Page

Figure 47I

MyKidneyTeam
DAILY ROUTINES

Fluids, Food, Medication, Fun -- The Usual Day!

Fluids
What you eat          Here are some
Your weight           Tips          4810
Blood Pressure
Medications Eating Out
Exercise
Travel
Socializing
Learn More FLUIDS - Too Much or Too Little

| Too Much Fluid | Too Little Fluid |

Figure 48

Date prescribed: 4/20/00 10:54:57 PM — 5410

| Medication | | Dose Selection (mg) | # of Tabs for each dose | Frequency |
|---|---|---|---|---|
| Drugs which enhance insulin secretion | Glipizide (generic) | | | |
| | Glucotrol XL | | | AM |
| | Glyburide (generic) | | | |
| | Micronase | | | |
| | Glynase | | | |
| | Diabeta | | | |
| | Amaryl | | | AM |
| | Prandin | | 1 | Pre meals (Three times a day) |
| Drug which decrease glucose production by the liver | Glucophage | 500 | 2 | AM and PM |
| Drugs which slow the absorption of sugars | Precose | | 1 | Pre meals (Three times a day) |
| | Glyset | | 1 | Pre meals (Three times a day) |
| Glitazonas | Avandia | | 1 | AM |
| | Actose | | 1 | AM |

Update  Reset

Figure 54

| Date | Avg BG | SD | # Hypos | % in Target | Avg # Readings | # of days | Patient Comments | Physician Comments |
|---|---|---|---|---|---|---|---|---|
| 7/18/98 | 131 | 71.43 | 9 | 63 | 3.5 | 14 | Doing ok, nothing unusual | no change needed |
| 7/5/98 | 210 | 84.6 | 15 | 45 | 3 | 21 | On Vacation and had stressful week at work beforehand | Try to stay on your meal plan, even while on vacation |
| 6/14/98 | 145 | 60.1 | 4 | 69 | 4 | 9 | Nothing unusual overall, good week | Good Job, no change needed |
| 6/6/98 | 115 | 57 | 5 | 62 | 3 | 7 | Nothing unusual | Good work. |

Figure 56

Registration Options
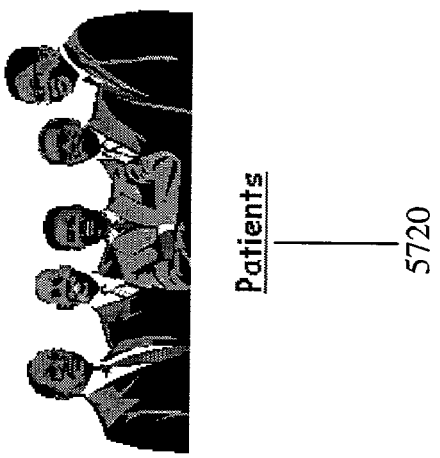
Patients — 5720
Practitioners — 5710
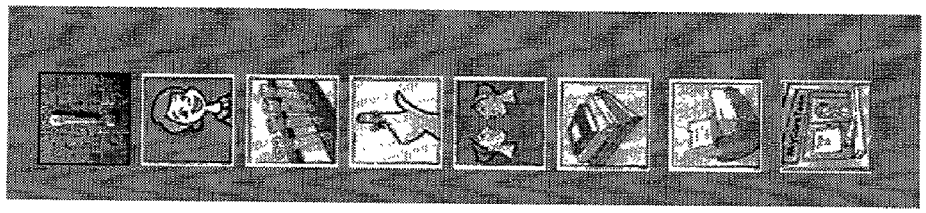
Figure 57

Figure 59

Lab Values Entry for Dialysis Patients

Patient : Doe, Jane
Test Date : 5/3/2000

Hospitalization No

| | |
|---|---|
| Kt/V : | TSH : |
| Albumin : 3.9 | T3 Uptake : |
| BUN : | T4 Total : |
| Calcium : 10.7 | T7/FTI : |
| Creatinine : 10.1 | Cholesterol : |
| Ferritin : | HDL : |
| Glucose : 185 | LDL : |
| HGBx3 : 36.9 | Trigycerides : |
| Iron : 44 | HBSAG : |
| Phosphate : 7.7 | HBSAB : |
| Potassium : 5 | HEPCAB : |
| PTH : | HgbA1C : |
| TIBC : 273 | |

Submit    Reset

Figure 62

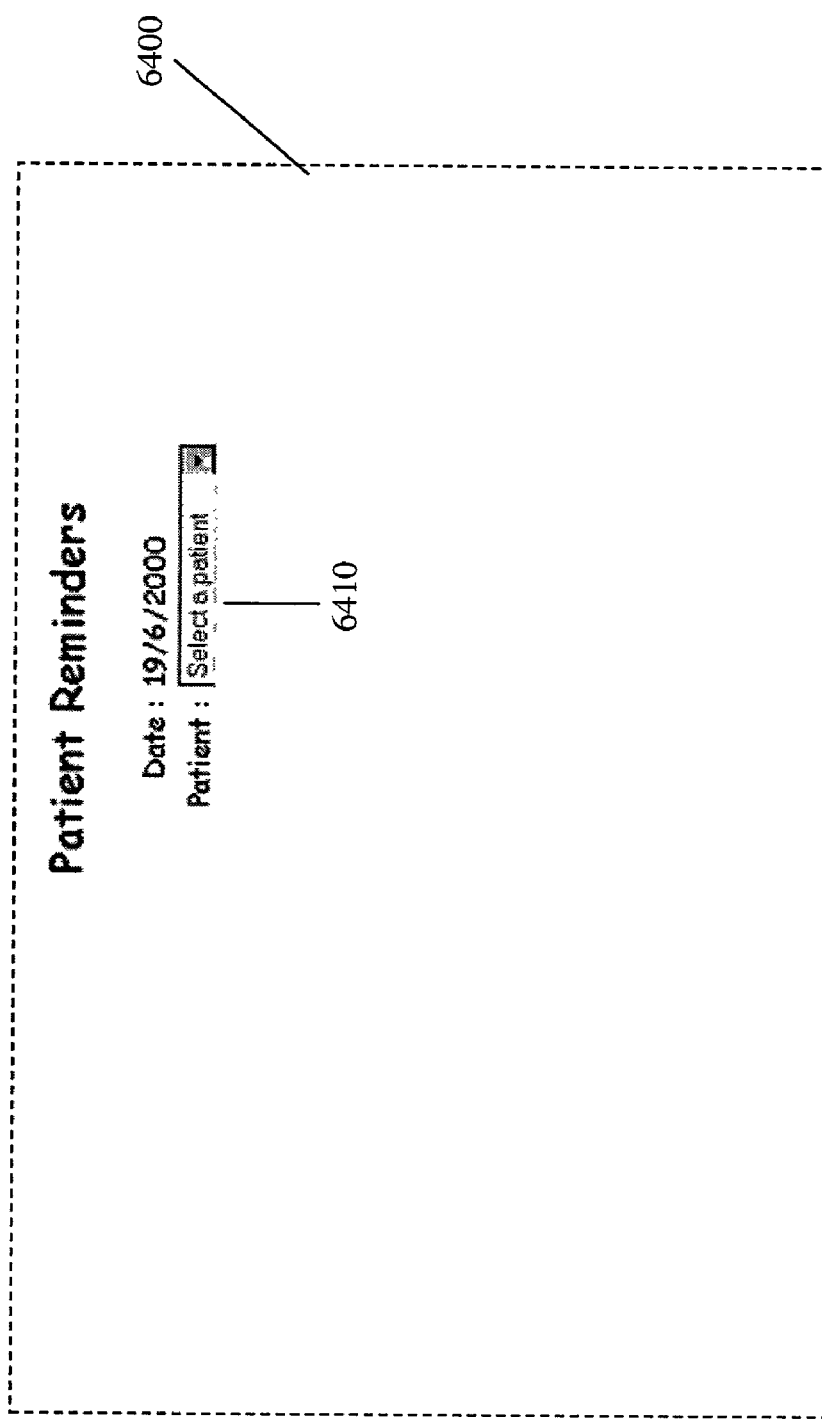
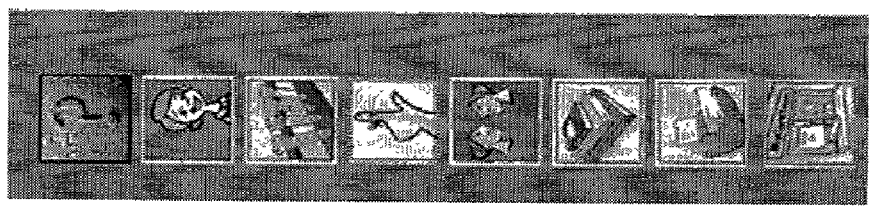
Figure 64

MyCareTeam

- provision of a full continuum of care
- integrated data management

The MyDiabetesTeam.org study (part of MyCareTeam.org) for patients with diabetes includes 20 patients with diabetes. These patients use electronic blood glucose meters, have personal computers, and have access to the Internet. Their glucose readings are transferred over the Internet to a central location where the patients have access to their clinical data using standard Web browser technologies at MyDiabetesTeam.org. Graphical and statistical representations of their glucose readings and laboratory data highlights areas of concern and identifies patterns in their data. They are automatically notified of lab values and blood glucose readings that are outside of identified target values. Their endocrinologist has access to their data and evaluates their condition in-between scheduled office visits. This allows the physician to identify areas of concern before they become serious problems.

(for information on our preliminary diabetes telemedicine study, click here)

Figure 67B

MyCareTeam

The study of MyKidneyTeam.org for patients with kidney failure focuses on those who are undergoing home peritoneal dialysis (PD). These patients are cared for through this web site. These patients use the Baxter Home Choice Pro (R) PD equipment to dialyze themselves. A modem connected to the Home Choice Pro (R) device allows a clinician to download the patient's PD data to a database at the ISIS Center and evaluate the results. The patient is freed from keeping paper records of their PD sessions and remembering to bring those records to their physician. The patients also have access to their data in a way they never had before. The data is presented via charts, graphs and other mechanisms that are understandable and informative.

(for information on our hemodialysis telemedicine study, click here)

The clinical data is accessible over the Internet through standard web browsers. For all patients involved in the MyCareTeam project, security measures are in place to ensure that each patient and their practitioners are

Figure 67C

MyCareTeam the only individuals with access to their clinical and personal data. Patients also have access to educational and training materials; open and scheduled chat rooms with other patients as well as practitioners; email alarms, warnings, and messages from practitioners; automatic alerts when data results are outside of targets; and automatic reminders of upcoming appointments, scheduled tests, and other important events.

The ISIS Center is a research division of the Department of Radiology at Georgetown University Medical Center. One area of research that we concentrate on is telemedicine. MyCareTeam is funded in part by the National Library of Medicine contract number N01-LM-6-3544 and by a grant from the Telemedicine and Advanced Technology Research Center (TATRC) of the Department of the Army at Fort Detrick Maryland.

(for more information on the ISIS Center, click here)

Figure 67D

MyCareTeam

Personnel

Seong K. Mun, PhD: Dr. Mun is the director of the ISIS Center and the project director for MyCareTeam.org. He secured funding for the project that made the development of the project possible.

Dr. Stephen Clement, MD: Dr. Clement is the clinical director of MyDiabetesTeam.org. He is an endocrinologist at Georgetown University Medical Center and is responsible for all patients with diabetes enrolled in this project.

Dr. James Winchester, MD: Dr. Winchester is the clinical director of MyKidneyTeam.org. He is a nephrologist at Georgetown University Medical Center and is responsible for all patients with kidney failure and on peritoneal dialysis enrolled in this project.

Figure 67E

Message List

7100

7110 — To / Select a patient

7120 — Subject

7130 — Reset

7140 — Add Message

| Date | To | From | Subject |
|---|---|---|---|
| 7/5/01 | DrISIS, Dummy | DrWRVA, Boston | Testing |
| 7/3/01 | Lucy, Lucy | DrISIS, Dummy | How're you doing? |
| 7/3/01 | Lucy, Lucy | DrISIS, Dummy | RE: RE: Test again |
| 7/3/01 | DrISIS, Dummy | Lucy, Lucy | RE: Test again |
| 7/3/01 | Philbin, Rick | DrISIS, Dummy | Message from Lucy |
| 7/3/01 | Lucy, Lucy | DrISIS, Dummy | Hello Phil |
| 7/3/01 | Lucy, Lucy | DrISIS, Dummy | Test again |
| 7/3/01 | Lucy, Lucy | Lucy, Lucy | Testing |
| 7/2/01 | DrISIS, Dummy | Lucy, Lucy | RE: test |
| 7/2/01 | DrISIS, Dummy | Brown, Charlie | test |
| 6/29/01 | DrISIS, Dummy | Lucy, Lucy | Good Morning |
| 6/29/01 | DrISIS, Dummy | Lucy, Lucy | RE: RE: RE: Test of message from contact page |
| | | | RE: RE: How're you doing? |

Figure 71

Message List

7106

| Date | To | From | Subject |
|---|---|---|---|
| 7/3/01 | Lucy, Lucy | DrISIS, Dummy | How're you doing? |
| 7/3/01 | Lucy, Lucy | DrISIS, Dummy | RE: RE: Test again |
| 7/3/01 | DrISIS, Dummy | Lucy, Lucy | RE: Test again |
| 7/3/01 | DrISIS, Dummy | Lucy, Lucy | Message from Lucy |
| 7/3/01 | Lucy, Lucy | DrISIS, Dummy | Test again |
| 7/3/01 | DrISIS, Dummy | Lucy, Lucy | Testing |
| 7/3/01 | Lucy, Lucy | DrISIS, Dummy | How're you doing? |
| 7/2/01 | DrISIS, Dummy | Lucy, Lucy | RE: test |
| 7/2/01 | DrISIS, Dummy | Lucy, Lucy | test |
| * 6/29/01 | DrISIS, Dummy | Lucy, Lucy | RE: RE: RE: Test of message from contact page |

Figure 73

CLINICAL MANAGEMENT SYSTEM FROM CHRONIC ILLNESSES USING TELECOMMUNICATION

This invention was made with government support under grant number N01-LM-6-3544 awarded by NIH and grant number DAMD17-94-V-4015 awarded by DOD. The Government has certain rights in the invention.

This nonprovisional application claims the benefit of U S. Provisional Application No. 60/265,306, filed Feb. 1, 2001.

BACKGROUND OF THE INVENTION

1. Field of Invention

The invention generally relates to using a distributed network to clinically manage chronic illnesses.

2. Description of Related Art

Managing chronic illnesses is both costly and difficult. Both patients and healthcare practitioners wish to decrease costs and inconvenience by reducing unnecessary clinic visits. However, the management quality of a chronic illness increases with the frequency that the clinical data obtained from the patient is updated. Automated and manual medical devices may be operated by a patient to provide the updated clinical data. However, the patient can operate the device improperly or has little opportunity to supply the clinical data to the healthcare practitioner.

For example, U.S. Pat. No. 6,039,688 to Douglas et al. describes a therapeutic behavior modification program, compliance monitoring and feedback system. This system provides a series of milestones for patients to achieve to maintain good health. Patients may access the system over the Internet to review compliance data and to receive motivation. This system is designed around a community support motif that allows the patient to access various graphic representations of a community to access different parts of the system.

SUMMARY OF THE INVENTION

However, patients with chronic illnesses often resist using such systems as that described in the 688 patent because such systems often feel impersonal. Patients also often fail to supply the clinical data through the conventional automated and manual medical devices, again due to the impersonal nature of the systems used to supply such data to the healthcare practitioner. Thus, while such systems provide the ability to manage a chronic illness using a distributed network to supply the necessary clinical data from the patient to the healthcare practitioner and to communicate information to and from the patient, patients with chronic illnesses often tend to avoid using such systems.

Rather, patients with chronic illnesses often strongly tend to prefer actually visiting a clinic dedicated to managing the healthcare of patients with such chronic illnesses. At such actual clinic visits, the patient interacts with various nurses and other healthcare management staff members and, most importantly, with a personal healthcare practitioner with whom the patient has developed a relationship. However, such actual clinic visits are expensive for healthcare insurers and are burdensome for patients with chronic illnesses to make at the needed frequency.

This invention provides systems and methods that provide a graphical user interface-based clinical management that simulates an actual visit to a physical clinic directed to managing a chronic illness.

This invention separately provides systems and methods that increase patient compliance by replicating the experience of the patient visiting an actual clinic directed to managing a chronic illness.

In various exemplary embodiments of the systems and methods according to this invention, the patient interacts with the clinical management system via a series of graphical user interface screens accessed over a distributed network. Various initial graphical user interface screens replicate the experience of actually visiting a clinic directed to a particular chronic illness. Additional graphical user interface screens allow the patient having a chronic illness to submit updated clinical information to the clinical management system. Various other graphical user interface screens allow the patient having a chronic illness to communicate with that patient's personal healthcare practitioner as well as various staff members of the clinic that are involved with that patient in managing that patient's chronic illness. Various other graphical user interface screens provide management information to the patient usable to aid the patient in managing that patient's chronic illness, such as warnings, information and care reminders.

Still other various exemplary graphical user interface screens allow a patient having a chronic illness to access current and archived information regarding that chronic illness, such as new findings, management advice and the like.

In various exemplary embodiments, the clinical management system may be used to manage a plurality of different chronic illnesses. As is well known in the art, patients having one chronic illness often develop one or more additional chronic illnesses. In this case, the patient having multiple chronic illnesses can use a single clinical management system to manage all of that patient's chronic illnesses using a consistent metaphor for the various chronic illnesses. In various exemplary embodiments, while different specific information may be provided depending on the type of chronic illness, the information is provided using a consistent look and feel to the graphical user interface screens. However, to distinguish between different types of chronic illnesses, in various exemplary embodiments, when dealing with a particular chronic illness, the graphical user interfaces have at least one appearance characteristic that is modified to visually indicate the particular chronic illness to which that screen currently applies. For example, in various exemplary embodiments, the appearance of the graphical user interface screens can be color coded depending on the particular chronic illness.

In various exemplary embodiments, to allow a patient who has multiple chronic illnesses to easily determine which chronic illness is being managed, an elevator metaphor is used that replicates the organization of an actual clinic into separate floors for each different chronic illness.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein:

FIG. 22 shows one exemplary embodiment of a screen of a graphical user interface usable to display medication tables according to this invention;

FIG. 23 shows one exemplary embodiment of a screen of a graphical user interface usable to display a data entry table for medication according to this invention;

FIG. 27 shows one exemplary embodiment of a screen of a graphical user interface usable to enter patient comments into a tabular summary according to this invention;

FIG. 33 shows the main patient data screen of FIG. 30 displaying another educational article according to this invention;

FIG. 37 shows a second exemplary embodiment of the screen of the graphical user interface usable to display medication tables according to this invention;

FIG. 39 shows one exemplary embodiment of a screen of a graphical user interface usable to display recipes available to patients according to this invention;

FIG. 40 shows the graphical user interface screen of FIG. 34 displaying an educational article on kidney disease;

FIGS. 41A-B show the graphical user interface of FIG. 34 displaying an educational article about peritoneal dialysis having selectable links according to this invention;

FIGS. 43 and 44 show various exemplary embodiments of screens of a graphical user interface displaying procedure instructions to a patient;

FIGS. 45A-45C and 46A-46E show various exemplary embodiments of screens of a graphical user interface usable to display specific procedure instruction and troubleshooting information for performing the procedure illustrated in FIGS. 43 and 44;

FIGS. 47A-47I show one exemplary embodiment of a screen of a graphical user interface usable to display daily routine information for peritoneal dialysis patients according to this invention;

FIG. 48 shows another exemplary embodiment of a screen of the graphical user interface according to this invention usable to display on-screen contextually relevant messages;

FIGS. 52, 54 and 55 show various exemplary embodiments of screens of a graphical user interface displaying medication tables to a practitioner according to this invention;

FIG. 56 shows one exemplary embodiment of a screen of a graphical user interface displaying tabular data summary and healthcare practitioner comments to a patient according to this invention;

FIG. 57 shows one exemplary embodiment of a screen of a graphical user interface usable to add a new patient or practitioner according to this invention;

FIG. 59 shows one exemplary embodiment of a screen of a graphical user interface usable to submit patient registration information according to this invention;

FIGS. 60-62 show various exemplary embodiments of the screens of a graphical user interface usable to submit patient lab data according to this invention;

FIGS. 63-65 show various exemplary embodiments of screens of a graphical user interface usable to input patient reminder information according to this invention;

FIGS. 67A-67G show one exemplary embodiment of a screen of a graphical user interface displaying project description information according to this invention;

FIG. 71 shows one exemplary embodiment of a healthcare practitioner message list screen of a graphical user interface according to this invention;

FIG. 73 shows a first exemplary embodiment of a healthcare practitioner message list screen of a graphical user interface according to this invention after a patient has been selected by a healthcare practitioner.

DETAILED DESCRIPTION OF PREFERRED EMBODIMENTS

Figure 1:
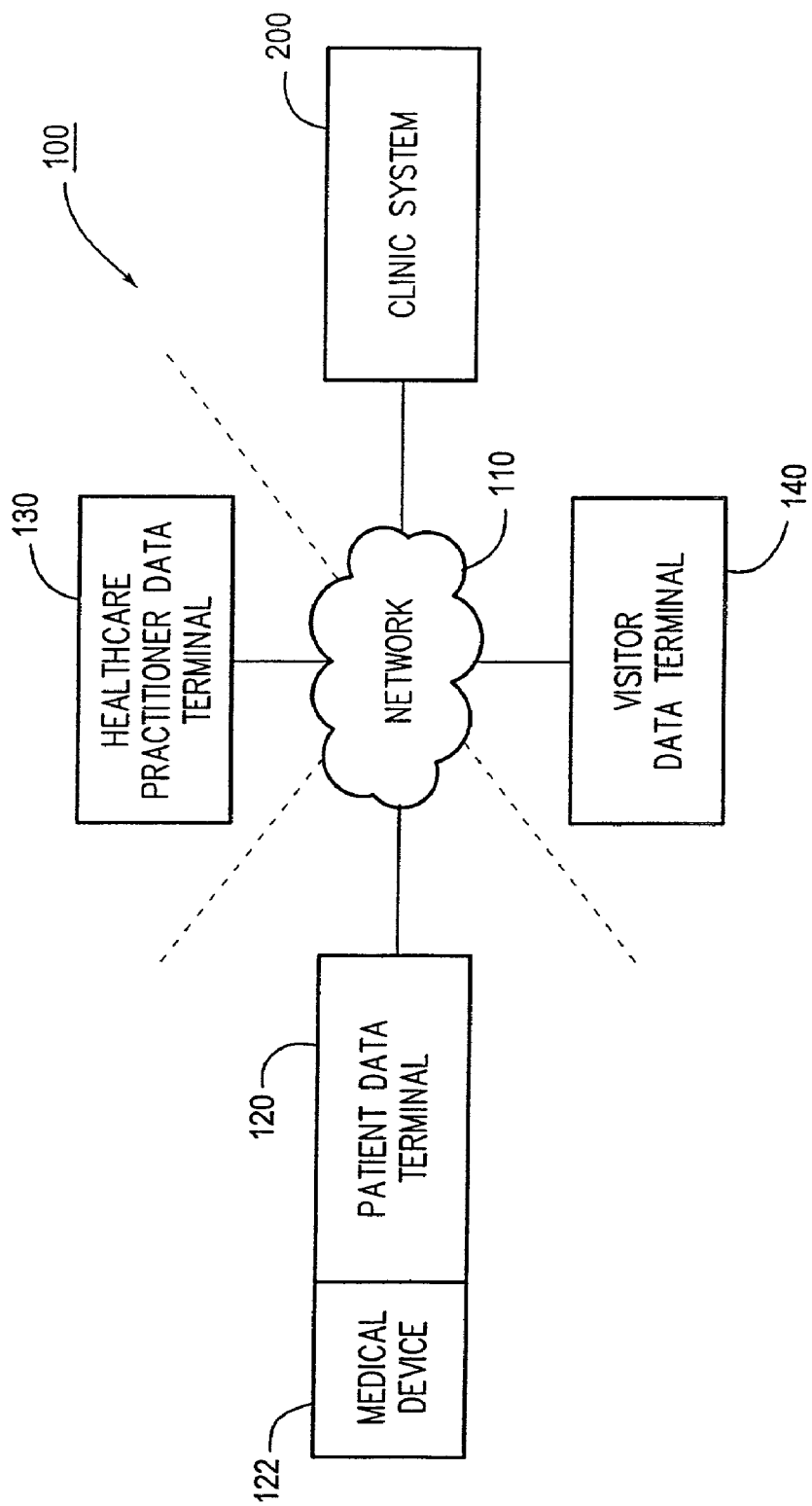
FIG. 1 is a block diagram of one exemplary embodiment of a chronic illness management system according to this invention.

FIG. 1 shows one exemplary embodiment of a chronic illness management system 100 that is usable to manage one or more chronic illnesses. As shown in FIG. 1, the chronic illness management system 100 according to this invention includes one or more healthcare practitioner data terminals 130, one or more patient data terminals 120, and zero, one or more visitor data terminals 140, that are connected by a network 110 to a clinic system 200 that implements a virtual clinic. The network 110 may be a local area network (LAN), a wide area network (WAN), the Internet, an intranet, an extranet, or any other known or later-developed type of distributed network 110 usable to connect patients, healthcare practitioners and/or visitors to the clinic system 200.

Thus, the chronic illness management system 100 connects patients, healthcare practitioners and/or visitors to the virtual clinic over a distributed network. Access and privileges of the chronic illness management system 100 are determined by a user's status as a patient, a healthcare practitioner, or a visitor. Patient users may provide quantitative clinical data, based on the operation of a medical device 122, and/or comments to their healthcare practitioner over one of the one or more patient data terminals 120. The chronic illness management system 100 uses the network 110 to connect patients having one or more chronic illnesses, healthcare practitioners of various occupations, for example, specialized healthcare practitioners, primary care healthcare practitioners, nurses, and the like, and visitors to the clinic system 200.

In various exemplary embodiments, each patient data terminal 120, each healthcare practitioner data terminal 130, and/or each visitor data terminal 140 can be implemented using standard personal computers, laptop computers, handheld computers, and/or personal digital assistants, or the like, having one or more of a network interface, a data display device, such as a video monitor, one or more input devices, such as a keyboard and/or a mouse, and a network browser software program, or any other known or later-developed hardware elements, any other known or later-developed software components, or any known or later-developed combination of such hardware components and software components that may provide equivalent functionality. Each patient data terminal 120 may also have an input/output interface to which the medical device 122 can be connected to allow clinical data to be directly downloaded from the medical device 122 and sent over the network 110 to the clinic system 200.

Figure 2:
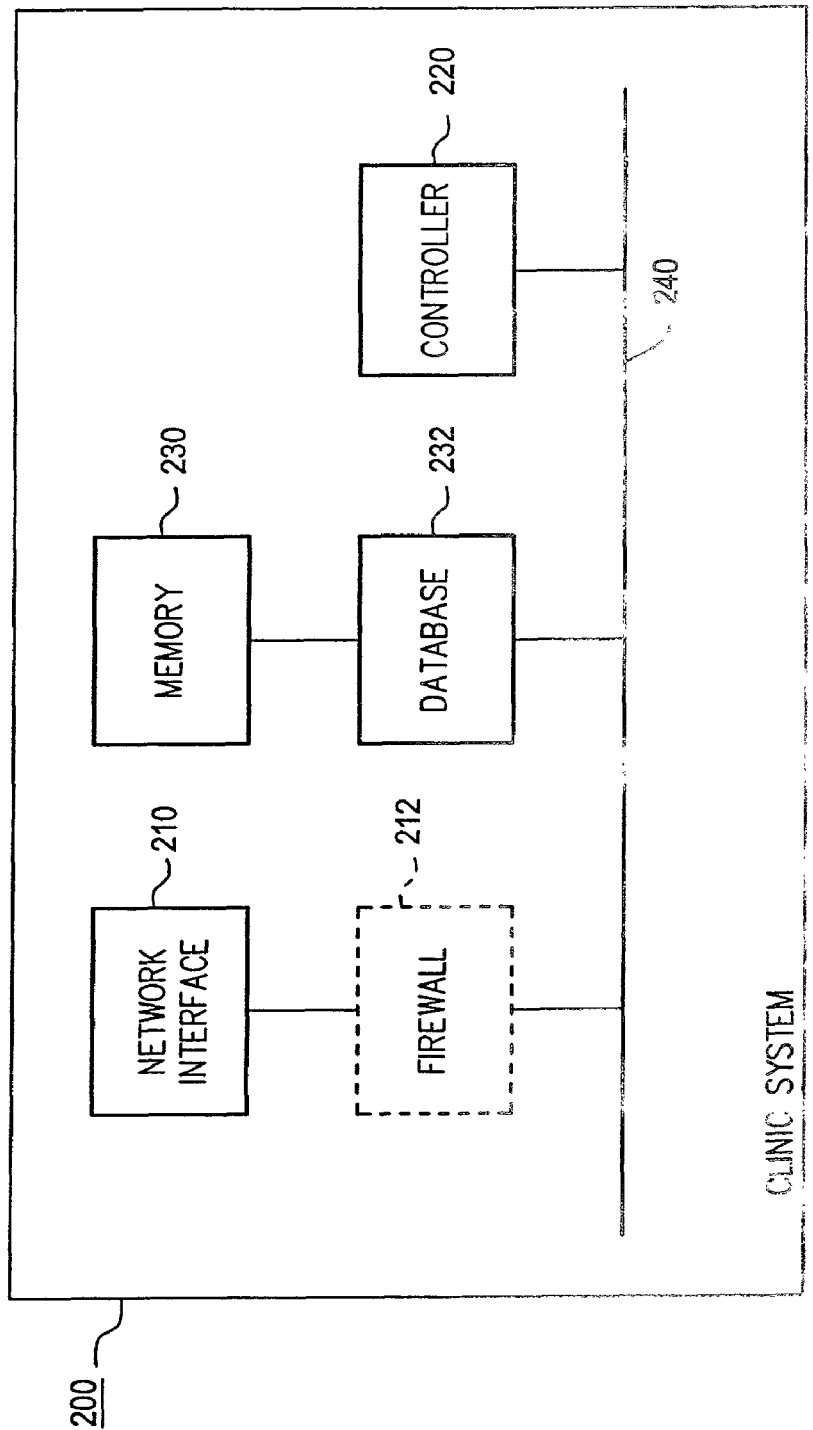
FIG. 2 is a block diagram showing in greater detail one exemplary embodiment of the clinic system of the chronic illness management system of FIG. 1.

FIG. 2 shows in greater detail one exemplary embodiment of the clinic system 200 of FIG. 1. In the exemplary embodiment of the system 200 shown in FIG. 2, the clinic system 200 shows a network interface 210, an (optional) firewall 212, a memory 230, a controller 220, a control/data bus 240 and a database 232 that stores at least some of the information described below. The network interface 210 can, in various exemplary embodiments, provide system security by encrypting and transmitting through a secure portion by using, for example, hypertext transfer protocol secure (HTTPS) running over a secure socket layer (SSL) or by any other known or later-developed security mechanism. The optional firewall 212, if implemented, uses a combination of hardware elements and/or software components that moderates the communication of the clinic system 200 with systems external to the clinic system 200 and vice versa. The optional firewall 212, if implemented, uses, for example, an external proxy server that decides whether communications are safe to pass through to the clinic system 200.

In general, the memory 230 can include one or more of random access memory, read only memory, hard disks, writeable optical disks, flash memory or the like. In general, the controller 220 receives data from and generates instructions to the other components of the clinic system 200, and reads, writes and processes data. The database 232 stores at least information concerning patients and healthcare practitioners, clinical data received from patients, laboratory test results, information concerning medications that will be or have been prescribed to and/or used by one or more patients, educational information, and general information concerning the chronic illness management system 100.

It should be appreciated that the following discussion is generally equally directed to standard windowed graphical user interfaces and graphical user interfaces using web-based implementations, where each graphical user interface "screen" is a distinct web page written in HTML, XML or any other known or later-developed web page authoring language. As a result, in various exemplary embodiments, the selectable icons of the following description are implemented as hypertext links to related web pages or to distinct regions of a current web page. However, it should be appreciated that any other known or later-developed graphical user interface implementation technique could be used to implement the graphical user interface screens and/or graphical user interface elements described herein.

Thus, it should also be appreciated that this graphical user interface can be implemented as a Windows-based system, rather than as a web-based system. In this case, the graphical user interface screens are distinct portions of the graphical user interface that is accessed by specific Windows events that are associated with particular selectable icons or other interactive elements or widgets. As a result, the selectable icons and other interactive elements of these graphical user interface screens can be implemented as Windows widgets or the like.

It should also be appreciated that, in the following discussion of the graphical user interfaces and screens according to this invention, selecting a selectable icon or other interactive element can include activating any feature of the graphical user interface that generates a new screen or allows the patient to enter data, for example, by using a drop-down list box, a dialog box, an option button, or the like. An on-screen indicator usable to select a feature of the graphical user interface may be, for example, a mouse pointer, a cursor, or any other known or later-developed on-screen indicator used in conjunction with, for example, a mouse, a touch pad, a touch screen, a light pen, a joystick, a trackball or any other known or later-developed on-screen location input device.

Figure 3:
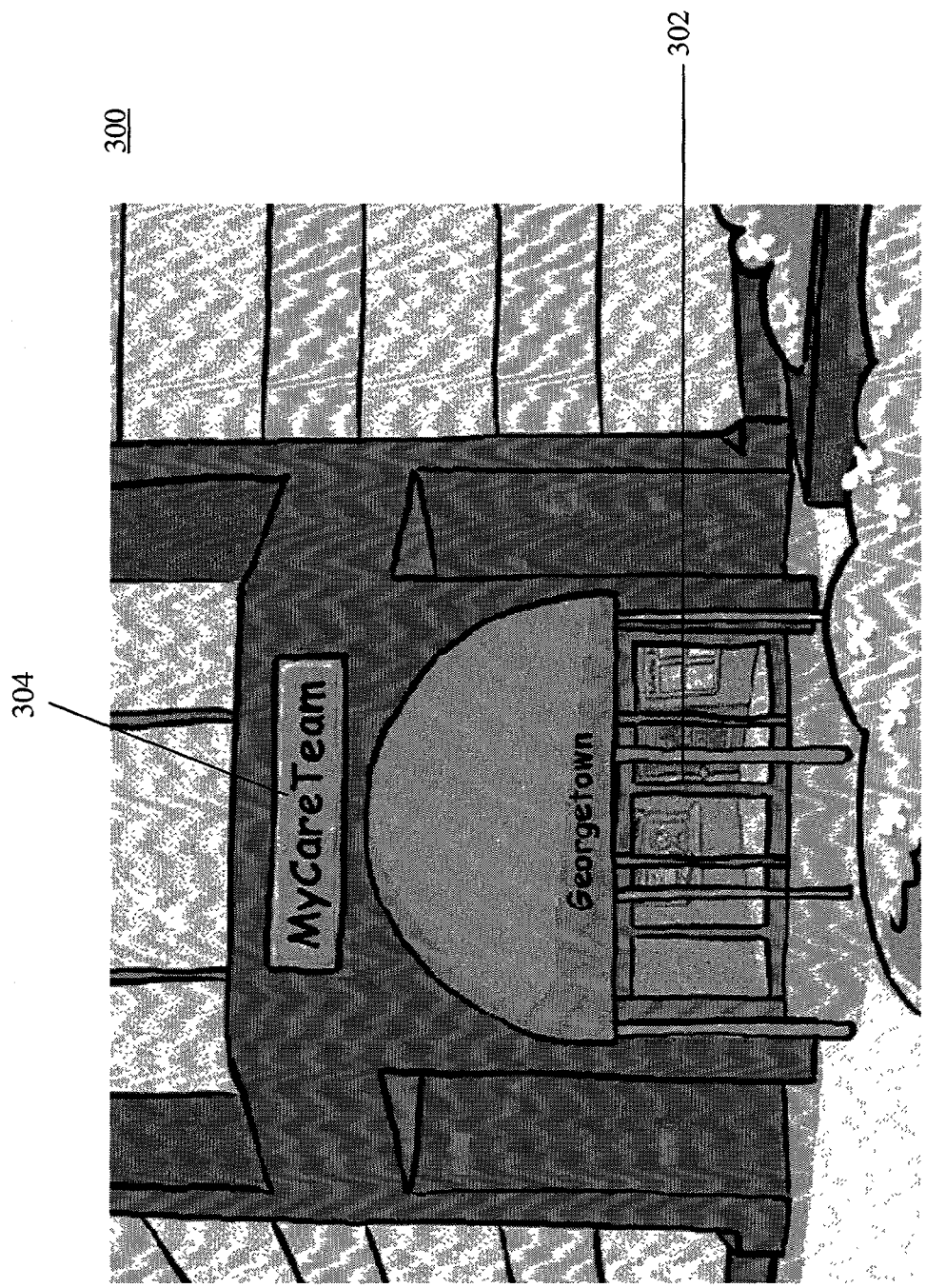
FIG. 3 shows one exemplary embodiment of a screen of a graphical user interface showing a virtual clinic according to this invention.

As shown in FIG. 3, when a patient or a visitor logs onto the chronic illness management system 100 from one of the data terminals 120, 130 or 140 via the network 110, the clinic system 200 presents a graphical user interface screen 300 having a graphic representation of a clinic 304 of the outside of a clinic building. In some exemplary embodiments, this graphic representation of the clinic 304 shows, for example, an entrance door 302 to the clinic, and one or more of a name of the clinic or the building, reflections of the sky in the clinic windows., surrounding walkways and flowerbeds, and a name of the clinic program to which the patient belongs. This graphic representation of the clinic 304 provides the patient with a feeling that the patient is effectively visiting an actual clinic, which is both familiar and assuring.

In various exemplary embodiments, the graphic representation of the clinic 304 further elicits a feeling of timeliness by changing aspects of the graphic representation of the clinic 304 to reflect the time of day and time of year when the patient logs onto the system. For example, if the patient logs on during a summer day, the graphic representation of the clinic 304 shown in FIG. 3 shows the clinic during a summer day with blue skies reflected in the clinic windows and blossoming flowerbeds outside the clinic entrance. Other graphic representations of the clinic 304 are automatically displayed on the screen corresponding to the different seasons and time of day. For example, a graphic representation for a winter day may show blue skies reflected in the clinic windows, snow piled on the flowerbeds and ledges of the clinic, and snowflakes drifting down from the sky. The graphic representation of the clinic 304 for both summer and winter nights may, for example, show darkened clinic windows that reflect night skies and stars. Aspects of the graphic representation of the clinic 304 can be altered based on holidays and/or other calendar events.

The graphic representation of the clinic 304 shown in FIG. 3 is part of a graphical user interface that allows the patient and others to access various screens of the chronic illness management that generally mimic activities that could normally have been pursued during an actual visit by the patient to the clinic. Various clinical data and information elements can also be displayed to the patient using these graphical user interface screens. When the patient selects the entrance door icon 302 of the graphic representation of the clinic 304 shown in FIG. 3, in various exemplary embodiments, the entrance door icon 302 opens using animation. In any case, a graphical user interface screen 400, as shown in FIG. 4, of the graphical user interface is displayed in place of the screen 300.

Figure 4:
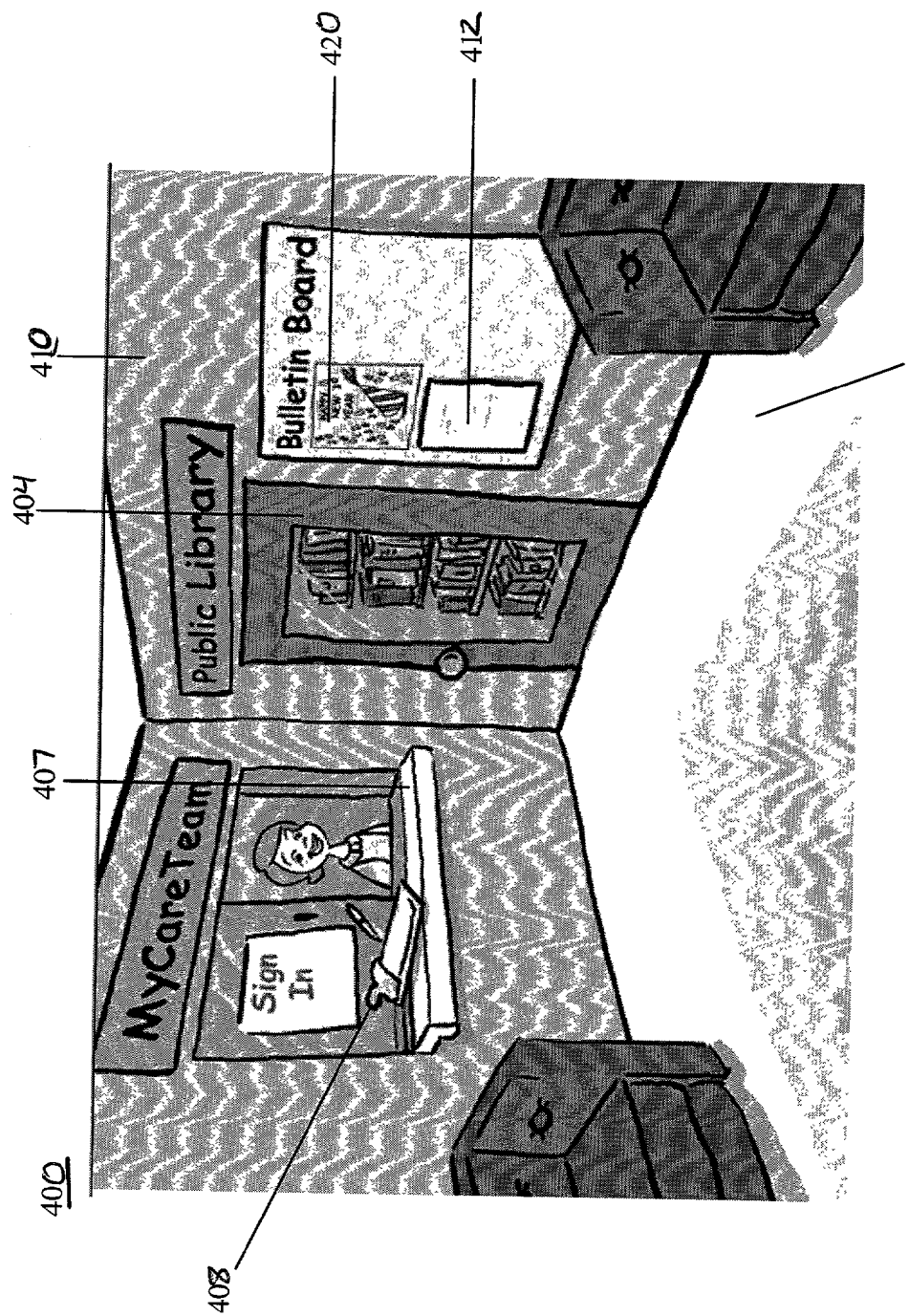
FIG. 4 shows one exemplary embodiment of a screen of a graphical user interface representing a lobby of the virtual clinic of FIG. 3.

FIG. 4 shows one exemplary embodiment of the graphical user interface screen 400. The screen 400 includes a graphic representation of a clinic lobby 402. When used, the animated graphic representation of opening the entrance door icon 302 to enter the clinic lobby 402 invokes the feeling of an actual clinic visit. By mimicking an actual clinic visit, the patient's familiarity with the clinical monitoring program can be enhanced, as can be the patient's compliance with the monitoring program. As shown in FIG. 4, the graphical representation of the clinic lobby 402 includes, for example, furniture and rugs, a smiling receptionist standing behind a counter, a sign-in clipboard icon 408 located on a counter 407. a door icon 404 leading to a public access library area, and a bulletin board icon 410 usable to access a bulletin board system. Again, the graphic representation of the clinic lobby 402 shows a scene that the patient would expect to encounter during an actual clinic visit.

Figure 7:
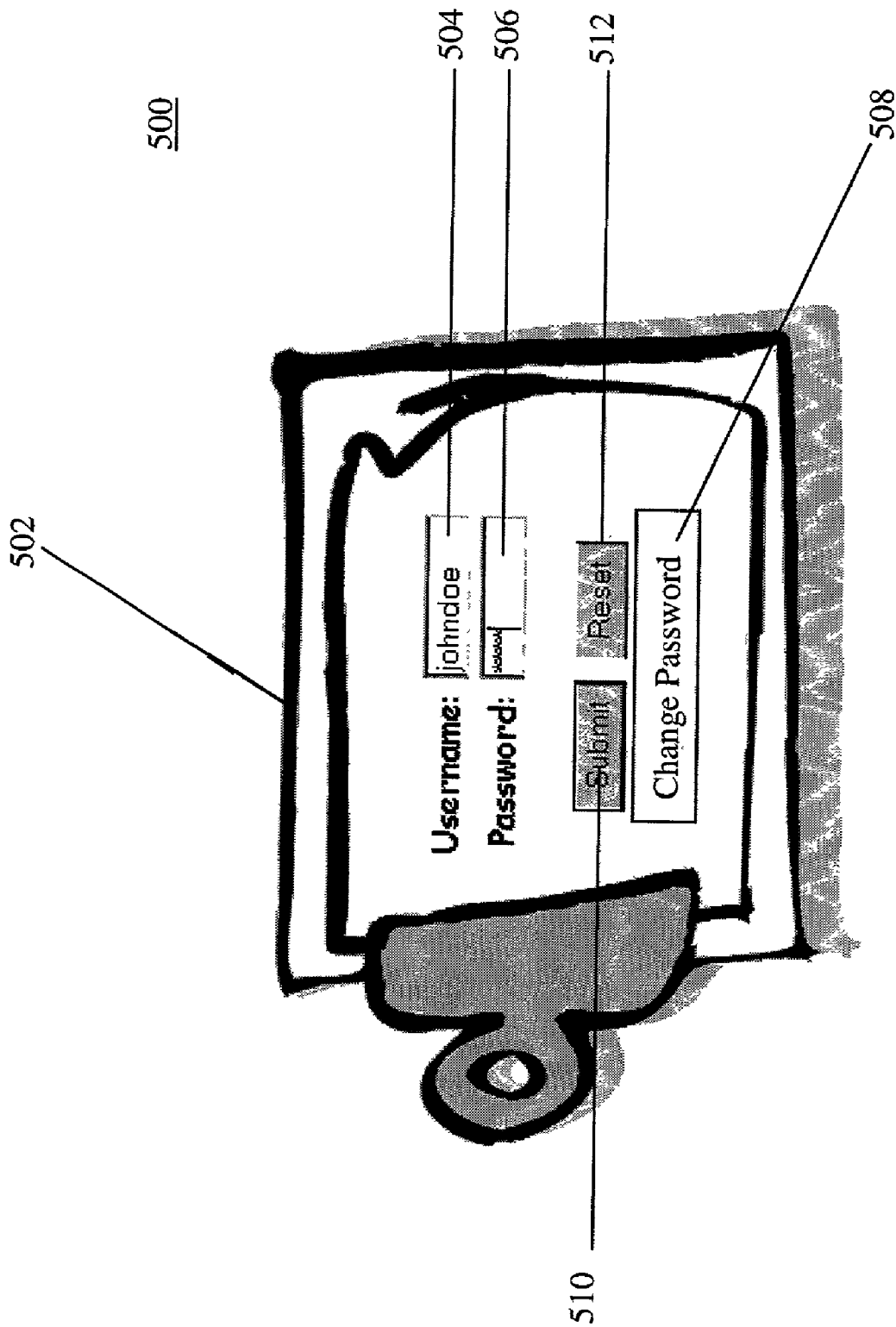
FIG. 7 shows one exemplary embodiment of a screen of a graphical user interface representing a clipboard of the lobby of FIG. 4.

In various exemplary embodiments, when the clipboard icon 408 is initially indicated, such as by hovering the cursor over the clipboard 408, (or is initially selected), the clipboard icon 408 rises by animation above the counter 407. This rising of the clipboard icon 408 invites the patient to sign into the clinic, just as the patient would do in an actual clinic visit. In response to the user selecting the raised clipboard icon 408, a graphical user interface screen 500, as shown in FIG. 7, is displayed in place of the graphical user interface screen 400.

Figure 5:
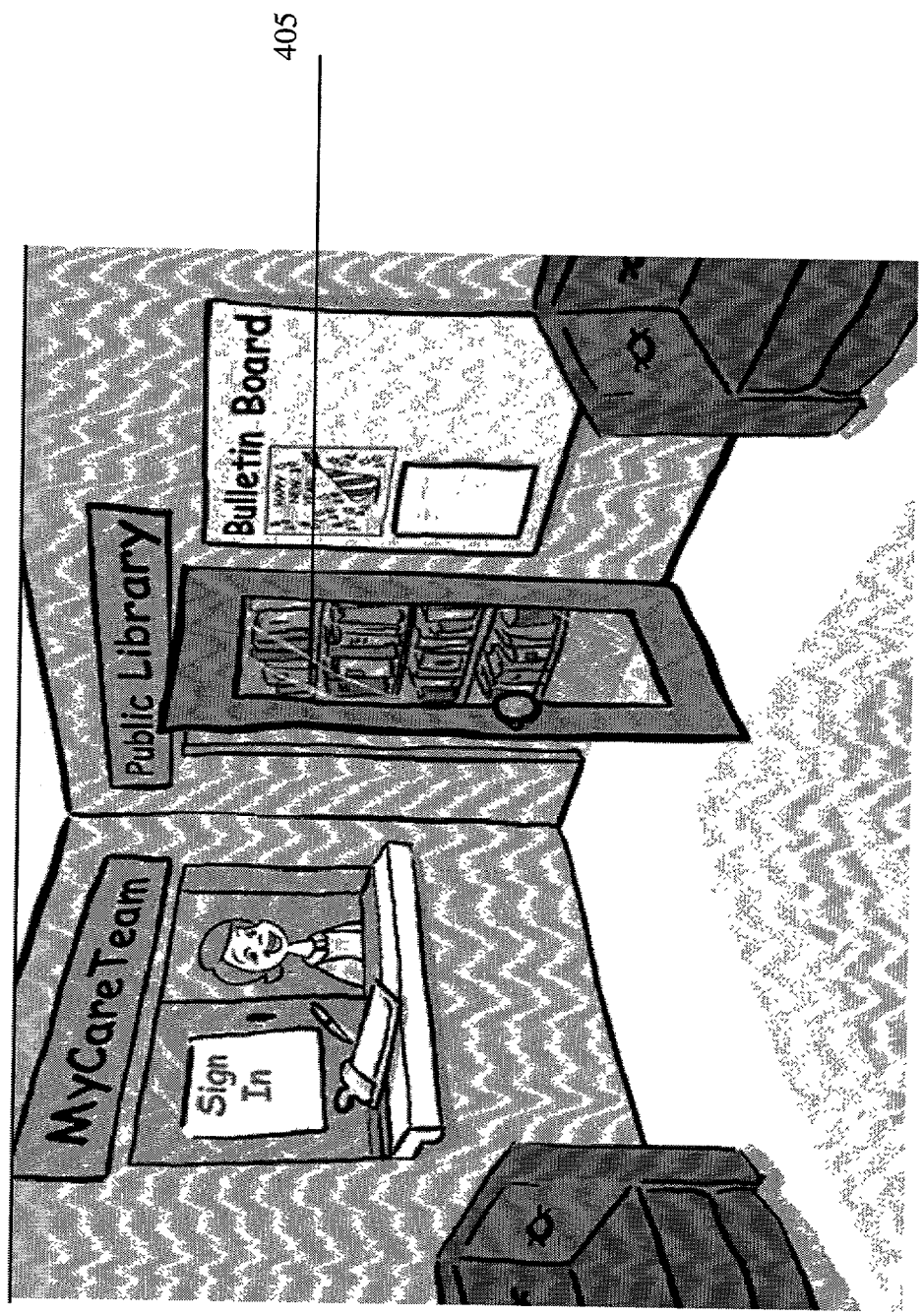
FIG. 5 shows one exemplary embodiment of a screen of a graphical user interface representing an open door to a public library of the virtual clinic of FIG. 3.

When the door icon 404 to the public access library area of the clinic lobby 402 of FIG. 4 is selected, the door icon 404 opens by animation to the position shown in FIG. 5. This open door icon 405 invites not only patients, but other visitors who have accessed the chronic illness management system 100 to access public information about the chronic illness management system 100.

Figure 6:
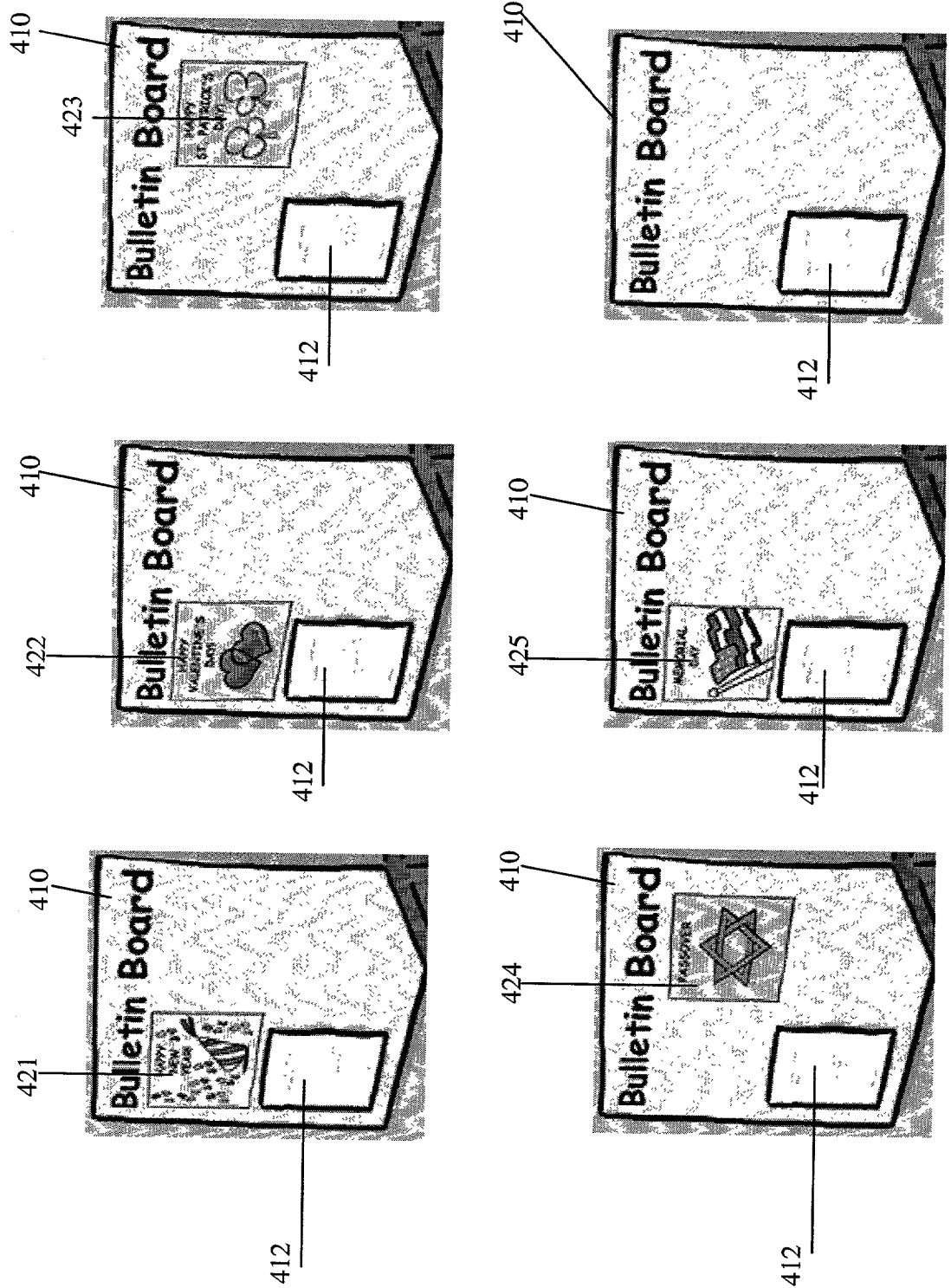
FIG. 6 shows various exemplary embodiments of portions of a graphical user interface screen representing bulletin board notices according to this invention.

The bulletin board 410 of FIG. 4 displays various monthly notice icons 420 that may be characterized by graphic designs corresponding to the respective content of the notice. For example, one type of notice may be a holiday notice that contains a graphic design corresponding to the respective holiday for the current month. For example, as shown in FIG. 6, a January holiday notice 421 may display a party hat, while the other graphics 422-425 for the holiday notices may be displayed during the appropriate month. Other graphic designs may readily correspond to other holidays or events. Selecting a different bulletin board notice icon 412 of the bulletin board 410 shown in FIG. 4 may provide access to educational information on chronic illnesses managed by the clinic system 200. This information may be provided, for example, by links to other network sites, such as Internet sites or worldwide web sites that provide educational information about particular chronic illnesses. For example, during January, a link to the website of the American Diabetes Association may warn diabetics to watch for freezing of their extremities.

Figure 13:
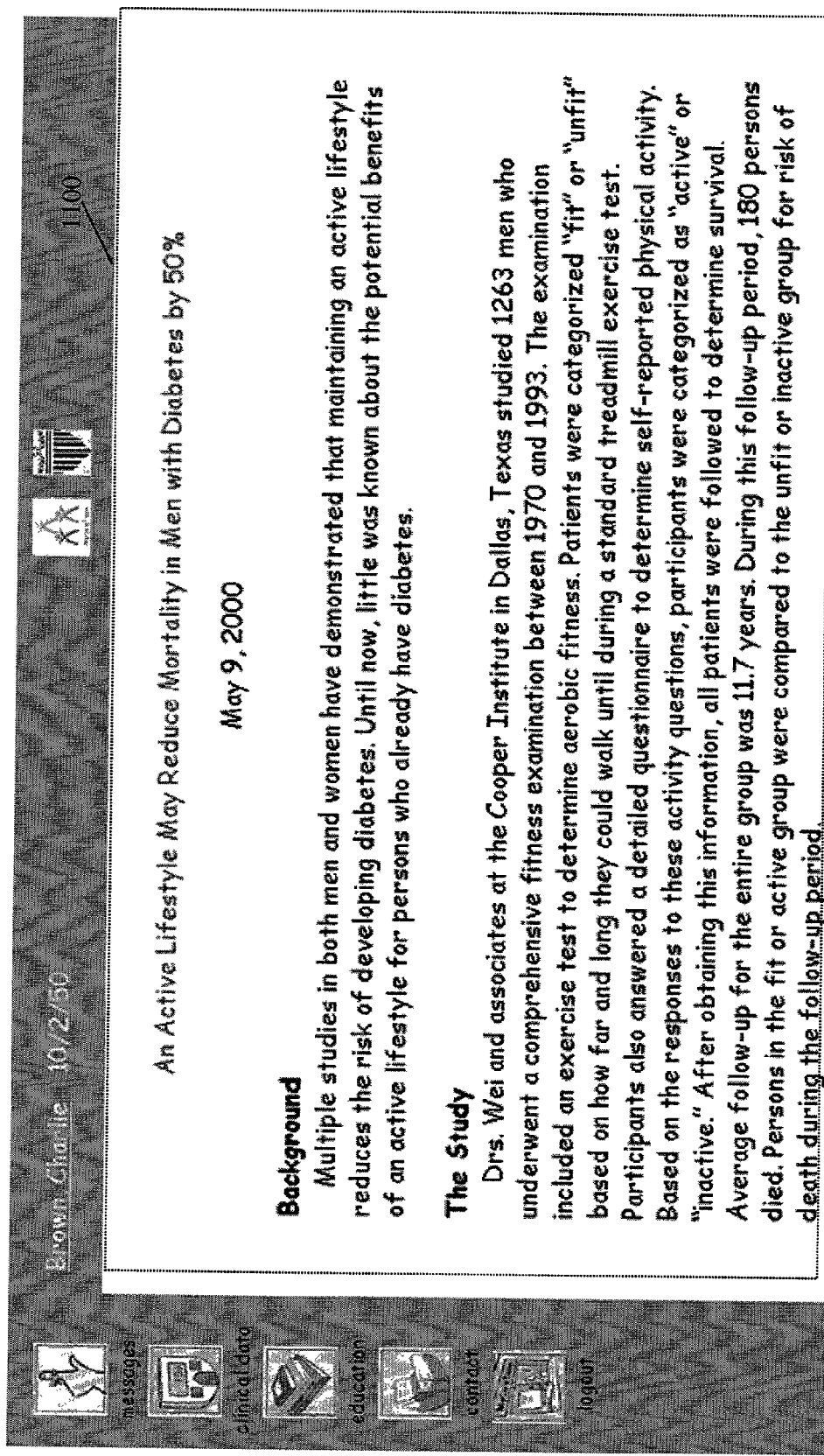
FIG. 13 shows one exemplary embodiment of a screen of a graphical user interface usable to access an educational article according to this invention.

The bulletin board icon 410 shown in FIG. 4 also displays a news item icon 412 concerning chronic illnesses managed by the clinic system 200. When the news item icon 412 is selected, the graphical user interface screen 1100, as shown in FIG. 13, is displayed in place of the graphical user interface screen 400.

As shown in FIG. 7, the graphical user interface screen 500 includes a graphic representation of a clipboard 502. The patient enters the patient's name or a username and a password into the clipboard 502, for example, by using a pair of data entry input boxes 504 and 506. Data is entered into these data entry boxes 504 and 506 by the patient using the keyboard or other data entry device of the patient's data terminal 120. Access to other screens of the clinic system 200, which would otherwise be open to an authorized patient, would be denied to a patient or other person who lacks an authorized password. The patient may change an authorized password by selecting the change password icon or hypertext link 508 shown on the clipboard 502 in FIG. 7.

The graphical user interface screen 500 shown in FIG. 7, and various other data entry screens displayed by the clinic system 200, frequently show two buttons: a submit button 510 and a reset button 512. The submit button 510, when selected, sends the data entered by the user, such as the patient's name and password entered into the data entry boxes 504 and 506 to the clinic system 200. The reset button 512 allows the patient to reset the data in the data entry boxes 504 and 506 when an error is made. Of course, it should be appreciated that the submit and reset functions associated with the submit and reset buttons 510 and 512, respectively, may also be implemented by enabling the enter and backspace keys of a keyboard. It should also be appreciated that data entry in the various screens of the chronic illness management system 100 described herein is not limited to buttons, but may also include, for example, dropdown list boxes, data entry input boxes, dialog boxes and the like, and/or commercial voice recognition software programs that recognize data entry commands and entered data.

Figure 8:
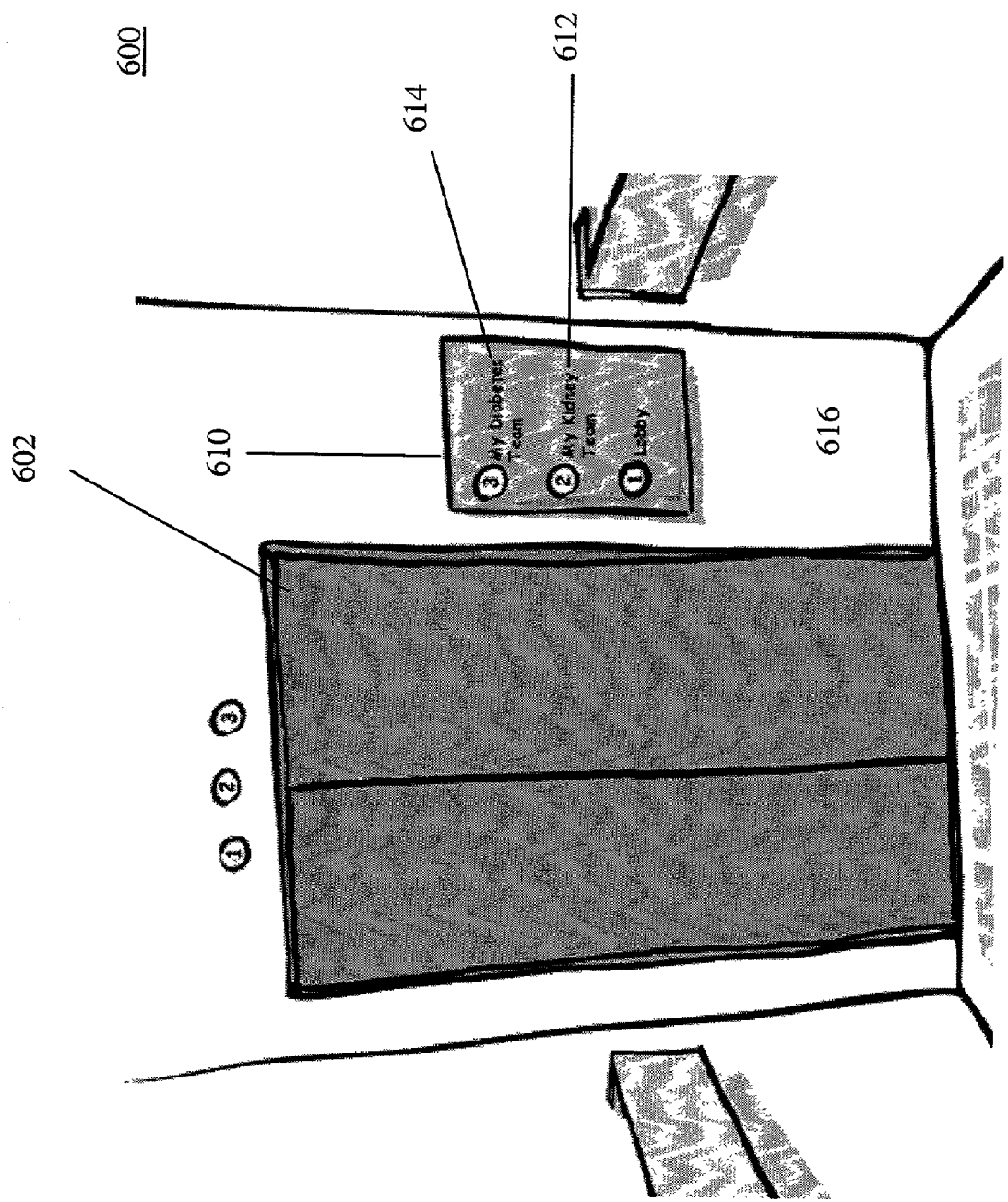
FIG. 8 shows one exemplary embodiment of a screen of a graphical user interface representing an elevator metaphor according to this invention.

Once the patient has gained authorized access to the clinic system 200, the clinic system 200 recognizes that patient's chronic illness from its patient records stored in the database 232. However, the clinic system 200 may be used to manage more than one chronic illness of a patient. As shown in FIG. 8, in various exemplary embodiments, when such a patient, for example, a patient suffering from both diabetes and kidney disease, signs into the clinic on the clipboard 502 shown in FIG. 7, the graphical user interface screen 500 is automatically replaced with the graphical user interface screen 600, as shown in FIG. 8. In various exemplary embodiments, the screen 600 includes a graphic representation of an elevator 602 having a control panel 610. By selecting, for example, the second floor elevator button icon 612, which is labeled "My Kidney Team", the patient signals that patient's intention to visit the kidney disease clinic portion of the clinic system 200. Similarly, by selecting the third floor elevator button icon 614, labeled "My Diabetes Team", the patient signals that patient's intention to visit the diabetes clinic portion of the clinic system 200.

Figure 9:
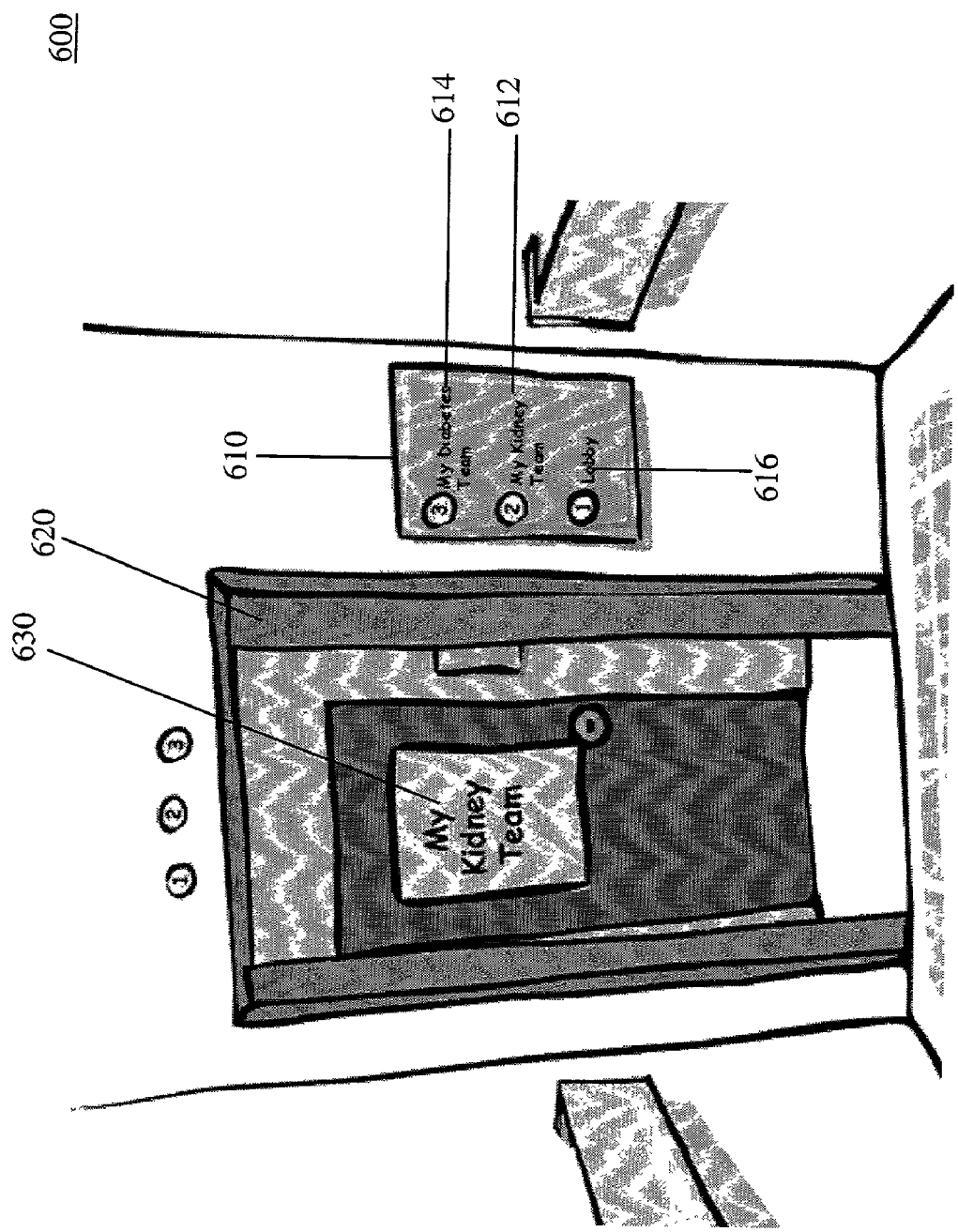
FIG. 9 shows one exemplary embodiment of a screen of a graphical user interface representing an opened elevator door showing a virtual clinic for a specific chronic illness according to this invention.
Figure 10:
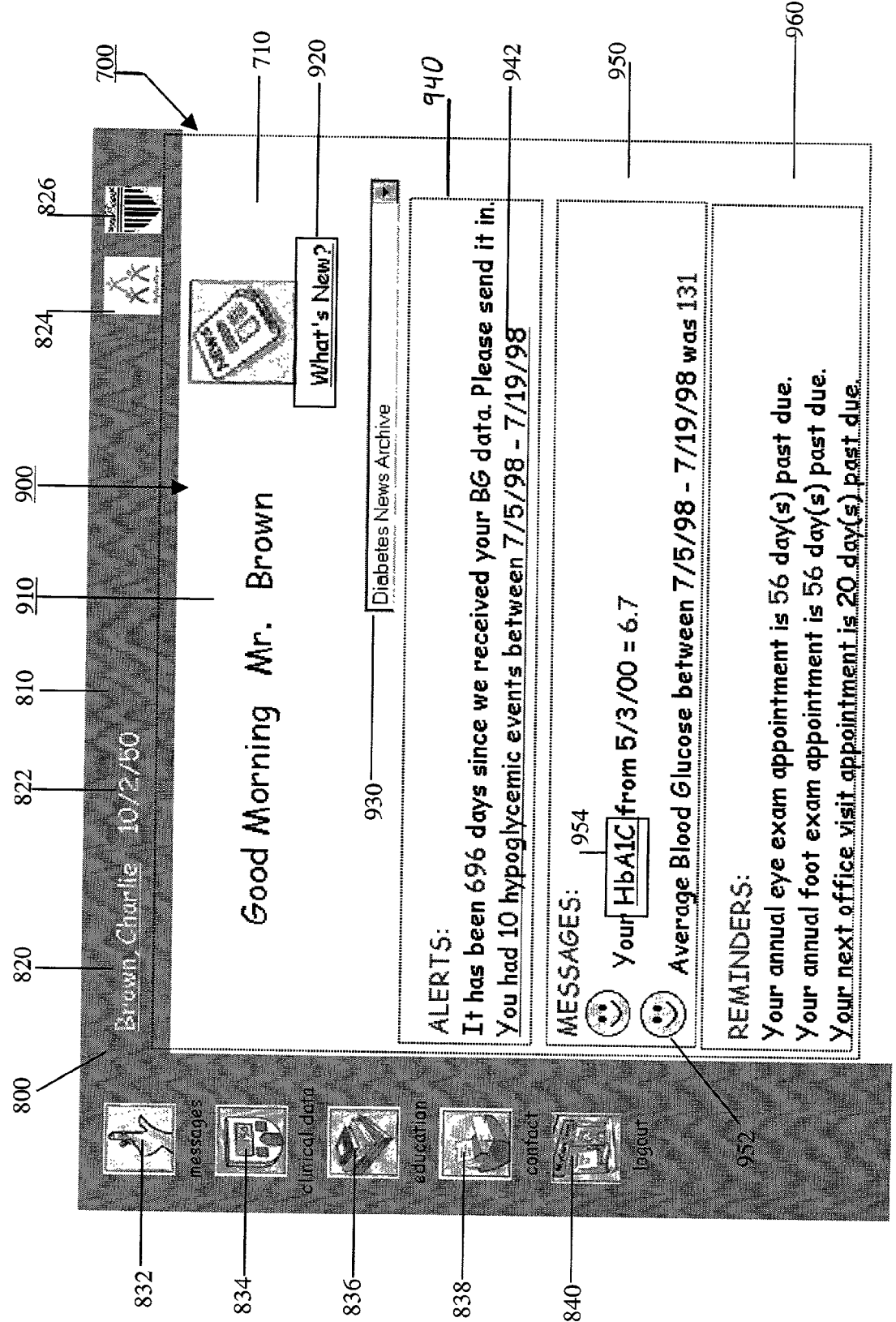
FIG. 10 shows a first exemplary embodiment of a main patient data screen of a graphical user interface according to this invention for a patient having diabetes.
Figure 32:
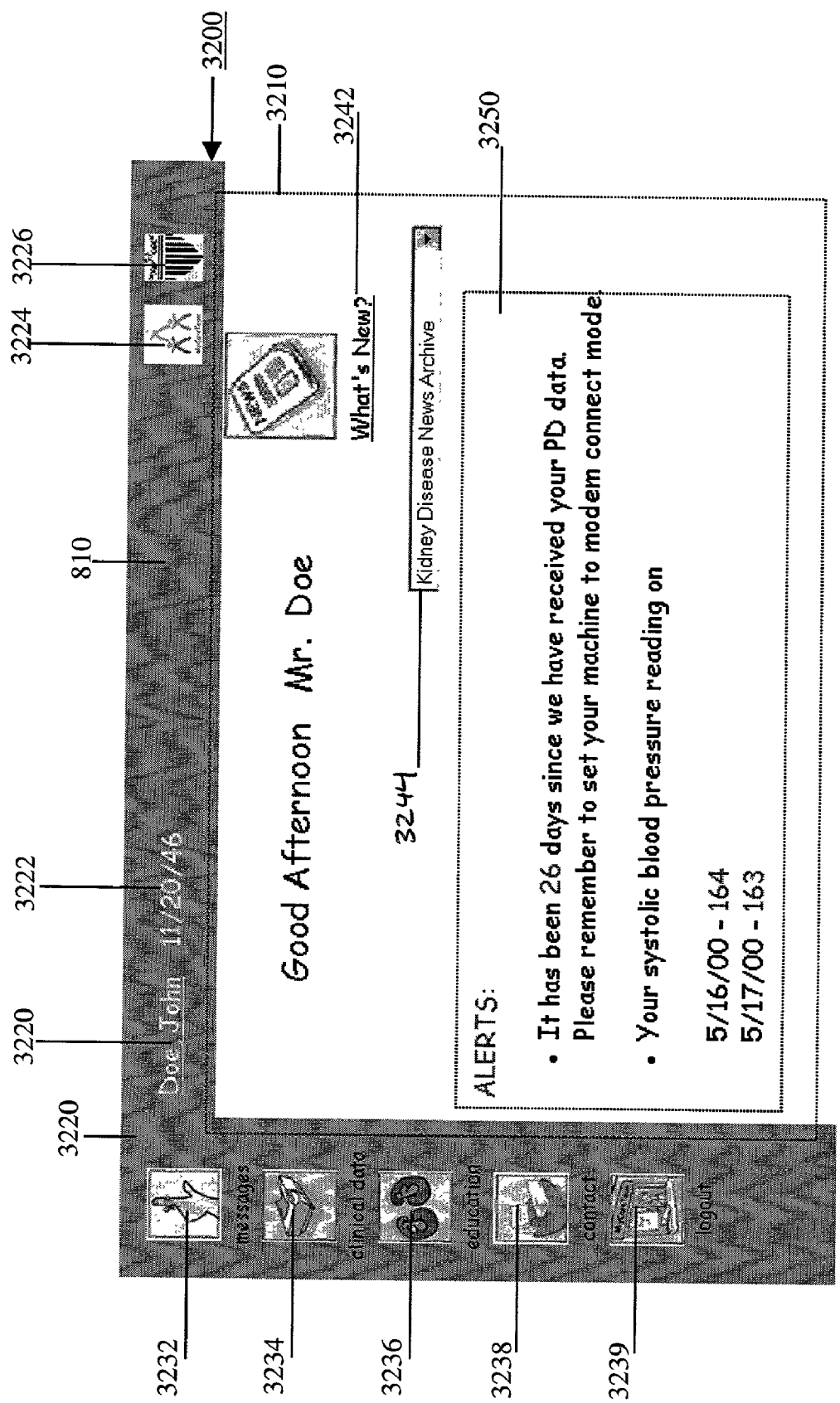
FIG. 32 shows a second exemplary embodiment of the main patient data screen of the graphical user interface according to this invention for a patient having a chronic kidney illness.

As shown in FIG. 9, in various exemplary embodiments, in response to the user indicating or activating the second floor elevator button 612, such as, for example, by putting the cursor over the second floor elevator button icon 612, an animation of the elevator door 620 opening onto a graphical representation of the kidney disease clinic 630 is displayed. Once the elevator door 620 is shown in the fully open position and the user selects the second floor elevator button icon 612, the screen 600 is replaced with the particular exemplary embodiment of a main patient data screen that is appropriate for the kidney clinic portion of the chronic illness management system, i.e., the kidney clinic main patient data screen 3200, as shown in FIG. 32. Similarly, in various exemplary embodiments, in response to the user indicating or activating the third floor elevator button 614, such, for example, by putting the cursor over the elevator button icon 614, an animation of the elevator door 620 opening onto a graphical representation of the diabetes clinic is displayed. Again, once the elevator door 620 is shown in the fully open position and the user selects the third floor elevator button icon 614, the screen 600 is replaced with the graphical user interface screen 700, as shown in FIG. 10. It should be appreciated that the number of clinics and the number of clinic floors accessed by the elevator 602 will depend upon the number of distinct chronic illnesses managed by the chronic illness management system 100.

Alternatively, the animation of the elevator door 620 opening can occur in response to the user selecting one of the elevator floor button icons 612-616. In this case, after the elevator door 620 reaches the fully open state, the screen 600 is immediately replaced with the screen of the graphical user interface that is associated with the selected elevator floor button 612-616.

The patient suffering from multiple chronic illnesses may also return to the clinic lobby 402 after visiting a particular clinic by selecting the lobby elevator button icon 616. In response to the user indicating or activating the lobby floor elevator floor button icon 616, such as for example, by putting the cursor over the lobby elevator button icon 616, the elevator door 620 is, in various exemplary embodiments, animated to show the elevator 602 opening onto the graphical representation of the clinic lobby floor. After the elevator door 620 opens onto a graphical depiction of the clinic lobby floor and the user selects the lobby floor elevator button icon 616, the screen 600 is automatically replaced with the screen 400 shown in FIG. 4. This graphical representation of elevator movement between floors to reach various clinics again mimics the experience the patient would expect to undergo during an actual clinic visit.

As shown in FIG. 10, after an authorized patient signs into the clinic system 200 using the screen 500, and depending on whether the elevator paradigm underlying the screen 600 is used to select a particular clinic for one of a number of chronic illnesses experienced by the patient, the screen 500 or the screen 600 is replaced with a main patient data screen 700. In the particular exemplary embodiment shown in FIG. 10, a patient suffering from diabetes has accessed the main patient data screen 700. Thus, the particular content of the main patient data screen 700 shown in FIG. 7 is that for a patient suffering from diabetes.

Of course, it should be appreciated that the particular contents of the main patient data screen 700 will depend on the particular chronic illness that the patient who has accessed the main data screen 700 is suffering from and may also depend upon whether the patient has used the elevator control panel 610 to select from multiple chronic illnesses. However, it should be appreciated that, in various exemplary embodiments of the chronic illness management system 100 according to this invention, the various main patient data screens, such as the screens 700 and 3200, maintain a consistent look and feel for the various icons, data portions and other elements, other than disease-specific data, between the various chronic illnesses that may be managed using the chronic illness management system 100.

In particular, it should be appreciated that the main patient data screen, such as the screens 700 and 3200, is the initial screen shown to patients after the patients sign into any one of the one or more different disease-specific clinics that may be implemented in the chronic illness management system 100. In various exemplary embodiments, to maintain the consistent look and feel between such different chronic illness clinics, the main patient data screen 700 includes, for example, a frame 800 and a central display area 710. To maintain the consistent look and feel of the main patient data screen 700, the frame 800 and the central display area 710 are maintained in consistent locations, shapes and relative proportions. In various exemplary embodiments, the frame 800 is displayed above and to the left of the central display area 710. However, it should be appreciated that the frame 800 can be positioned in any desired location within the main patient data screen 700.

However, because a consistent look and feel for the main patient data screen is maintained regardless of the particular chronic illness clinic that is being accessed, it is possible that a patient suffering from multiple chronic illnesses could have difficulty remembering which particular chronic illness is currently being accessed. Accordingly, in various exemplary embodiments, to help identify which particular chronic illness clinic is being accessed through the main patient data screen, such as the screens 700 or 3200, the background 810 of the frame 800 or of a frame 3202 of the screen 3200, can be color coded based on the particular chronic illness clinic that the user is visiting using the main patient data screen 700. For example, the background 810 for the diabetes clinic main data screen 700 could be blue, while the background 810 for the frame 3202 of the kidney disease clinic main data screen 3200 could be green. Thus, any graphical user interface screen having a frame 800 having a blue background 810 has been accessed through the diabetes clinic portion of the clinic system 200 and/or is displaying diabetes-related data, clinical information, and/or educational information.

In various exemplary embodiments, the frame 800 may include, for example, a selectable icon or hypertext link 820 displaying the user's name, a date indicator 822, a selectable icon or hypertext link 824 that is linked to another screen of the graphical user interface, and a selectable icon or hypertext link 826 that is linked to a website for a sponsor of the clinic system 200, such as a university that is associated with the virtual clinic. In various exemplary embodiments, the frame 800 may also include, for example, a selectable messages icon or hypertext link 832, a selectable clinical data icon or hypertext link 834, a selectable education icon or hypertext link 836, a selectable contact icon or hypertext link 838 and/or a selectable logout icon or hypertext link 840. Each of the selectable icons or hypertext links 832-840 is usable to change the information displayed in the central display area 710 of the main patient data screen 700.

As indicated above, each of the elements 832-840 can be a selectable icon or a hypertext link. To simplify the following detailed description, the term icon will be used interchangeably with the terms selectable icon and hypertext link.

Figure 29:
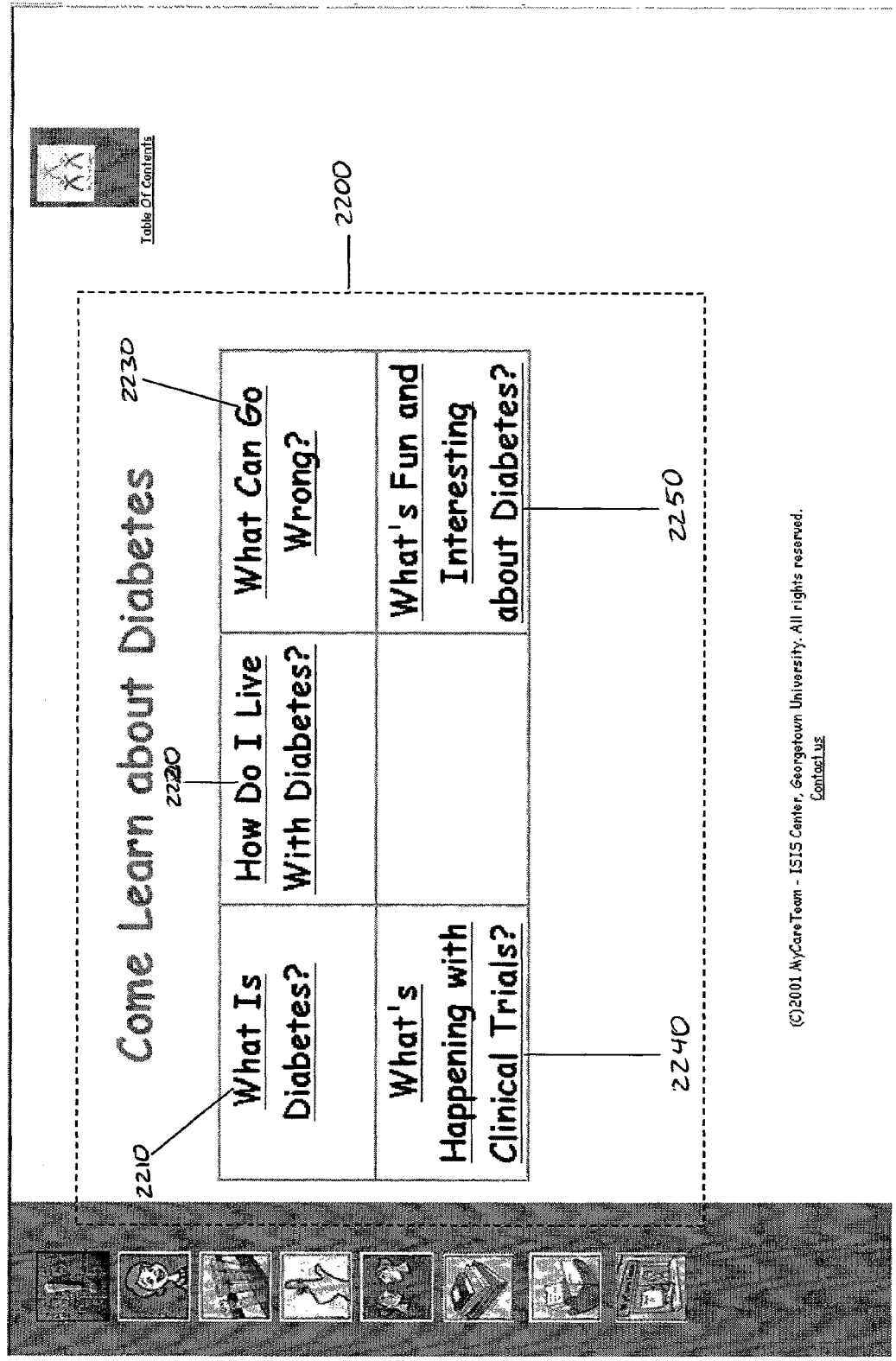
FIG. 29 shows one exemplary embodiment of a screen of a graphical user interface displaying educational information according to this invention.

In response to selecting the messages icon 832 of the frame 800, a messages screen 900 is displayed in the central display area 710 of the main patient data screen 700. In contrast, selecting the clinical data icon 834 causes various types of clinical information and clinical data to be presented to the patient in the central display area 710 of the main patient data screen 700 using the screens 1500-2100 and 6800. In response to selecting the education icon 836, the diabetes education screen 2200 shown in FIG. 29 is displayed in the central display area 710 of the main patient data screen 700.

Figure 31:
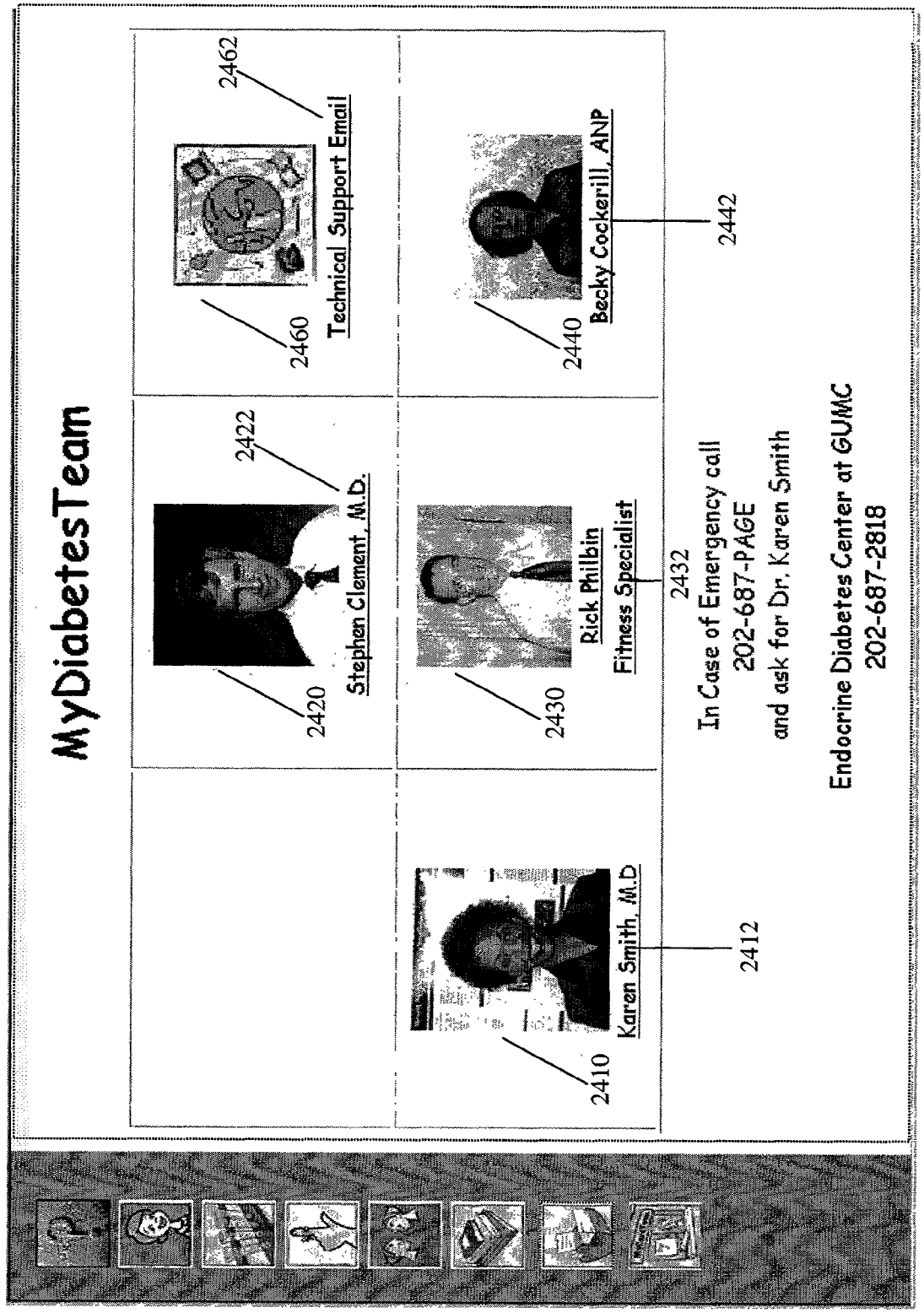
FIG. 31 shows one exemplary embodiment of a screen of a graphical user interface displaying a contacts page according to this invention.

Selecting the contact icon 838 causes one of a number of contact screens to be displayed, such as the diabetes contact screen 2400 shown in FIG. 31 or a contact screen for the kidney clinic. It should be appreciated that the particular contact screen accessed using the contact icon 838 will depend on a particular chronic illness clinic that the patient is currently visiting. Finally, selecting the logout icon 840 logs the patient out of the currently selected chronic illness clinic and displays the clinic lobby screen 400 or the elevator screen 600, depending on whether the patient has one or more chronic illnesses, in place of the main patient data screen 700.

As shown in FIG. 10, in various exemplary embodiments, when the main patient data screen 700 is first displayed during any given session, the messages screen 900 is also automatically displayed in the central display area 710. The messages screen 900 includes a patient greeting 910, appropriately addressed and based on the time of day (i.e., "Good Morning," "Good Afternoon," or "Good Evening") followed by the patient's name, a selectable icon or hypertext link 920 to a screen that displays the latest news, a dropdown list 930 that allows the patient to access archived news items on various subjects, and alerts portion 940, a messages portion 950 and a reminders portion 960.

In various exemplary embodiments, the information presented to the patient concerning the alert portions 940, the messages portion 950 and/or the reminders portion 960 of the messages screen 900 is automatically extracted or derived from the data stored in the relational database 232 when the patient initially accesses the main patient data screen 700 by analyzing the data stored in the relational database 232 in real time. The information presented to the patient in the alerts portion 940, the messages 950 and/or the reminders portion 960 of the message screen 900 is the type of information that a healthcare practitioner or other healthcare practitioner would emphasize to a patient during an actual clinic visit.

When the amount of information to be displayed in any one of the alerts portion 940, the messages portion 950 or the reminders portion 960, or in total in the messages screen 900, exceeds the size of the central display area 710, a vertical and/or horizontal scroll bar (not shown), as is well known in the art, can be implemented to allow the patient to view any information that could not initially be displayed in the central display area 710. Of course, it should be appreciated that this technique will be usable for all of the following screens that can be displayed in the central display area 710. Thus, use of scroll bars will not be further described.

As shown in FIG. 10, the alerts portion 940, the messages portion 950 and/or the reminders portion 960 of the messages screen 900 may contain medical terms that have embedded hypertext links or graphical user interface widgets, such as the hypertext link or graphical user interface widget 954 shown in FIG. 10. These hypertext links or graphical user interface widgets allow the patient to access additional screens, separate windows, and/or windows elements of the graphical user interface that provide information about such medical terms.

Figure 11:
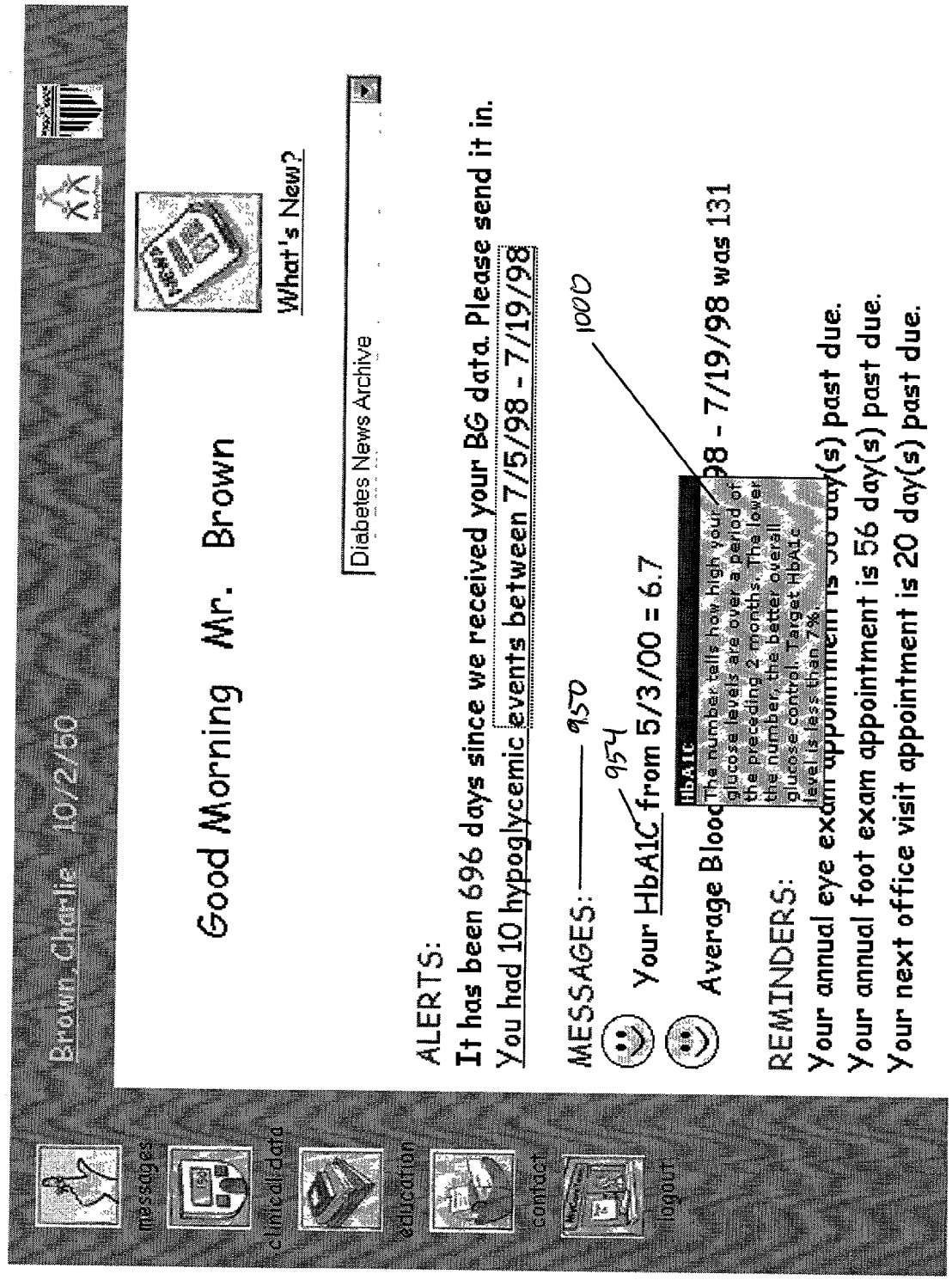
FIG. 11 shows one exemplary embodiment of an on-screen contextually relevant message displayed over information displayed on the main patient data screen of FIG. 10.

Thus, as shown in FIG. 11, when the patient selects or hovers over or otherwise indicates the hypertext link or graphical user interface widget associated with such a medical term, such as the graphical user interface widget or hypertext link 954 associated with the medical term "HbA1C" in FIG. 10, contextually relevant information 1000 may be displayed, for example, in a pop-up dialog box 1000. The information contained within the pop-up dialog box 1000 defines and/or further explains the medical term, symbol or icon associated with the selected or indicated hypertext link or graphical user interface widget. Alternatively, rather than using the pop-up dialog box 1000, selecting and/or indicating the hypertext link or graphical user interface widget could result in a glossary screen (not shown) being displayed.

As shown in FIG. 11, in various exemplary embodiments that use the pop-up dialog box 1000, selecting or indicating the graphical user interface widget or hypertext link 954 associated with the medical term "HbA1C" in the messages portion 950 results in the pop-up dialog box 1000 being displayed and containing a contextually relevant message providing a definition for this medical term. Similarly, in various exemplary embodiments, hovering over or indicating, but not selecting, the education icon 836 of FIG. 10 also causes a contextually relevant message (not shown) to be displayed that may further characterize the education icon 836 as "a diabetes educational site".

The messages portion 950 can also optionally include a hypertext link or graphical user interface widget (not shown) that allows a patient to provide comments when the patient has entered new clinical data, such as blood glucose values, into the clinic system 200. In this case, selecting the hypertext link or graphical user interface widget associated with the newly entered clinical data, such as, for a diabetes patient, blood glucose levels, results, in various exemplary embodiments, in a text entry box (not shown) being displayed to the patient. Alternately, in various other exemplary embodiments, this results in the message screen 900 being replaced with a clinical data comments screen (not shown). In either case, in response to selecting the hypertext link or graphical user interface widget associated with the new clinical data, the patient is able to enter comments about the new clinical data from that patient's data terminal 120.

Figure 12:
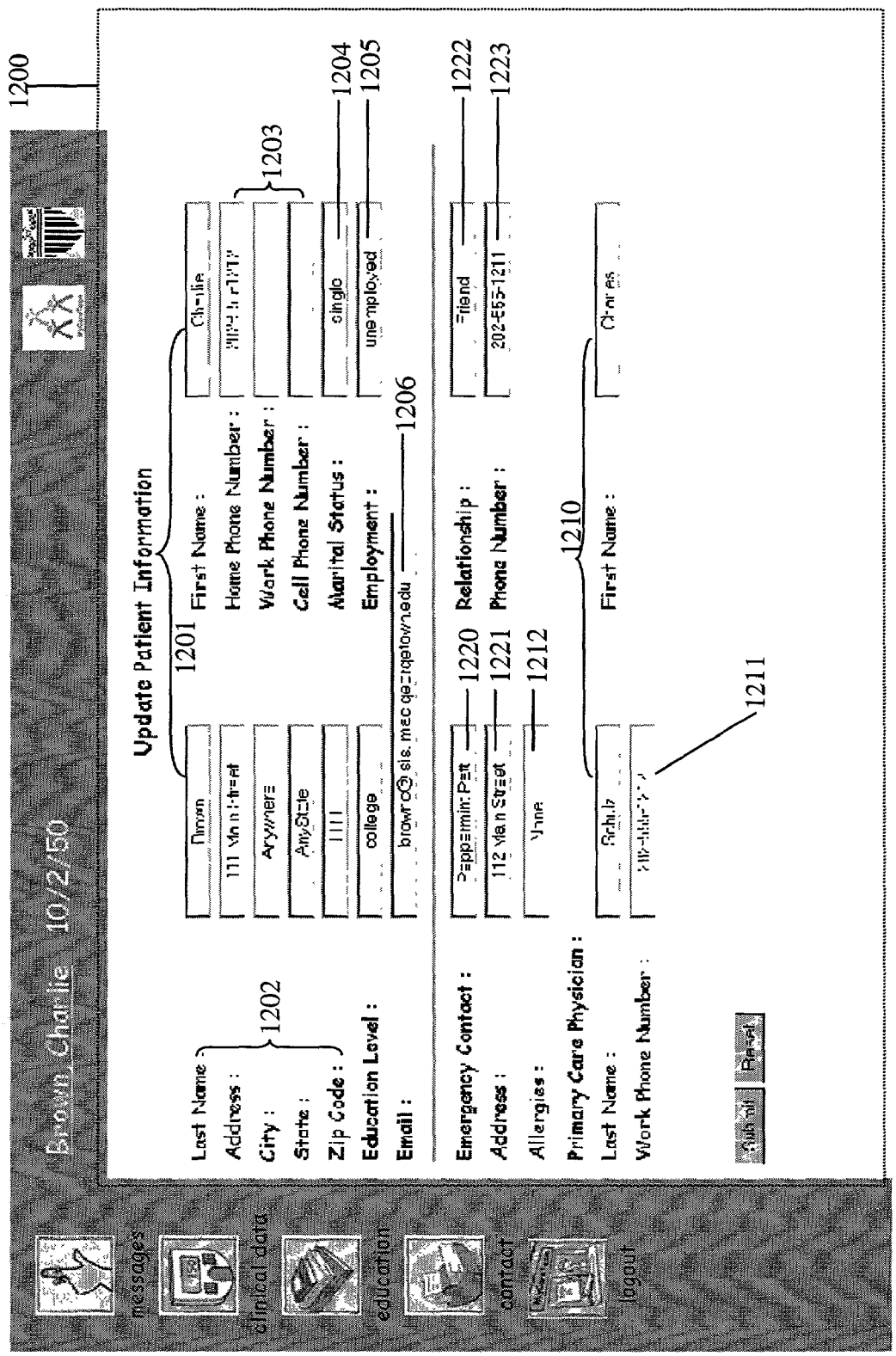
FIG. 12 shows one exemplary embodiment of an update patient information form screen according to this invention.

As shown in FIG. 12, when the patient selects the patient's name icon 820 in the frame 800, the main patient data screen 700 is replaced with an update patient information screen 1200. The update patient information screen 1200 may include a number of data entry boxes 1201-1206 usable, for example, to update the patient's personal information, such as the patient's name, address, telephone numbers, marital status, employment, and/or e-mail or message address. The update patient information screen 1200 can also include a number of data entry boxes 1210-1212 usable to update the patient's medical information, such as the name and/or telephone number of that patient's primary care healthcare practitioner, and/or that patient's allergies. Finally, the update patient information screen 1200 can include a number of data entry boxes 1220-1223 usable to update the patient's emergency information such as the name, address, relationship and/or telephone number of that patient's emergency contact.

As shown in FIG. 13, in response to the patient selecting the hypertext link or graphical user interface widget 920, the messages screen 900 displayed in the central data area 710 of the main patient data screen 700 is replaced with a news screen 100. The news screen 1100 displays one or more recent news articles that are relevant to the particular chronic illness that the patient was managing at the time the hypertext link or graphical user interface widget 920 was selected. As described above with respect to the messages screen 900, when the news article displayed in the news screen 1100 exceeds the size of the central display area 710, the entire news article may be viewed by using vertical and/or horizontal scroll bars (not shown). Using the archives news dropdown list box 930 allows archival news to be selected for display in the news screen 1100.

As shown in FIG. 10, the alerts portion 940 of the messages screen 900 displays information to the patient that is derived from the clinical data supplied, or often, not supplied, by the patient to the clinic system 200 over the patient's data terminal 120 and the network 110. For a diabetic patient, the information displayed in the alerts portion 940 is derived from an automated, real-time analysis by the clinic system 200 of the measured blood glucose values that the patient has sent to the clinic system 200 and which has been stored in the relational database 232. The alerts portion 940 summarizes those events, and activities and/or inactivities, which may be detrimental to the patient.

Figure 14:
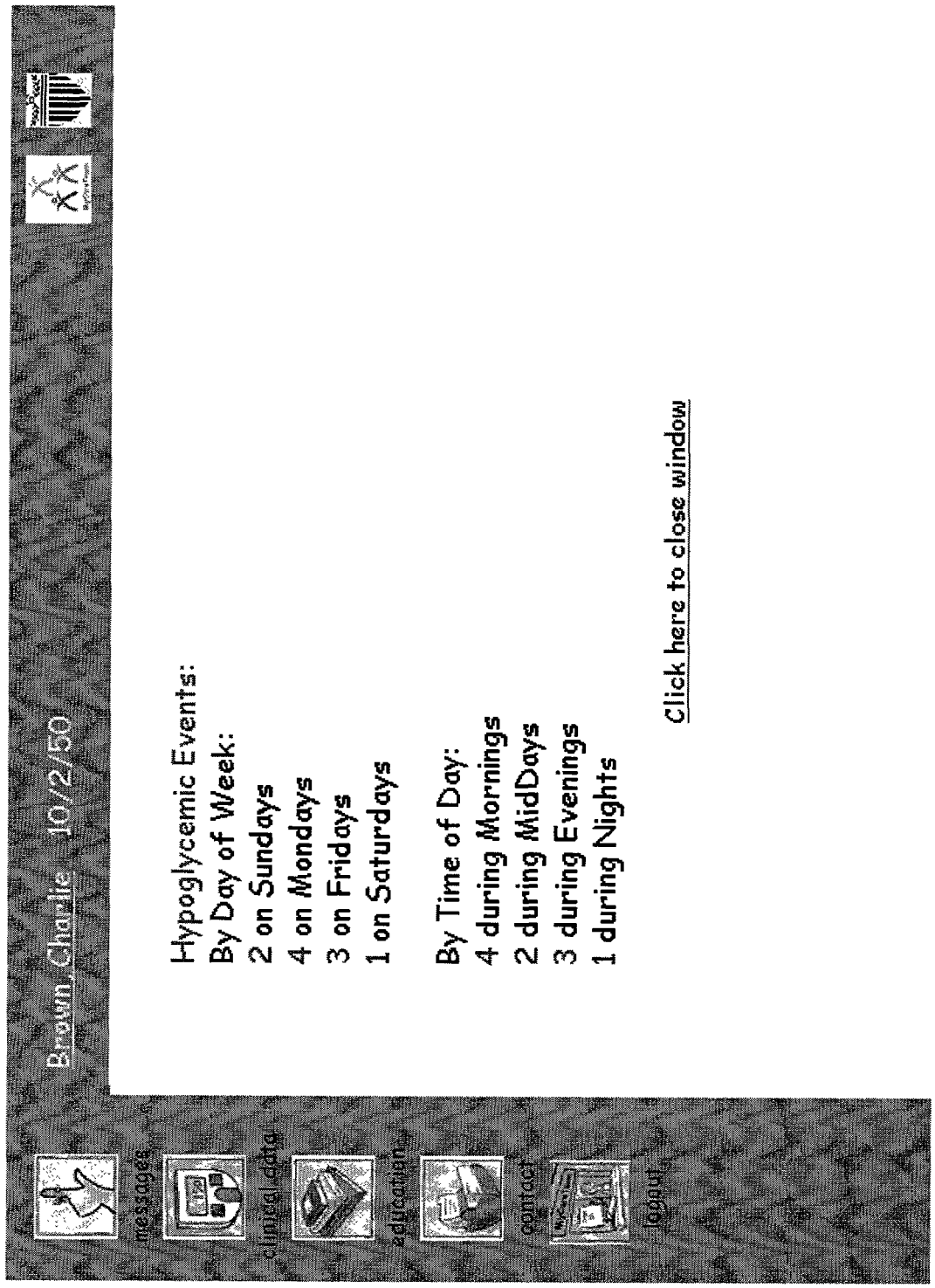
FIG. 14 shows one exemplary embodiment of a screen of a graphical user interface usable to display a tabular representation of hypoglycemic and/or hyperglycemic events according to this invention.

Data is analyzed by the clinic system 200 to inform patients, using the alerts portion 940, about various clinical parameters that have reached an indicated alert level. In the data illustrated in the exemplary embodiment shown in FIG. 10, the latest HbA1C value is greater than the site/patient configurable value. As a result, the value of the patient's latest HbA1C value is printed in red and an appropriate message is attached and displayed in the alerts portion 940. Similarly, if the patient's Average Blood Glucose value over the last 2 weeks is greater than the site/patient configurable value, the patient's Average Blood Glucose value is printed in red and an appropriate message is attached and displayed in the alerts portion 940. If the number of hypoglycemic events and/or hyperglycemic events exceeds the corresponding site/patient configurable value, then the stored clinical data is analyzed to show when these hypoglycemic and/or hyperglycemic events occurred. As shown in FIG. 14, these hypoglycemic events and/or hyperglycemic can be organized by the day of week in the table portion or tabular chart 1410 and/or by the time of day in a table portion or tabular chart 1412 of an events screen 1400. Similarly, if more than a site/configurable time period has past since receiving new blood glucose data, then the number of days is printed in red and a message is attached and displayed in the alerts portion 940.

Additionally, in the data illustrated in the exemplary embodiment shown in FIG. 10, data is analyzed to inform a patient about positive results in the patient's data in the messages portion 950. If the patient's Average Blood Glucose value over the previous two weeks is less than site/patient configurable value, then that value is printed in green, with a smiley face 952 and message attached and displayed in the messages portion 950. If the patient's latest HbA1C value is less than site/patient configurable value and has decreased by a site/patient configurable amount, then that value is printed in green, with a smiley face 952 and message attached and displayed in the messages portion 950. Finally, if a patient has sent new blood glucose data without attaching a comment, the patient is prompted to do so at that time by displaying an appropriate message in the messages portion 950. Of course, it should be appreciated that the particular alerts and messages displayed in the alerts portion 940 and the messages portion 950 will depend on the particular chronic illness the patient is suffering from In the exemplary embodiment illustrated by the data shown in FIG. 10, the clinic system 200 has analyzed the blood glucose values submitted by the patient and has determined from the clinical data and/or other information stored in the relational database 232 that this patient has not reported blood glucose data (BG data) in 696 days. In performing its analysis, the clinic system 200 compares the number of days for which blood glucose values were not reported to a threshold value. When this threshold value is exceeded, the clinic system 200 causes an appropriate alert message to be displayed in the alerts portion 940. The number of days a blood glucose value has not been received may also be emphasized to the patient by color coding the number of days, in this case 696, displayed in the alerts portion 940, depending on the urgency and/or importance of the message.

In the exemplary embodiment illustrated by the data shown in FIG. 10, the clinic system 200 also summarizes the number of hypoglycemic and hyperglycemic events present in the information and clinical data stored in the relational database 232. The clinic system 200 causes the generated summary information to be displayed in the alerts portion 940 as well. The clinic system 200 determines these types of events by comparing the clinical data stored in the relational database 232 to one or more threshold values. The threshold values have been entered into the clinic system 200 by a healthcare practitioner via one of the healthcare practitioner data terminals 130. Each event, or each set of events, is associated with a hypertext link or a graphical user interface widget, as shown in the alerts portion 940.

When the patient selects the hypertext link or graphical user interface associated with such an event listed in the alerts portion 940, the messages screen 900 displayed in the central data portion 710 is replaced with the events screen 1400 shown in FIG. 14. As shown in FIG. 14, the events screen 1400 shows various organizations of the events associated with the selected hypertext link or graphical user interface widget. For example, when the hypertext link or graphical user interface widget 942 regarding hypoglycemic and/or hyperglycemic events shown in FIG. 10 is selected, the events screen 1400 shows various hypoglycemic and/or hyperglycemic events associated with that hypertext link or graphical user interface widget organized by day of week in a first tabular chart 1410 and by time of day in a second tabular chart 1412.

The information displayed in the messages portion 950 may also be provided by the clinic system 200. The messages that may be displayed in the messages portion 950 include, for example, that HbA1C and/or average blood glucose are in target. The real-time analysis by the clinic system 200 of the patient's blood glucose values that are stored in the relational database 232, when compared to a clinical target range, provides information about the number of times the patient's blood glucose values either fall below or exceed the normal range. Based on the number of times the patient's blood glucose values are not normal, the messages displayed in the messages portion may indicate whether the patient is properly managing his or her diabetes. For example, good management of the patient's diabetes may be indicated by animated yellow smiling faces 952, while poor management may be indicated by blue frowning faces (not shown). A green blood glucose value or clinical test value in a message may indicate a normal value, indicating good clinical management of the diabetes. Messages are the type of information that a clinician is likely to emphasize to a patient during a clinical visit.

In FIG. 10, the patient's healthcare practitioners have entered reminders to the patient, for medical tests, exams and visits, into the clinic system 200. These reminders are stored in the relational database 232. Data is mined to determine and/or generate reminders of lab tests, clinic visits, etc. for the patient. These reminders are then displayed in the reminders portion 960. The status of the reminders, such as, whether the patient has properly responded to the reminder, can be color-coded. In various exemplary embodiments, such as that shown in FIG. 10, a patient is prompted, at a site/patient configurable time prior to the event, to schedule an appointment. For example, the days past due for an appointment to have been scheduled, or a missed appointment, may be emphasized by setting the appearance of some or all of that text string to red. In the exemplary embodiment shown in FIG. 10, the number of days the appointment is past due is displayed in red.

Selecting the clinical data icon 834 when accessing the diabetes clinic changes the information displayed in the central display area 710 to one of a set of interlinked clinical data screens 1500-2100 and a message list screen 6800. In particular, in the exemplary embodiments shown in FIG. 15, the clinical data screen initially displayed upon selecting the clinical data icon 834 is a patient supplied data screen 1500. However, it should be appreciated that any of the clinical data screens 1500-2100 or the messages list screen 6800 could be initially displayed.

Figure 15:
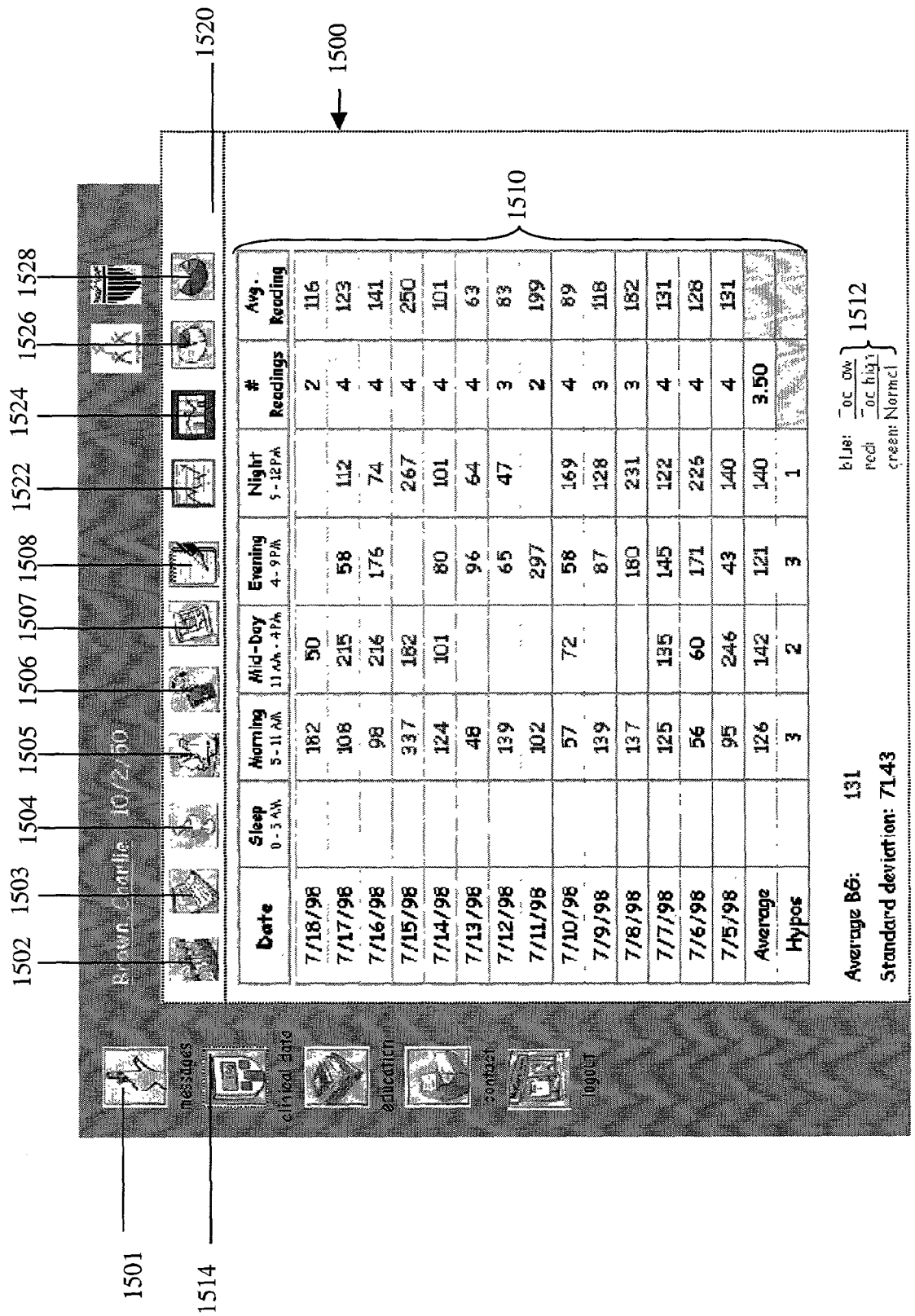
FIG. 15 shows one exemplary embodiment of a patient supplied data screen of a graphical user interface usable to display a blood sugar log according to this invention.

The patient supplied data screen 1500 displays the clinical data that has been submitted to the system by the patient using the medical device 122, such as, an automated or manual blood glucose meter. For a diabetic patient, the clinical data are the patient's blood glucose values, displayed as a blood sugar log 1510 in the patient supplied data screen 1500, as shown in FIG. 15. The blood sugar log 1510 is a chart with summary data. An explanatory legend 1512 is located beneath the chart, as shown in FIG. 15.

The patient supplied data screen 1500 also includes a tool bar 1520 that includes a number of icons usable to change the type of graphing used to display the patient supplied data and a tool bar 1501 that includes a number of icons usable to switch between the various clinical data screens 1500-2100 and 6800. It should be appreciated that the patient supplied data screen 1500 can also be accessed through the icon 1503 of the toolbar 1501.

The blood sugar log 1510 displays blood glucose (BG) values by date and time of day in the chart. A single row of the chart may display the date, blood glucose values at specific time intervals during the day, the number of blood glucose values obtained in a day (# Readings), and the average value of the blood glucose readings for the day (Avg. Reading). At the bottom of the blood sugar log 1510, the average values of blood glucose for a specific daily time interval and the average number of readings per time frame (not shown) may be displayed. Additional rows at the bottom of the chart may display the number of hypoglycemic events and hyperglycemic events (not shown) that occur in a specific daily time interval for the displayed dates.

In the blood sugar log 1510, a blood glucose value having an associated graphical user interface widget or hypertext link may indicate that more than one blood glucose reading was taken during a time interval. When multiple blood glucose readings occur within a time interval, only the first blood glucose value is displayed in the chart. However, when the graphical user interface widget or hypertext link associated with such a blood glucose value is selected, an on-screen contextual message (not shown) displays all the blood glucose values submitted during that interval.

Beneath the blood sugar log 1510, the average blood glucose value for all time intervals over the displayed dates is shown, along with a statistical standard deviation of all the blood glucose values and the range of blood glucose values, indicating maximum and minimum blood glucose values (not shown). Additionally, the legend 1512 beneath the blood sugar log 1510 explains the color coding of the blood glucose values in the chart, which may represent hypoglycemic values in blue, hyperglycemic values in red, and normal blood glucose values in green Hypoglycemic and hyperglycemic values may, alternatively, be displayed with an associated minus sign or plus sign, respectively.

In particular, in various exemplary embodiments of the systems and methods according to this invention, the values in the log book are color coded and/or are preceded by a + sign or a − sign, depending on their value. If the values in the log book arc greater than a site/patient configurable value, then the values are displayed in red and preceded by a +. If the values in the log book are less than a site/patient configurable value, the values are displayed in blue and preceded by a − If the values in the log book are greater than a site/patient minimum configurable value and less than a site/patient maximum configurable value, the values are displayed in green. Additionally, if multiple readings for a given day and a given time slot are available, the first reading for that day and time slot is displayed, but the other values arc available by moving the mouse over the first reading. In response, a pop-up window is displayed that includes some or all of the readings for that day and time slot.

Figure 16:
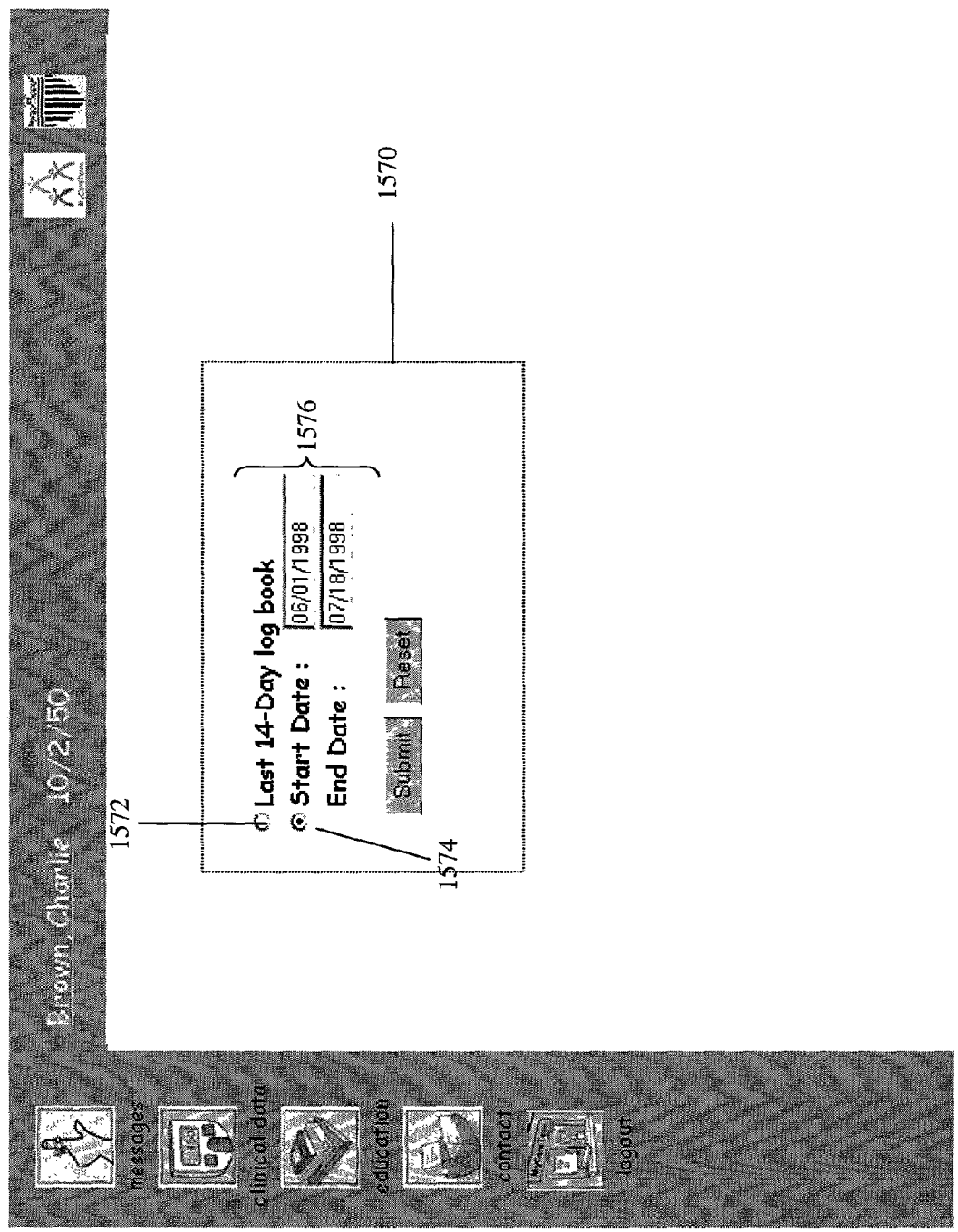
FIG. 16 shows one exemplary embodiment of a screen of a graphical user interface usable to display a date selection graphic according to this invention.

By selecting the date hypertext link or graphical user interface widget 1514 in the upper left corner of the blood sugar log 1510 of FIG. 15, the screen changes to that of a date interval selection screen or window 1570, as shown in FIG. 16. In the date interval selection screen or window 1570, the patient may select the dates for which the blood sugar log 1510 is to display blood glucose values. The patient may select either the last 14 days entered in the blood sugar log book by an option button 1572 or a "Start Date/End Date" option by selecting a second option button 1574. If the "Start Date/End Date" option is selected, the patient may enter the start and end dates into, for example, standard data entry input boxes 1576, as shown in FIG. 16.

Figure 17:
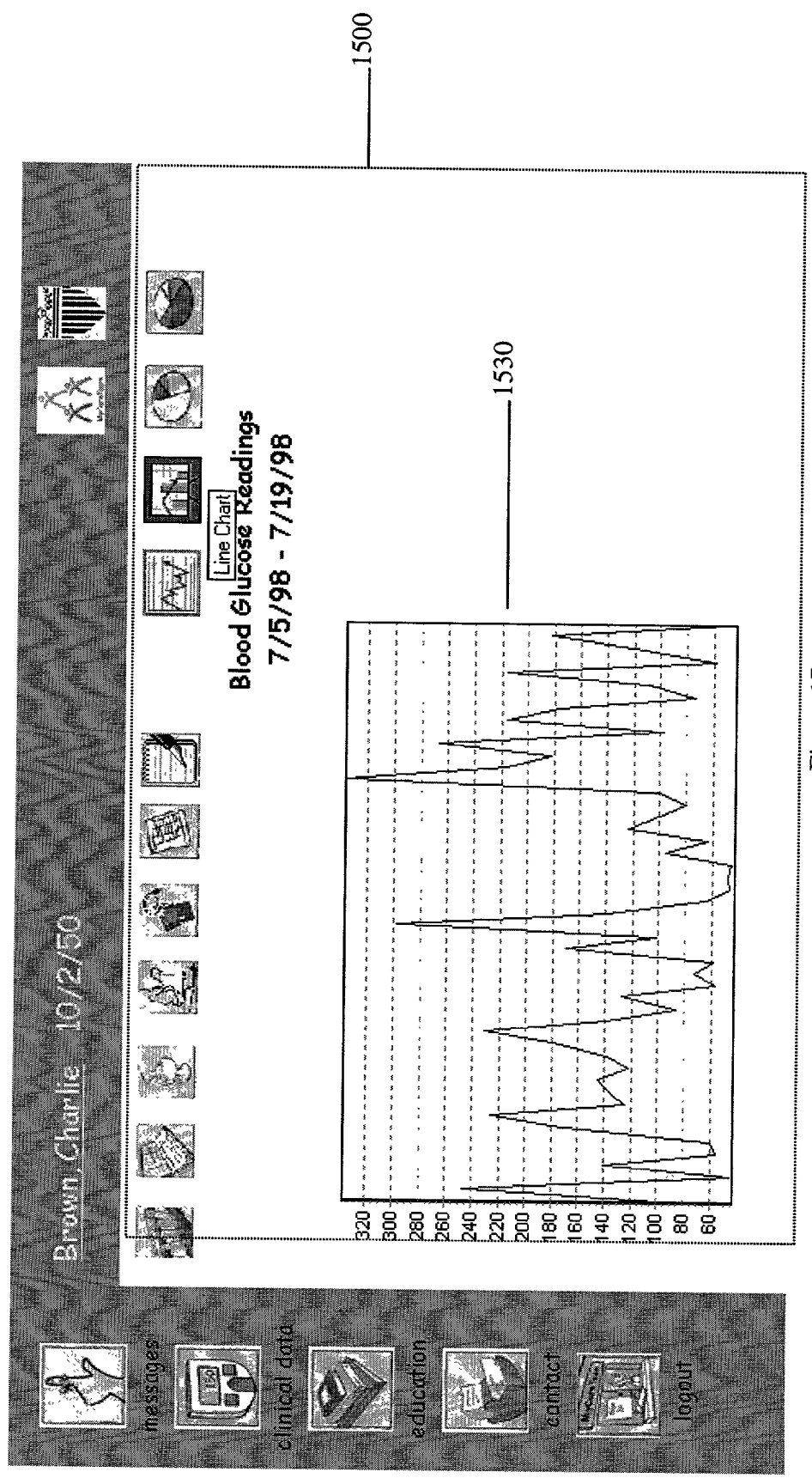
FIG. 17 shows one exemplary embodiment of a screen of a graphical user interface usable to display a linear graph according to this invention.
Figure 18:
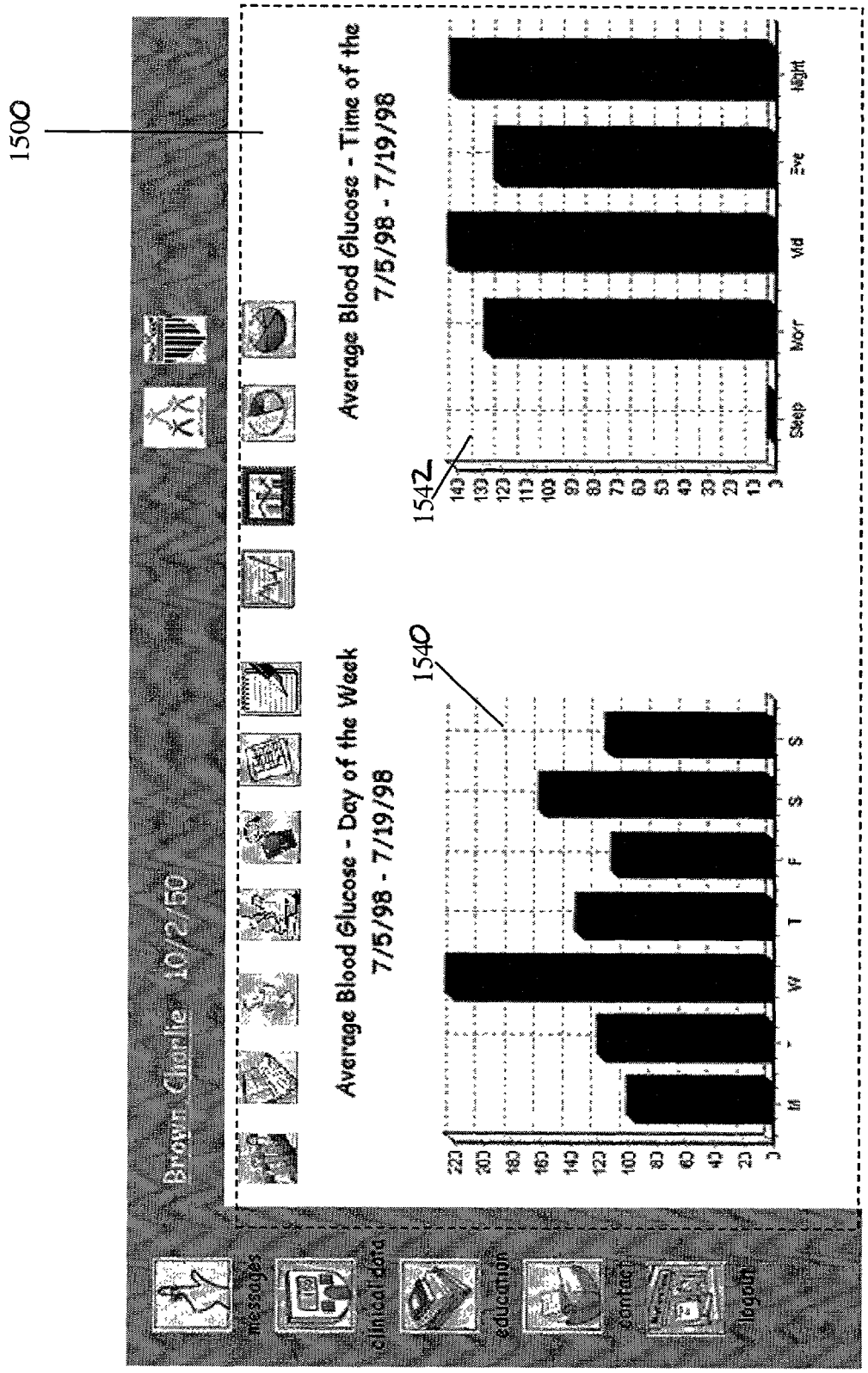
FIG. 18 shows one exemplary embodiment of a screen of a graphical user interface usable to display histograms according to this invention.

The graphing icons in the toolbar 1520 located on the clinical data screen 1500 may change the presentation of the blood sugar log 1510. For example, if the patient selects the animated line chart icon 1522, the tabular blood sugar log 1510 is replaced with a linearly plotted graph 1530, as shown in FIG. 17. This linearly plotted graph 1530 plots blood glucose values against time during the date interval that is displayed above the graph. Similarly, selecting the animated "Histograms" icon 1524 displays the data contained in the blood sugar log 1510 as two histograms 1540 and 1542, shown in FIG. 18. The first histogram 1540 plots blood glucose values against days of the week, and the second histogram 1542 plots blood glucose values against the daily time intervals.

Figure 19:
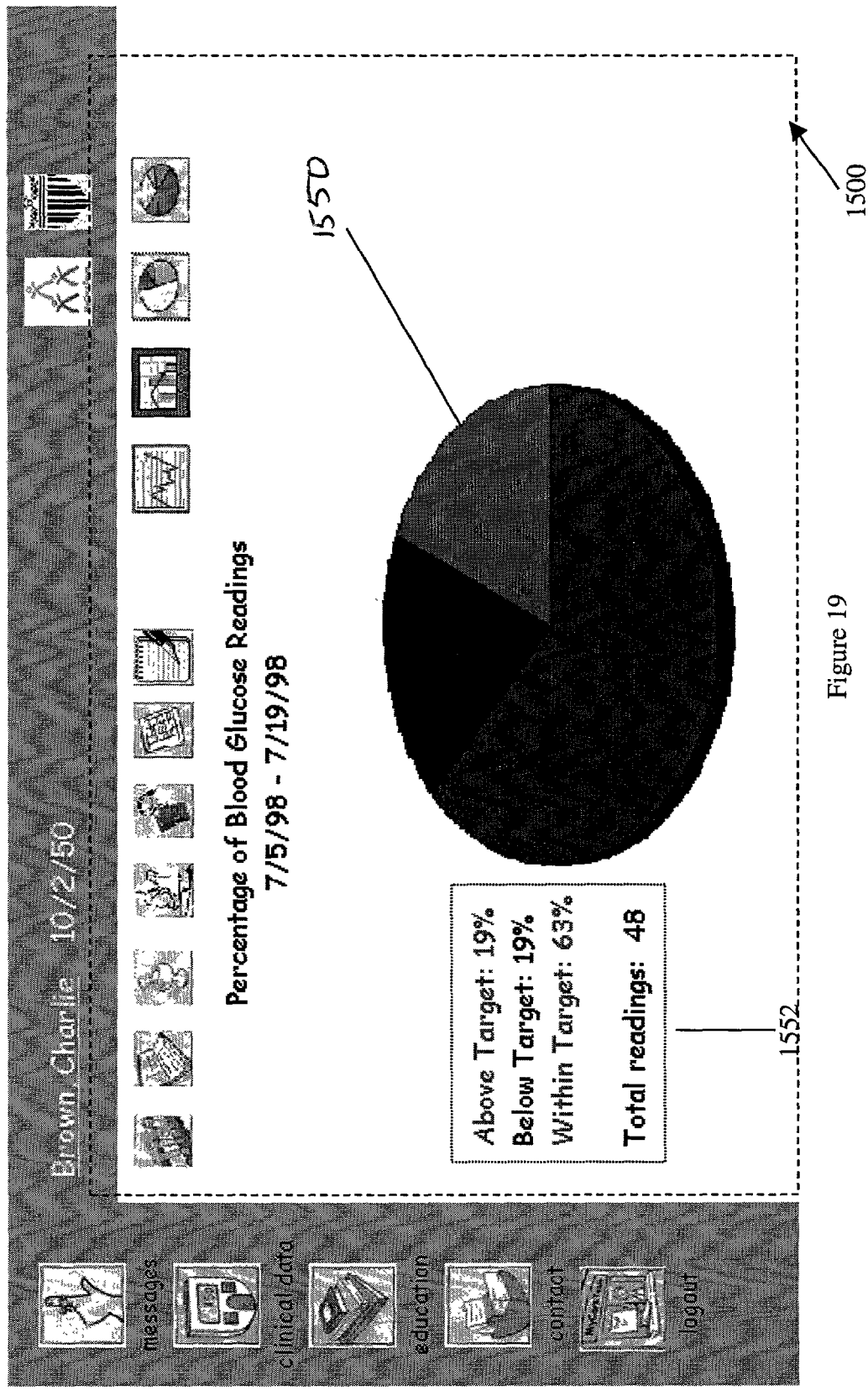
FIG. 19 shows one exemplary embodiment of a screen of a graphical user interface usable to display a pie chart according to this invention.

These different data presentations may help the patient to understand any daily or weekly patterns of changes in blood glucose values. Such patterns would usually be discussed in an actual clinic visit to explore activities surrounding the time during which such changes of blood glucose values occur, so as to avoid possible hypoglycemic or hyperglycemic events When the pie chart icon 1526 of FIG. 15 is selected, the data contained in the blood sugar log 1510 is shown as percentages of blood glucose readings above, below and within the target range of clinically desired blood glucose values in a pie chart 1550, as shown in FIG. 19. Sectors of the pie chart may also be color coded to reflect the percentage of blood glucose readings above, below and within a clinical target range as explained in the legend 1552. For example, a sector of the pie indicating the percentage of blood glucose readings that are above the target blood glucose range may be colored red, while those that are within the target range are colored green and those below the target range are colored blue. Alternatively, various shadings or graphics may be used to distinguish between the pie chart sectors.

Figure 20:
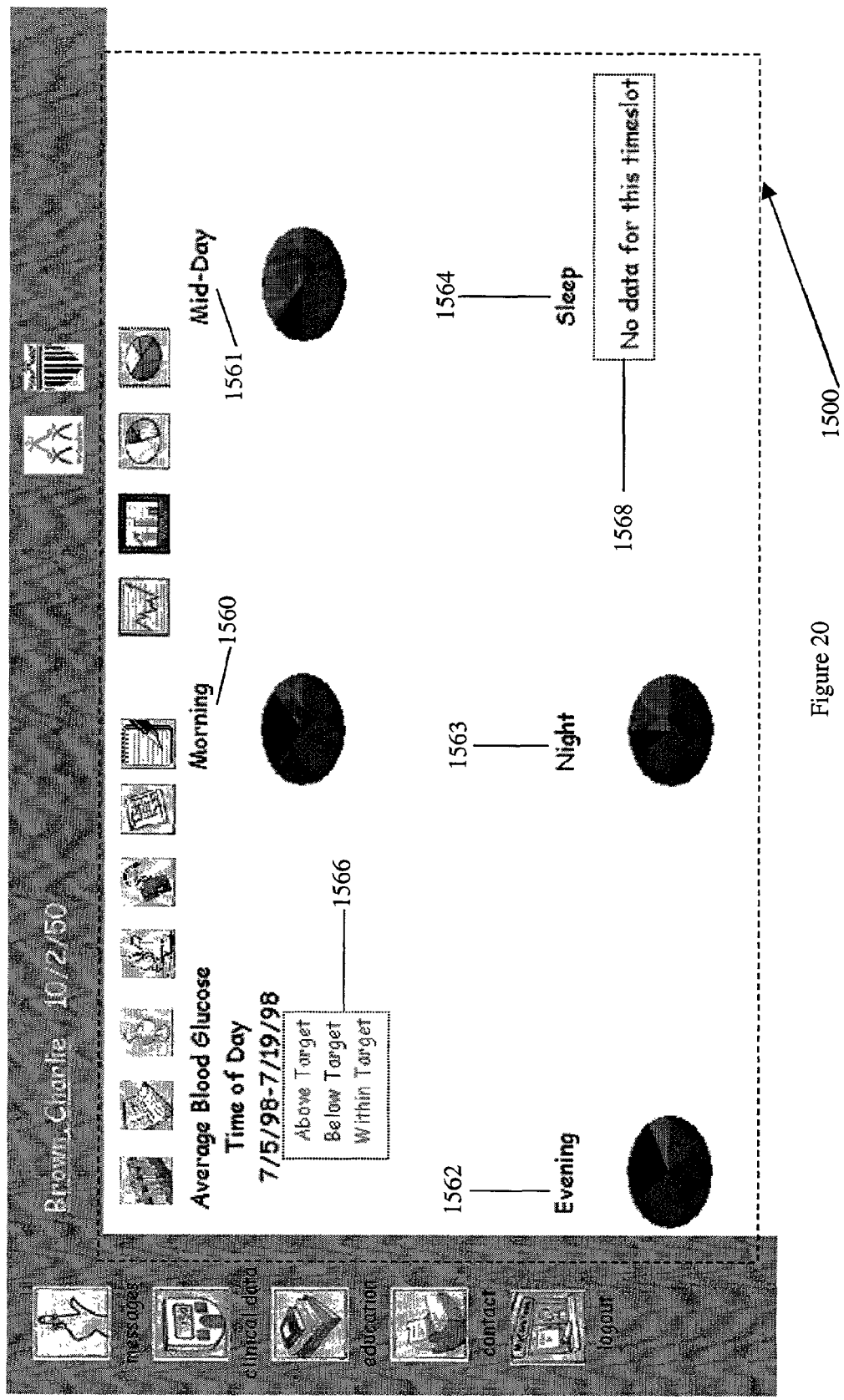
FIG. 20 shows one exemplary embodiment of a screen of a graphical user interface usable to display multiple pie charts according to this invention.

Selecting the multiple pie chart icon 1528 results in a pie chart 1560-1564 for each specific daily interval of the blood sugar log 1510, as shown in FIG. 20. each pie chart 1560-1564 indicates the percentage of blood glucose readings that were above, below or within the target blood glucose range for a particular time interval. Again, sectors of each pie may be color coded to reflect the percentage of blood glucose readings above, below and within a clinical target range as explained in the color-coded legend 1566, or indicated by pluses or minuses (not shown). When no blood glucose readings correspond to a particular daily time interval, a message 1568, for example, "No data for this timeslot", may be presented, as shown in FIG. 20. The line charts 1530 shown in FIG. 17, the histograms 1540 and 1542 shown in FIG. 18, and the pie charts shown in FIGS. 19 and 20 are tied to the data range and the data displayed in the blood sugar log 1510. If the date range is changed in the log book, then the date range on the graphs also changes.

Figure 21:
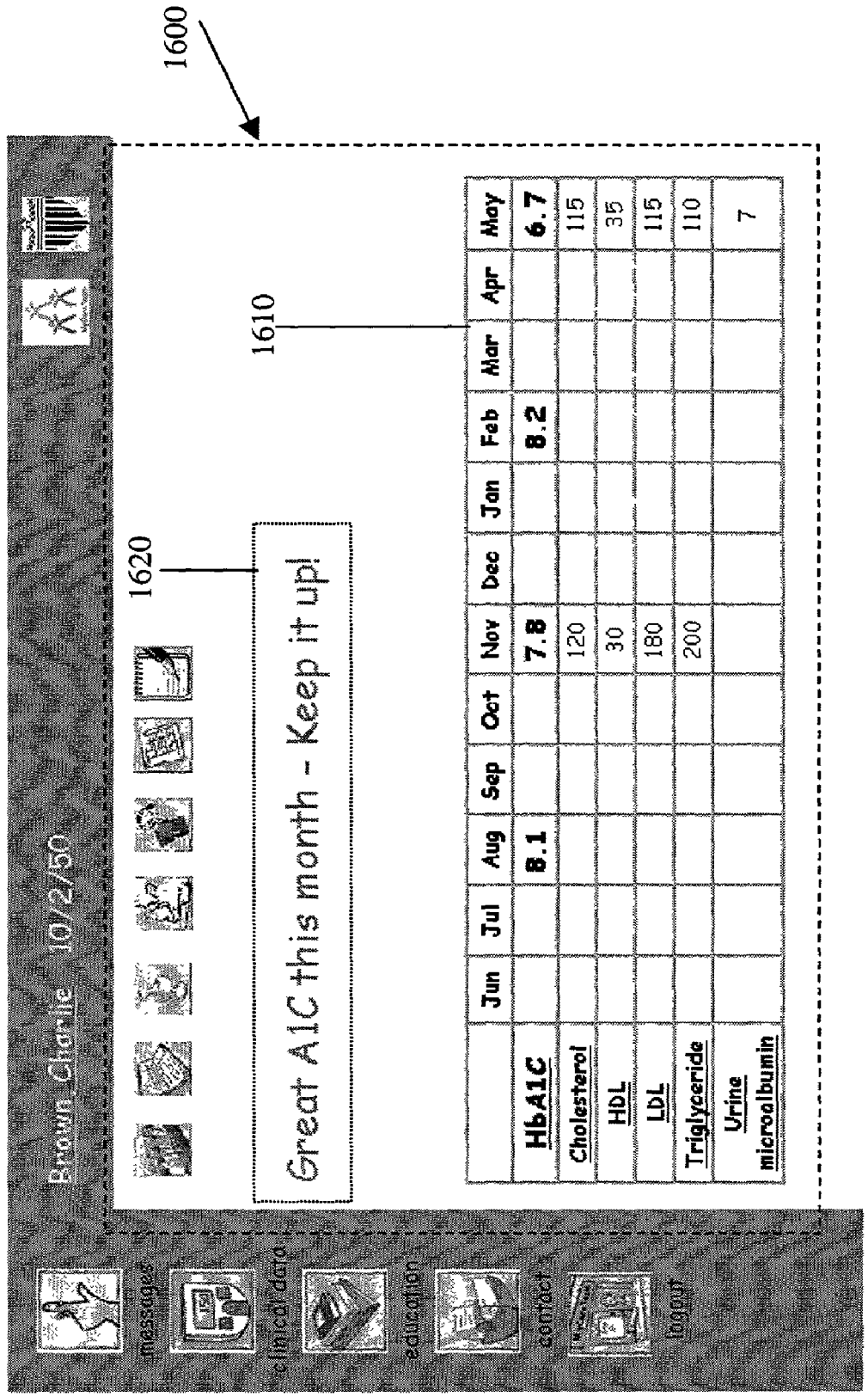
FIG. 21 shows one exemplary embodiment of a screen of a graphical user interface usable to display a table of laboratory results according to this invention.

Selecting the lab results icon 1502 of the toolbar 1501 changes the displayed one of the clinical data screens 1500-2100 or 6800 to the laboratory test results screen 1600. FIG. 21 shows one exemplary set of such laboratory test results displayed in the laboratory test results screen 1600. The laboratory test results screen 1600 presents laboratory test results of, for example, HbA1C, cholesterol, HDL, LDT., triglycerides, and urine microalbumin in a table 1610, indicating the laboratory test and the month the laboratory test was taken. When any of the laboratory tests having an associated hypertext link or graphical user interface widget is selected, an on-screen contextual message (not shown) may appear to explain what the laboratory test measures, its clinical significance and the acceptable clinical range of test values.

In FIG. 21, the patient has HbA1C test results that fall within the acceptable clinical range for the month of May. In this case, a simple comparison of the laboratory results with acceptable clinical values stored in the relational database 232 by the clinic system 200 is performed in real-time to determine whether the value is acceptable. For example, in various exemplary embodiments, if the HbA1C value is less than a site/patient configurable value, then a text message and/or an audio message is presented to the user in a message portion 1620. As shown in FIG. 21, the illustrated test results are below a site/patient configurable value. As a result, because the test results are acceptable, the clinic system may present in the message portion 1620 a congratulatory comment from the patient's healthcare practitioner, such as "Great A1C this month—Keep it up!", possibly accompanied by the sound of applause. This message and sound of applause provide motivation to the patient, when the patient has done well in managing his or her blood glucose values and are meant to reflect the feedback a patient would normally receive during a clinic visit from his or her healthcare practitioner.

Selecting the medication icon 1504 of the toolbar 1501 changes the displayed one of the clinical data screens 1500-2100 or 6800 to a medications screen 1700. The medications screen 1700 shows the medications used by the chronic illness patient. In the particular exemplary embodiment shown in FIG. 22, the medications screen 1700 is one that is appropriate for a diabetic patient. It should be appreciated that the contents of the medications screen will change depending on the particular chronic illness, as illustrated by the second exemplary embodiment of the medications screen 3700 shown in FIG. 37.

In the prescription portion 1710, the date and time of the current prescription for insulin, which has been prescribed by clinic healthcare practitioners, may be displayed. In the prescription portion 1710 of the medication screen 1700 displayed for a diabetic patient, an insulin medication table 1712 may indicate that both long and short acting insulin are currently prescribed for the patient, display the common or trade names of the prescribed insulin, and the dosage values and time of day that the prescribed type of insulin is to be taken. Previous prescription orders for insulin may be viewed by selecting the previous prescription hypertext link or graphical user interface widget 1714. The previous prescription order date is then displayed above the insulin medication table 1712, which now contains information about the previous prescription order. After reviewing the previous order, the patient may advance the prescription order to the current prescription date and order by selecting a next prescription graphical user interface widget or hypertext link (not shown), which will be displayed if the currently displayed prescription information is not that for the latest insulin prescription.

For diabetic patients who have an insulin pump, the insulin prescription information may be presented in a separate table (not shown) that includes, for example, the insulin pump prescription showing time versus basal rate, bolus information by meal including grams of carbohydrate, bolus size, insulin to carbohydrate ratio, prescribed supplemental insulin and information explaining how insulin converts various foods to carbohydrates.

In an oral medication portion 1720 of the medication screen 1700, the date of the current prescription of oral prescription drugs other than insulin, which has been prescribed by clinic healthcare practitioners, and an oral medication table 1722 is shown that may indicate the type of oral medication, its name, the dosage and number of tablets per dose, and the frequency with which the medication is to be taken. As described above, previous oral medication prescription orders and information concerning the previous prescription orders may be reviewed by selecting a previous prescription hypertext link or graphical user interface widget 1724 located above the oral medication table. Similarly, after reviewing a previous oral medication prescription order, selecting a next prescription hypertext link or graphical user interface widget (not shown) advances the oral medication prescription date and prescription order.

Figure 23:
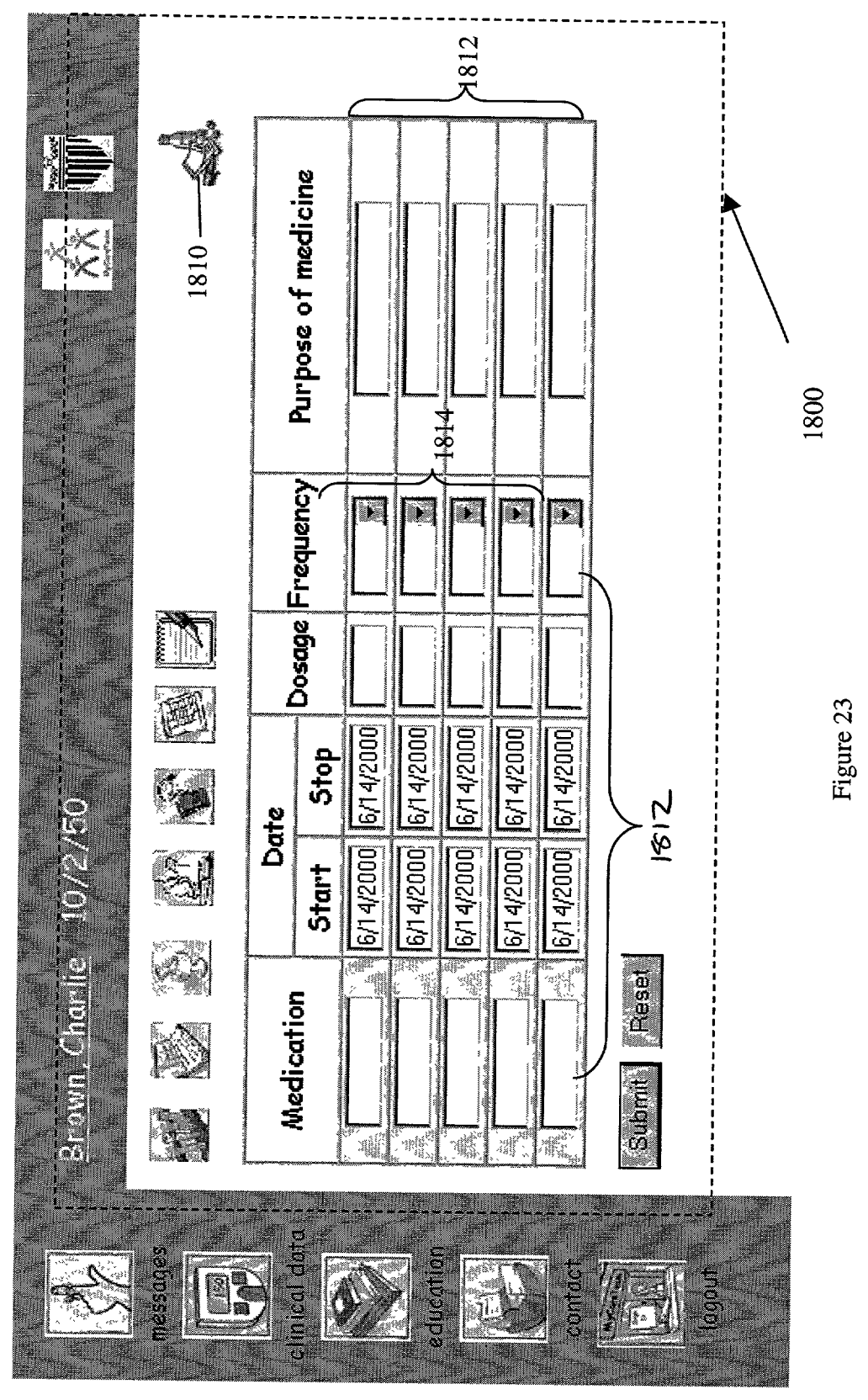

In an other medication portion 1730 of the medications screen 1700. non-prescription medications and other prescription medications, prescribed by a non-clinic healthcare practitioner, may be displayed. These other medications are entered into a displayed other medication table 1732 by the patient when he or she selects the add other medication icon 1740. Selecting the add other medication icon 1740 changes the medications screen 1700 to the add medications screen 1800 shown in FIG. 23. As shown in FIG. 23, the add medications screen 1800 includes a data entry table 1810 comprising a number of data entry input boxes 1812 and drop down list boxes 1814, in which the patient enters the information about other medications. The patient enters into the appropriate data entry input box 1812 via the patient data terminal 120, the name of the medication, when it was taken, its dosage, and the purpose of the medication. The frequency with which the medication is taken may be entered by accessing one of the drop list boxes 1814 that list once, twice and three times per day, or the like.

Information concerning the various medications taken by the patient may be communicated to other computerized clinical systems that analyze the information for possible adverse drug interactions. If such a system discovers a possible adverse drug interaction, this information may then be communicated to the clinical management system for chronic illnesses for inclusion in, for example, an alert displayed in the alerts portion 940. Alternatively, such information may be sent to a clinic healthcare practitioner, who in turn informs the patient.

Figure 24:
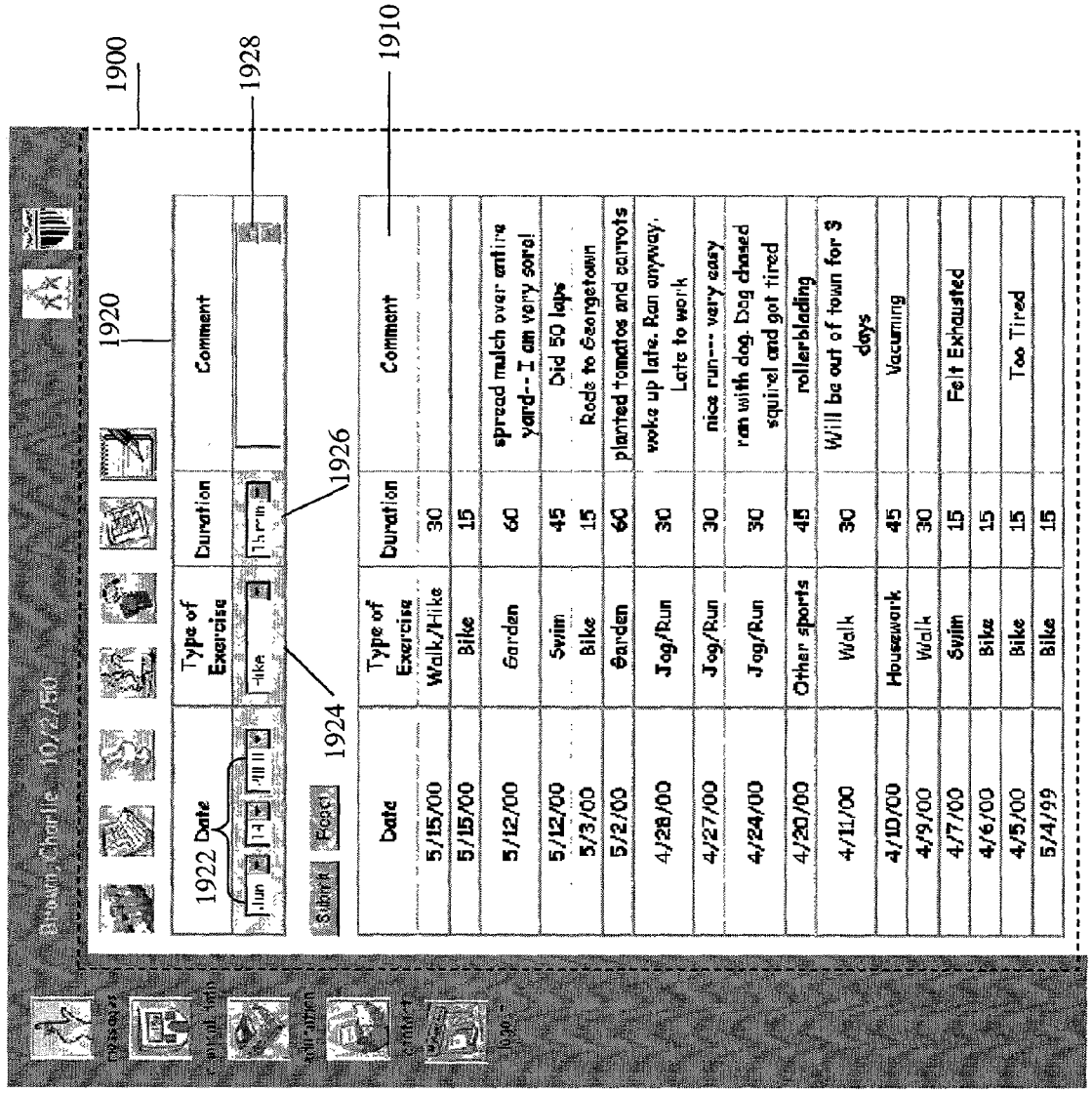
FIG. 24 shows one exemplary embodiment of a screen of a graphical user interface usable to display an exercise log according to this invention.

Selecting the animated exercise log icon 1505 changes the displayed one of the clinical data screens 1500-2100 or 6800 to an exercise data screen 1900. The exercise data screen 1900 includes an exercise log 1910, as shown in FIG. 24, and an exercise event entry portion 1920. The exercise event entry portion includes a number of drop down list boxes 1922-1926 in which the patient may enter the date, type of exercise, and duration of exercise, and a data entry input box 1928 for entering the patient's comments. Entering the date of a log entry may be facilitated by a set of standard drop down list box 1922 that allows the patient to select a particular month, date, and year. Similarly, a type of exercise drop down list box 1924 may provide for the selection of, for example, biking, jogging or running, swimming, walking or hiking, golfing, arm chair exercising, other sports, gardening, housework, and other activities. The duration of an exercise may be entered by a drop down list box 1926 that provides for the selection of 15, 30, 45 and 60 minutes or an "other" time interval. The data entry input box 1924 permits the patient to enter the patient's comments, via the patient's data terminal 120, which the patient feels will be relevant to the healthcare practitioner or may more filly describe an exercise activity or its duration. Comments from a healthcare practitioner may also be displayed in the exercise data screen 1900, indicating to the patient that the healthcare practitioner is reviewing and evaluating the level of the patient's physical activity.

Figure 25:
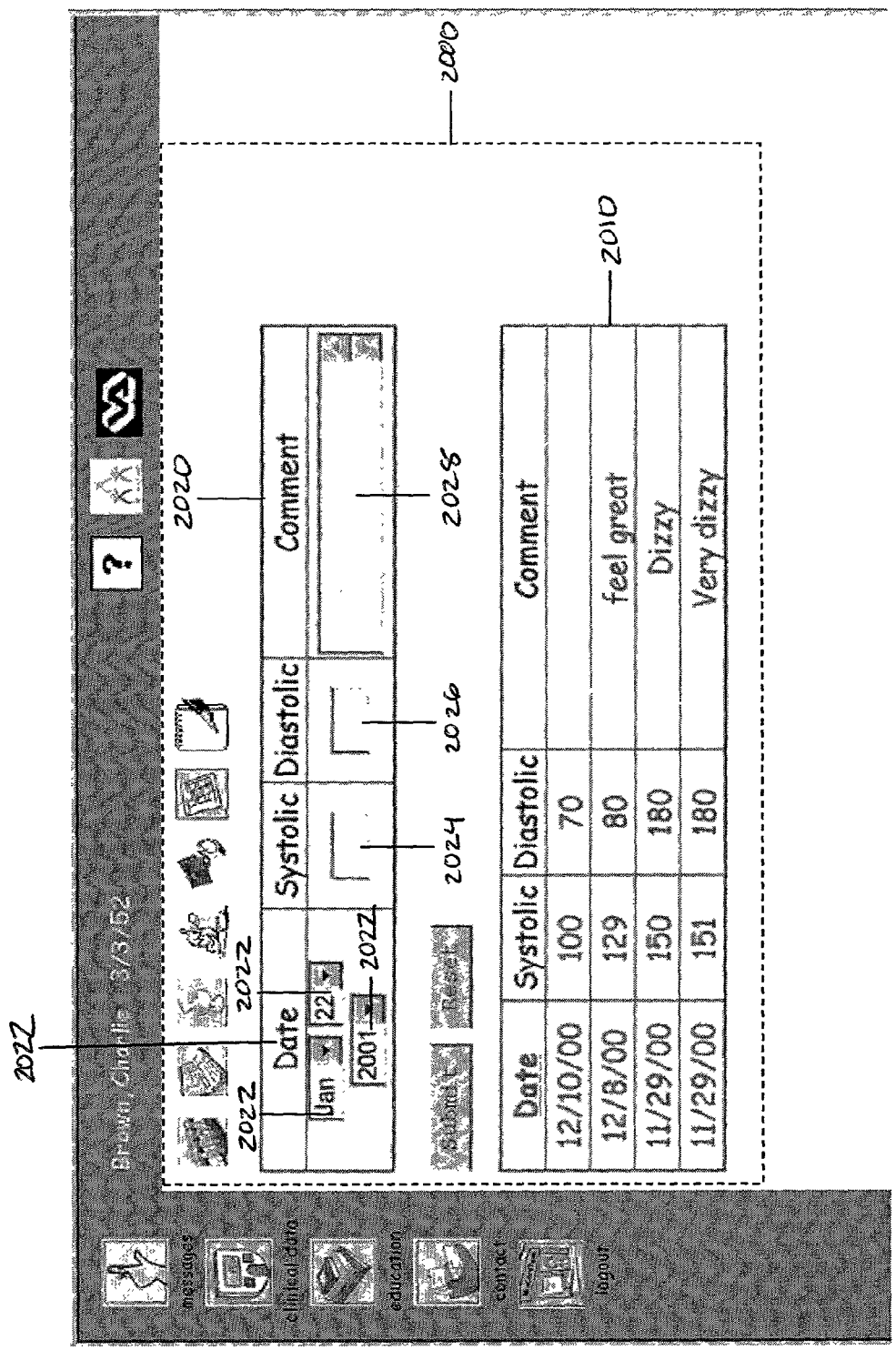
FIG. 25 shows one exemplary embodiment of a screen of a graphical user interface usable to display a blood pressure log according to this invention.

Selecting the blood pressure icon 1506 of the toolbar 1501 changes the displayed one of the clinical data screens 1500-2100 or 6800 to a blood pressure data screen 2000. The blood pressure data screen 2000 includes a patient blood pressure log 2010, as shown in FIG. 25. The blood pressure log 2010 is a table that displays blood pressure values by date, that are obtained from an automated or manual medical device 122 that the patient may connect to the patient's data terminal 120 and/or directly to the network 110. The blood pressure log 2010 allows for patient-entered comments. The blood pressure data screen 2000 also includes a manual entry portion 2020 that includes a number of data entry boxes 2022-2028. The patient may enter the date using drop down list boxes 2022, while systolic and diastolic blood pressures and comments may be entered into, for example, by the data entry input boxes 2024, 2026 and 2028, respectively. Comments (not shown) from the healthcare practitioner about the patient's blood pressure may be displayed in the blood pressure data screen 2000. It should be appreciated that, if the clinic system 200 is able to accept data from an electronic blood pressure device as the medical device 122, the manual entry portion 2020 may be omitted.

Figure 26:
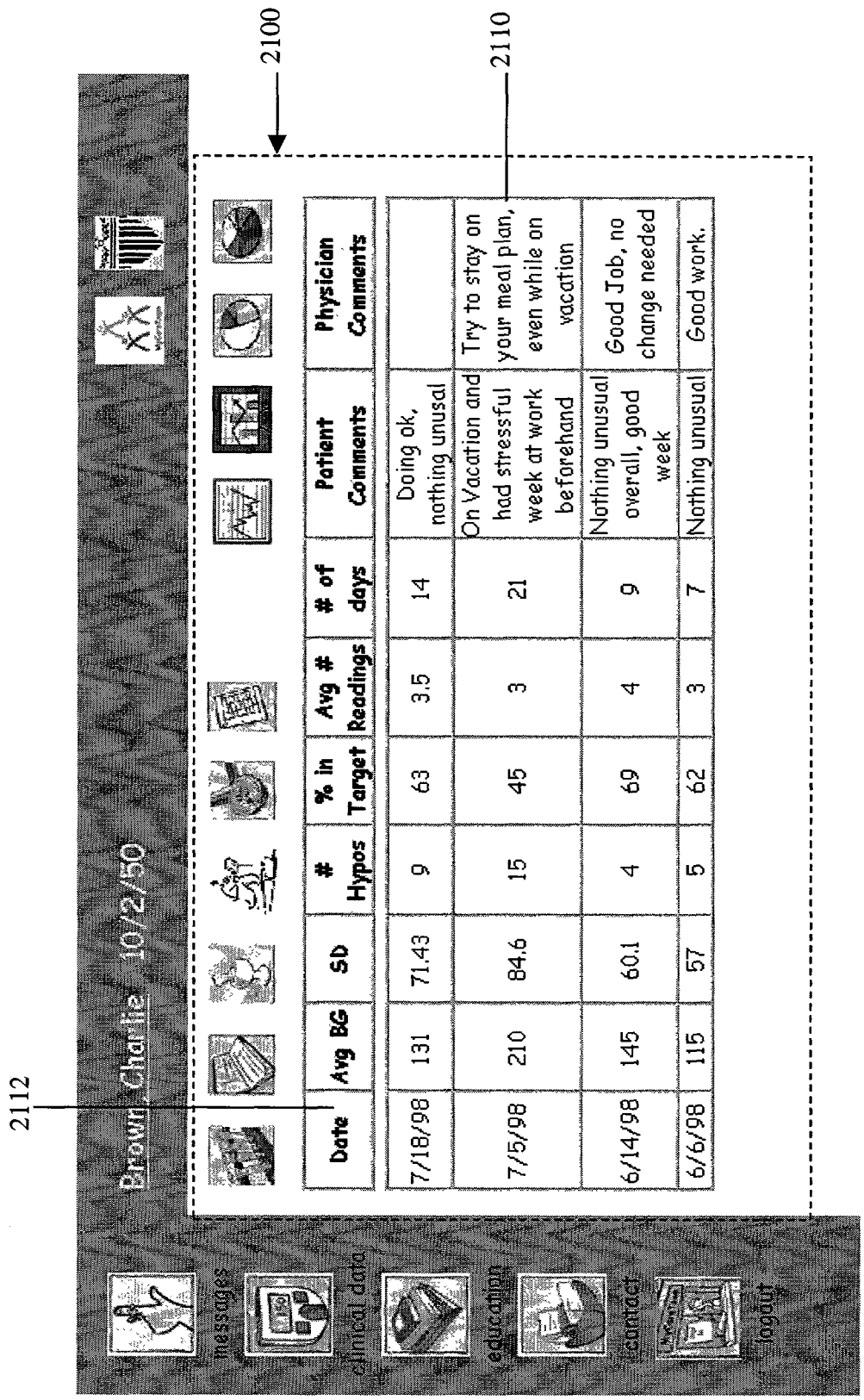
FIG. 26 shows one exemplary embodiment of a screen of a graphical user interface displaying a tabular data summary and patient and healthcare practitioner comments according to this invention.

Selecting the data summary and healthcare practitioner comments icon 1507 changes the displayed one of the clinical data screens 1500-2100 or 6800 to the summary screen 2100. The summary screen 2100 includes a tabular summary 2110, as shown in FIG. 26. In FIG. 26, the tabular summary 2110 presents by date, for example, the average blood glucose value, the standard deviation of the blood glucose values, the number of hypoglycemic and hyperglycemic events, the percentage of blood glucose readings within the desired target range, the average number of blood glucose readings per day, and the number of days for which the clinical data is summarized. When reviewing the tabular summary 2110 of FIG. 26, the patient may enter comments regarding his or her latest blood glucose values, for example, by a standard data entry box 2120 as shown in FIG. 27, to which the healthcare practitioner may reply.

Figure 28:
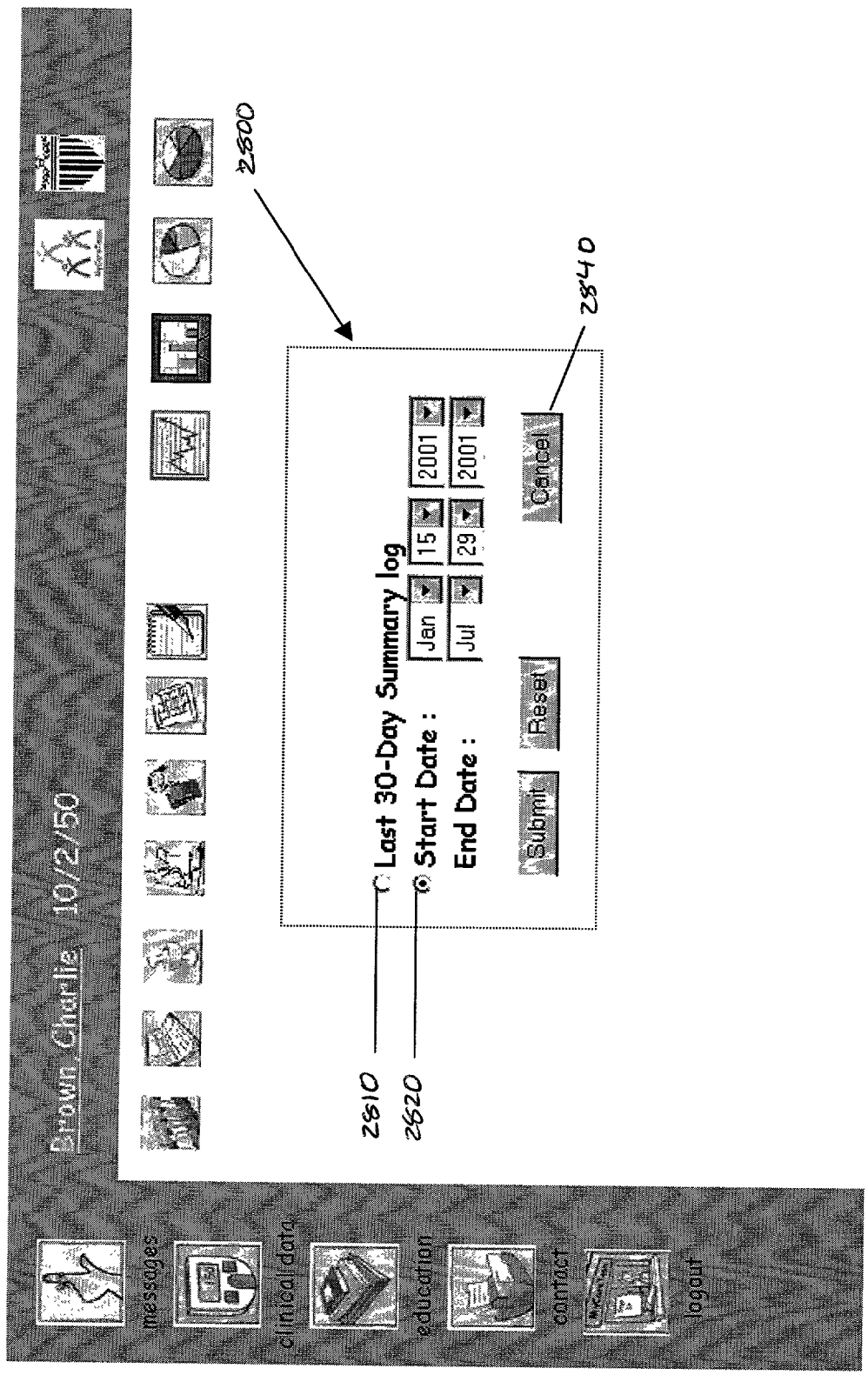
FIG. 28 shows one exemplary embodiment of a screen of a graphical user interface displaying a date selection graphic according to this invention.

By selecting the date icon 2112 in the upper left corner of the tabular summary 2110 of FIG. 26, a data selection screen or window 2800 is displayed, as shown in FIG. 28. The data selection screen or window 2800 shows two options, a "Last 30-Day Summary" option button 2810 or a "Start Date/End Date" second option button 2820. A "Cancel" button 2840 may cancel the dates' selection screen and return the patient to the summary screen 2100 shown in FIG. 26.

Figure 68:
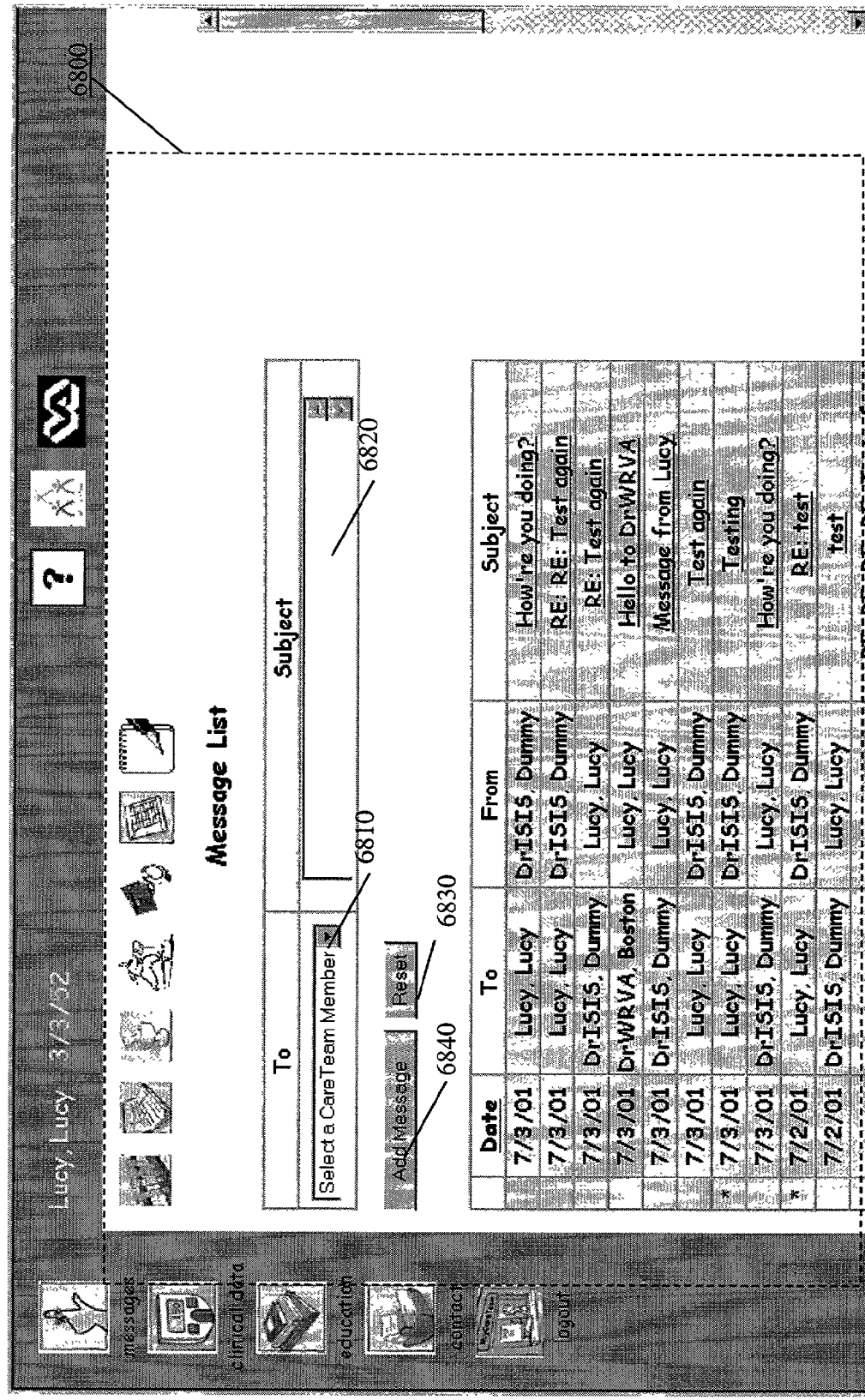
FIG. 68 shows one exemplary embodiment of a patient message list screen of a graphical user interface according to this invention.

Selecting the patient message list icon 1508 of the toolbar 1501 changes the displayed one of the clinical data screens 1500-2100 displayed in the central data area 710 to the patient message list screen shown 6800 in FIG. 68. The patient is presented with a list of messages sent by the patient's healthcare practitioner or by the patient, as shown in FIG. 68. Information, such as the date a message was sent, to whom the message was sent, who sent the message, and the subject/title of the message may be presented. In various exemplary embodiment, all unread messages in the list are preceded by a red asterisk.

Figure 69:
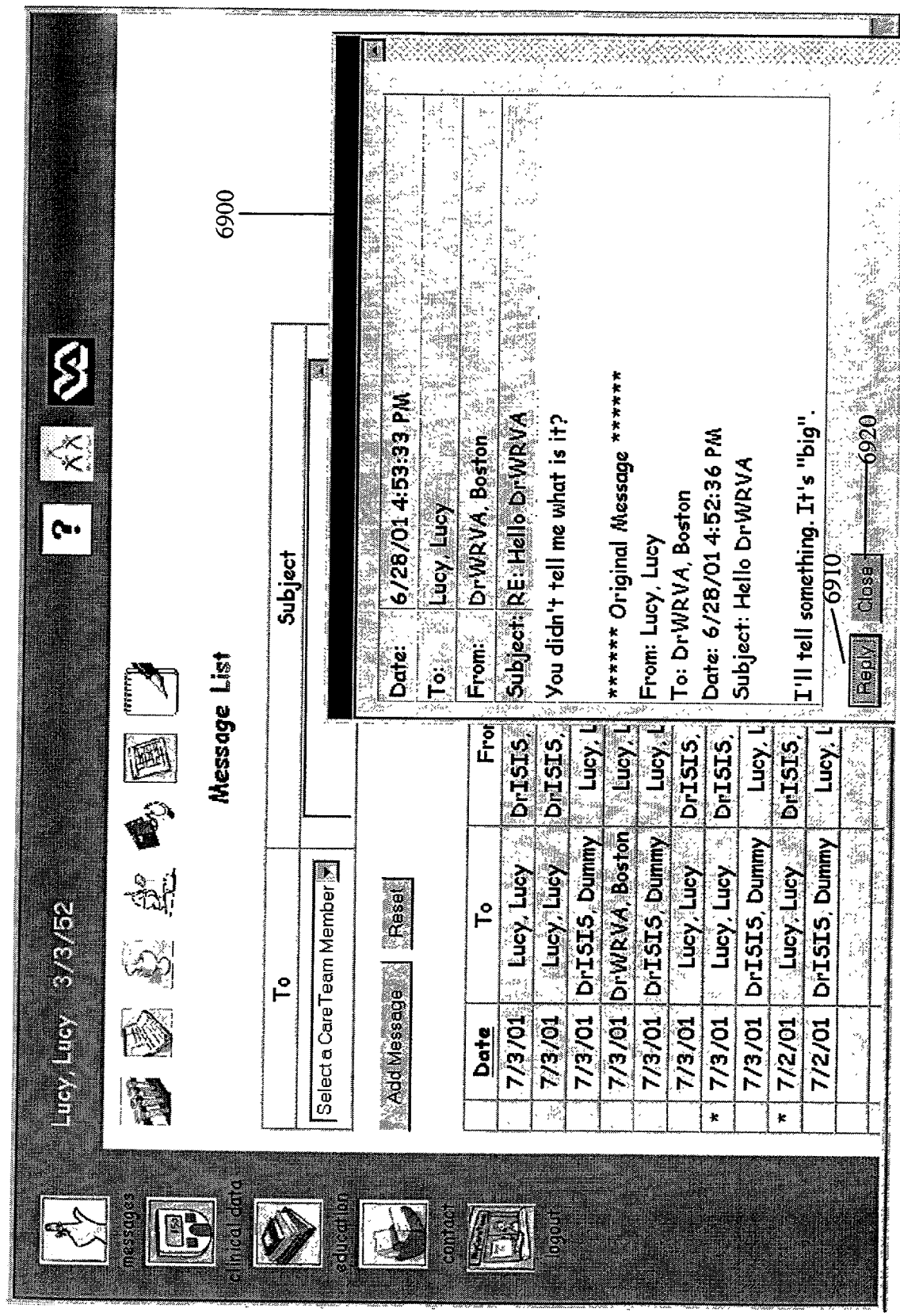
FIG. 69 shows one exemplary embodiment of a patient message list screen of a graphical user interface according to this invention.

When the patient selects one of the underlined subject/titles, the clinical management system retrieves the selected message for the patient, as shown in FIG. 69. A message list screen 6900 appears with information such as the date the message was sent, to whom the message is addressed, who sent the message, the subject/title of the message and the message itself. If the entire message does not fit within the message list screen 6900 horizontal and/or vertical scroll bars are presented for the patient to scroll through the message (not shown). At the end of the message there is a reply button 6910 and a close button 6920. When selected, the reply button 6910 allows the patient to send a response message to whomever sent the message (not shown). The close button 6920 allows the patient to exit the message list screen 6900 and return the patient to the patient message list screen 6800 of FIG. 68 (not shown). The patient may also exit from the message list screen 6900 by selecting the standard window exit icon (not shown) in the top right hand corner of the message list screen 6900 to return to the patient message list screen 6800.

The patient may also create and add a new message to the messages displayed in the patient message list screen 6800. The patient selects a "Select a CareTeam Member" drop down list box 6810. The "Select a CareTeam Member" drop down list box 6810 provides a list of the healthcare practitioners in the chronic illness management system 100. The patient then selects the healthcare practitioner the patient wishes to address the message to (not shown). The patient may also provide a subject/title for the message, but this is not required. The patient does this by simply typing in the subject/title in the "Subject" data entry box 6820 in FIG. 68.

If the patient decides to discard the message, has made an error, or wants to change to whom the message is addressed to and/or the subject/title of the message, the patient can select the reset button 6830. When selected, the reset button 6830 clears to whom the message is addressed to and clears the "Subject" data entry box 6820 The function of the reset button 6830 can also be accomplished by selecting a different individual from the "Select a CareTeam Member" drop down list box 6810 for whom the message is addressed and by backspacing over the incorrect data entry and then typing the correct data in the "Subject" data entry box 6820.

Figure 70:
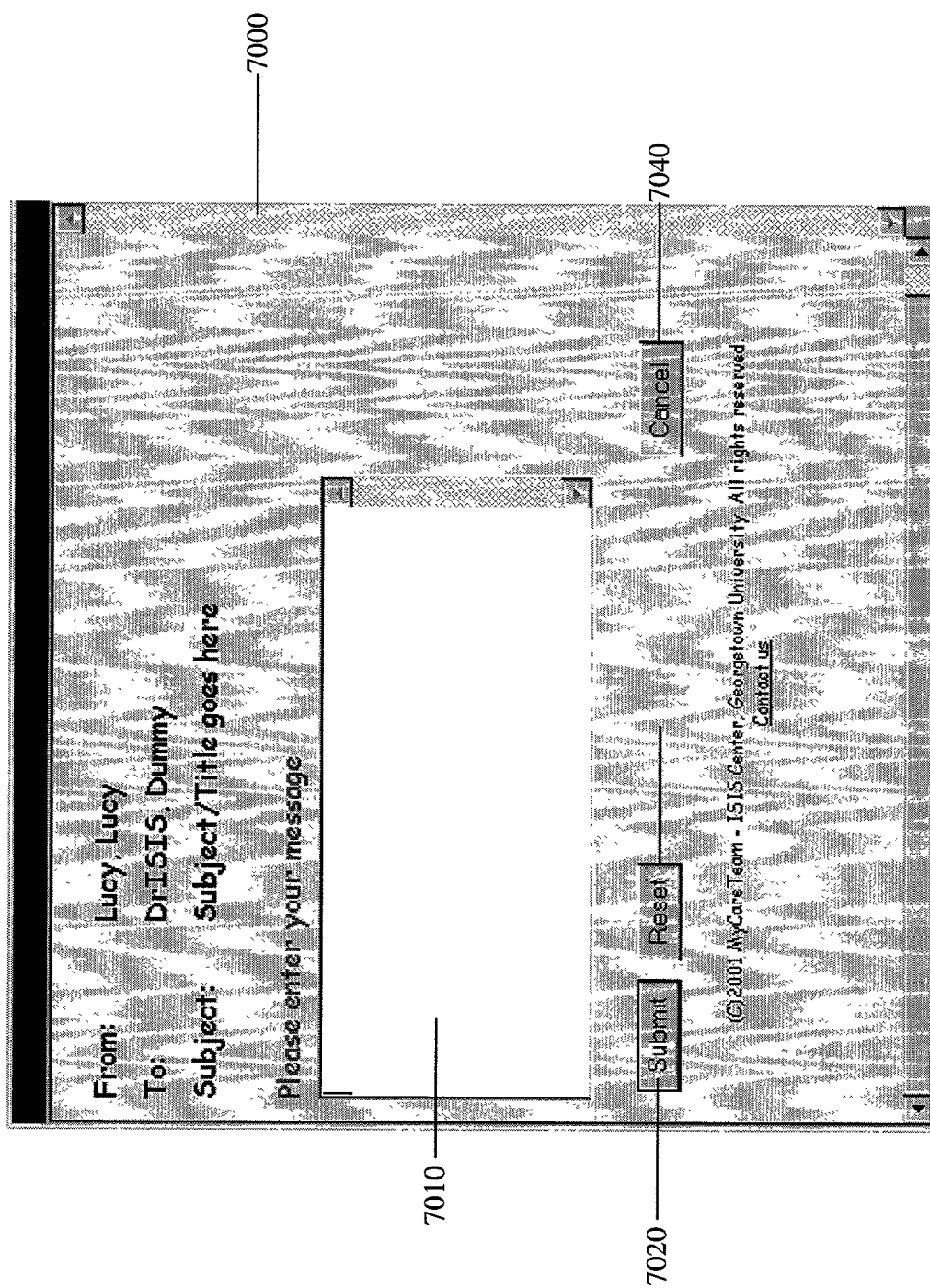
FIG. 70 shows one exemplary embodiment of a screen of a graphical user interface usable to add a message according to this invention.

After the patient has selected the healthcare practitioner to whom the message is addressed and typed a subject/title for the message (optional), the patient selects the "Add Message" button 6840. When the patient selects the "Add Message" button 6840, the patient message list screen changes to the add message screen shown in FIG. 70. The add a message screen 7000 displays the patient's name as who the message is from, the name of the healthcare practitioner to whom the message is addressed and the subject/title, if provided by the patient. Additionally, there is a message data entry box 7010, a submit button 7020, a reset button 7030, and a cancel button 7040. The patient then enters his or her message into the message data entry box 7010 by using the keyboard or some other data entry device. Once finished, the patient selects the submit button 7020 to send the message. If the patient is unsatisfied with the inputted message and wishes to discard all of its contents, the patient simply selects the reset button 7030 or backspaces over the undesired portions of the message. However, if the patient wishes to disregard sending a message all together, the patient can select the cancel button 7040. This returns the patient to the patient message list screen 6800 of FIG. 68.

When a diabetic patient selects the education icon 836 of the main patient data screen 700 shown in FIG. 10 or included in any other screen having a blue color-coded frame 800, the screen displayed in the central display area 710 changes to a diabetes education screen 2200, as shown in FIG. 29. The diabetes education screen 2200 includes a number of icons 2210-2250 that cause screens providing more detailed information on a particular subject to be displayed. The patient may then select one of the icons 2210-2250, for example, the icon 2210 labeled "What Is Diabetes?". In response, as shown in FIG. 30, a second education screen 2300 for the selected topic will be displayed in the central display area 710.

Figure 30:
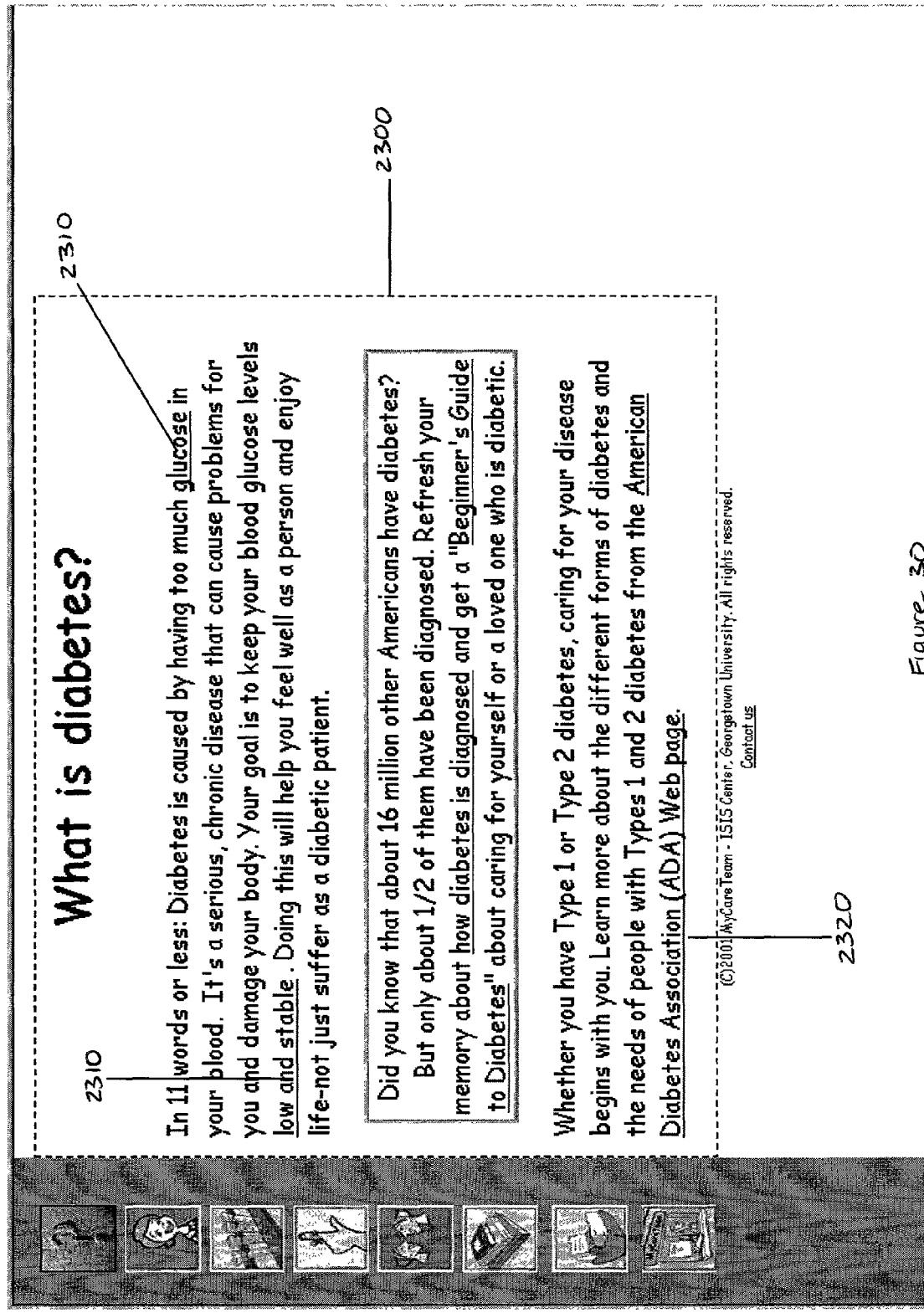
FIG. 30 shows one exemplary embodiment of a screen of a graphical user interface displaying a particular educational information according to this invention.

The displayed educational topics may include, for example, hypertext links or graphical user interface widgets associated with various words or phrases 2310, or Web sites 2320, as shown in FIG. 30. Selecting such a word or phrase 2310 may result in an on-screen contextually relevant message being displayed that explains or identifies the selected word or phrase. Selecting such a Web site 2320 causes the system to access the associated Web site. Upon leaving the accessed Web site, the patient returns to the displayed educational topic.

When a diabetic patient selects the contacts icon 838 of the main patient data screen 700 shown in FIG. 10 or included in any other screen having a blue color-coded frame 800, the screen displayed in the central data area 710 changes to a healthcare practitioner contact screen 2400. The healthcare practitioner contact screen 2400 includes a graphic and pictorial representation of the clinic's diabetes treatment and monitoring team, as shown in FIG. 31. A hypertext link or graphical user interface widget 2410-2440 is associated with each team member. An email access icon 2412-2442 is also associated with each team member. If the patient selects the hypertext link or graphical user interface widget 2410-2440 of a team member, a short biographical sketch (not shown) of the team member is displayed in a separate window or a separate screen. This biographical sketch helps to familiarize the patient with the clinicians handling the patient's case. If the email access icon 2412-2462 is selected, a dialog box containing the corresponding email or message address of the selected team member where that team member can be reached is displayed. If the patient selects the Support Group Message icon (not shown), a dialogue box (not shown) containing the support group's e-mail or message address where the patient may chat with others having the same chronic illness. By selecting the Technical Support Email icon 2462, the screen may show a dialogue box (not shown) containing the technical support group's e-mail or message address to assist the patient with technical problems associated with communicating with the system and using it properly.

It should be appreciated that the screens shown in FIGS. 29-31 are the diabetes education screens 2200 and 2300 and the contact screen 2400 as displayed to a healthcare practitioner. The various icons used when displaying these screens to the healthcare practitioner are described in greater detail below with respect to FIG. 50. That is, the diabetes education screen 2200 and 2300 and the contact screen 2400 display the same information in the central data area 710 to both patients and to healthcare practitioners. The only significant difference when displaying these screens is that the particular tool bar icons displayed in the frame 800 depends on whether these screen are being displayed to a health care practitioners, as shown in FIGS. 29-31, or to a patient. In that later case, the frame 800 shown in FIGS. 10-28 would be displayed.

When an authorized kidney disease patient signs on to the clinic system 200 using the clipboard of FIG. 7, the screen changes to show the kidney main patient data screen 3200, shown in FIG. 32, that is appropriate for a patient to manage the patient's kidney disease. The kidney main patient data screen 3200 includes a frame 3202 with upper and left-side borders, and a central display area 3210, as shown in FIG. 32. The background 810 of the upper and left-side borders of the frame 3202 of the main patient data screen 3200 may be colored green to signify a kidney disease patient. The background 810 of the upper border of the frame 3202 includes the underlined patient's name 3220, the date of birth 3222, an icon 3224 linked to another screen of the graphical user interface and a selectable icon or hypertext link 3226 linked to, for example, a Web site for the university associated with the clinic. Selecting the underlined patient's name 3220 changes the screen to the "Patient Information Update" screen, as discussed above and shown in FIG. 12. The left border of the frame 3202 may include, for example, icons for "messages" 3232, "clinical data" 3234. "education" 3236, and "contact" 3238 that change the information displayed in the central display area 3210 and a "logout" 3239 icon that accesses the screen for the clinic lobby 400. Among the icons in the left border of the frame 3202, only the "education" 3236 icon has changed its appearance from that of the frame 800 shown in FIG. 10, showing, instead, a pair of kidneys. By selecting the "education" 3236 icon for the kidney patient, an on-screen contextually relevant message may read "dialysis education site".

The initial screen presented to the kidney disease patient upon entering the kidney disease clinic is the main patient data screen 3200 with "ALERTS:" 3250, "MESSAGES:" (not shown) and "REMINDERS:" (not shown) displayed in the central display area 3210 of FIG. 32. In FIG. 32, the underlined "What'sNew?" 3242 and the drop down list box 3244 labeled "Kidney Disease News Archive" are connected to information stored in the relational database 232 of the clinic system 200 concerning kidney disease. For example, selecting "What'sNew?" 3242 displays the latest news concerning kidney disease and peritoneal dialysis, as shown in FIG. 33. If the amount of information in the news of FIG. 33 exceeds the size of the central display area 3210, a vertical and/or horizontal scroll bar located at the right border of the screen (not shown) allows the patient to view the entire news In FIG. 32, the information concerning "ALERTS:" 3250 derives from the clinic system's 200 analysis of quantitative clinical data submitted by the patient using a medical device 122 for at-home peritoneal dialysis, blood pressure and weight measures submitted by the patient, and laboratory test results entered into the clinic system 200 by the patient's healthcare practitioner. The information presented to the patient concerning "ALERTS:" 3250, "MESSAGES:" and "REMINDERS:" is automatically analyzed in real-time by the clinic system 200 from data stored in the relational database 232 when the patient initially accesses the main patient data screen shown in FIG. 32. The "ALERTS:" 3250 summarize those events and activities, which may be detrimental to the patient and may include, for example, the date of the last PD, that is, peritoneal dialysis data received, weight gain or loss, changes in blood pressure, and clinical laboratory results including creatinine, potassium, albumin, glucose and phosphate levels, and Kt/V, that is, a measure of the quantity of dialysis delivered. In FIG. 32, for example, the system has determined that the patient has not submitted PD data, that is, peritoneal dialysis data, for 26 days. The "ALERTS:" 3250 may also emphasize the number of days a peritoneal dialysis datum has not been received by using a red color for the number, corresponding to the color of "ALERTS:" 3250. Additionally, by selecting underlined laboratory tests or medical terms in "ALERTS:" 3250, an on-screen contextually relevant message (not shown) may be displayed to further explain the laboratory test or medical term.

The information concerning "MESSAGES:" for a kidney disease patient in the main patient data screen 3200 may include, for example, that Kt/V or other laboratory test values are in a clinically acceptable range, thus, indicating good management of the kidney disease by the patient. Good and poor management of the patient's kidney disease may be indicated to the patient by various messages, including animated smiling or frowning faces (not shown) and accompanying sounds.

The information concerning "REMINDERS:" for a kidney disease patient in the main patient data screen of 3200 may include reminders entered into the clinic system 200 and stored in the relational database 232 by the patient's healthcare practitioners about upcoming medical visits, medical exams and laboratory tests, and health care tips.

Figure 34:
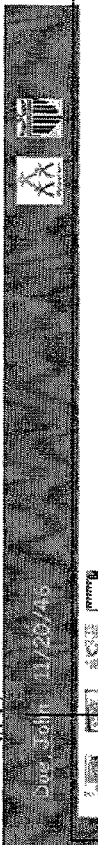
FIG. 34 shows a second exemplary embodiment of the patient supplied data screen of the graphical user interface according to this invention displaying an automated cycler flow sheet.

Selecting the "clinical data" icon 3234 of FIG. 32 or any other patient screen having a green frame, changes the information displayed to that of FIG. 34, showing a peritoneal dialysis prescription 3404 and the clinical data submitted by the patient to the system, that is, the "Automated Cycler Flow Sheet" 3410. The "Lab Results" icon 3430 and the "Medication" icon 3434 located above the current peritoneal dialysis prescription table 3404 changes the type of information displayed in the central display area 3405 of FIG. 34. The "Automated Cycler Flow Sheet" 3432 icon of all patient screens having the green frame displays the "Automated Cycler Flow Sheet" 3410 of FIG. 34. In FIG. 34, the current peritoneal dialysis prescription shows the date and time of the prescription above a peritoneal dialysis prescription table 3404 including prescription information relating to, for example, therapy time, dwell time, number of cycles, total volume, fill volume, and last fill volume. The clinical data of the "Automated Cycler Flow Sheet" 3410 are the date and time of the peritoneal dialysis, the percentage concentrations of the dextrose solutions used, the volume of initial drain, the volume of total UF, that is ultrafiltrate, blood pressure, and body weight, as shown in FIG. 34.

Figure 35:
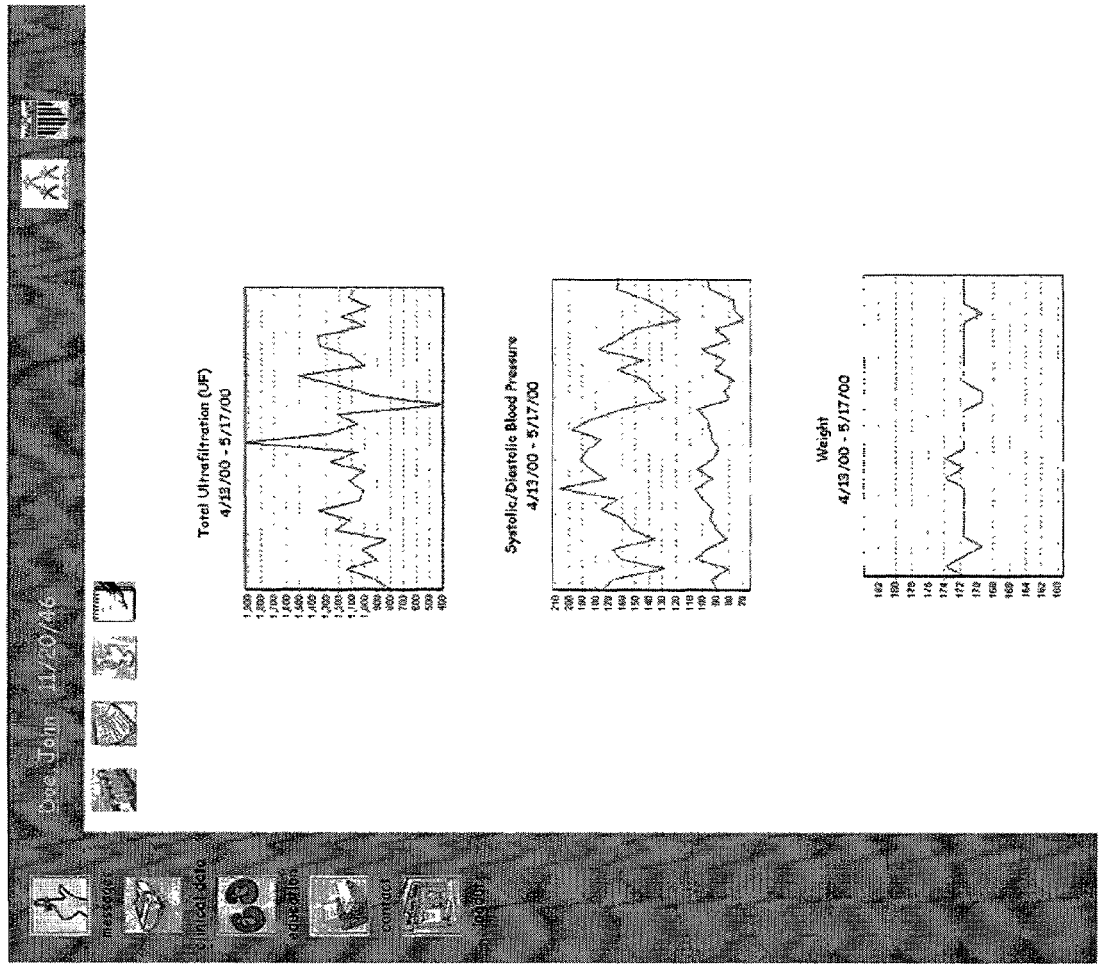
FIG. 35 shows a second exemplary embodiment of the screen of a graphical user interface usable to display linear graphs according to this invention.

Selecting any of the icons 3420 located above the Total UF, BP or WT columns of the "Automated Cycler Flow Sheet" of FIG. 34 changes the presentation of the clinical data of the column to a linear graph of that column's variable versus the Automated Cycler Flow Sheet's time period. For example, FIG. 35 shows, respectively, the changes in Total Ultrafiltrate, Blood Pressure and Weight over the time period of the Automated Cycler Flow Sheet as linearly plotted graphs.

Figure 36:
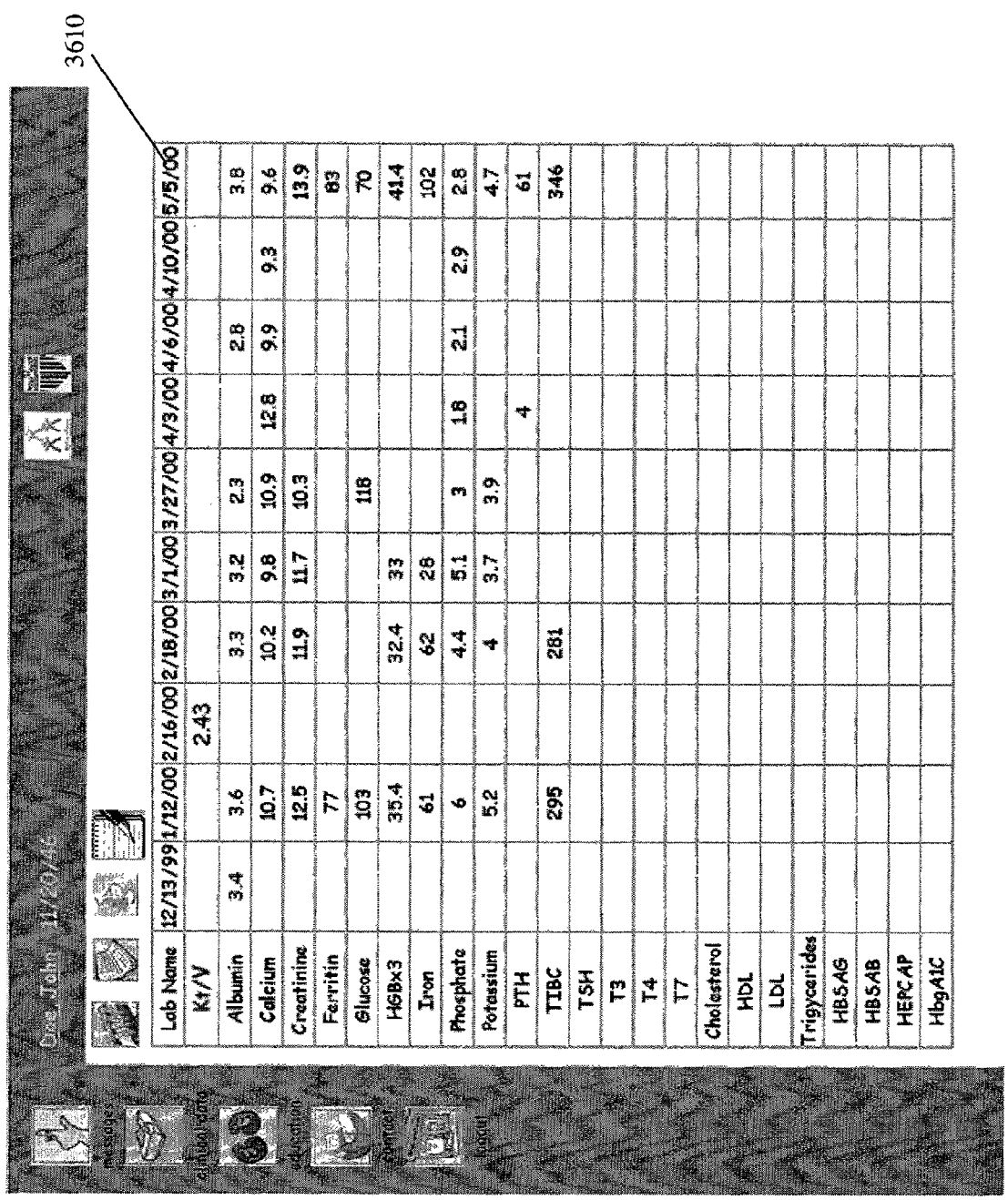
FIG. 36 shows a second exemplary embodiment of the screen of the graphical user interface usable to display a table of laboratory results according to this invention.

Selecting the "Lab Results" icon 3430 of FIG. 34 or any other patient screen having a green frame 3202 changes the type of clinical data displayed to that of laboratory test results, as shown in FIG. 36. FIG. 36 may present twelve dates on which laboratory test results may be displayed in a table 3610, with rows corresponding to a particular type of laboratory test and columns corresponding to a test date. The clinic system 200 may display more than twelve test dates with additional table displays. The laboratory test results displayed may include, but are not limited to, for example, Kt/V, albumin, calcium, creatinine, ferritin, glucose, HGB×3 (Hemoglobin times 3), iron, phosphate, potassium, PTH (parathyroid hormone), TIBC (total iron binding capacity), TSH (thyroid stimulation hormone), T3, T4, T7 (thyroid studies), cholesterol, HDL (high density lipids), LDL (low density lipids), triglycerides, HBSAG, HBSAB (hepatitis B surface antigens), HEPCAP (hepatitis C surface antigen) and Hb1AC (hemoglobin A1C)

When any of the laboratory tests of FIG. 34 is selected, an on-screen contextual message (not shown) may appear to explain what the laboratory test measures, its clinical significance to managing the illness and the acceptable range of clinical test values. When laboratory test results indicate that the patient is managing his or her illness well, the clinic system 200 may present a congratulatory message above the table 3610 (not shown). Laboratory test results may be color coded to represent values above, below and within acceptable clinical ranges. For example, red values may represent high results, blue values may represent low results and green values may indicate those within a clinically acceptable range. Alternatively, pluses and minuses may indicate high and low values, respectively.

Selecting the "Medication" icon 3434 of FIG. 34 or of any other patient screen having a green frame 3202 changes the type of clinical data displayed to that of a "Medications" table 3710 and an "Other Medications" table 3720, as shown in FIG. 37. The medications prescribed by the clinic healthcare practitioners are entered into a "Medications" table 3710 for review by the healthcare practitioner and patient. The "Medications" table 3710 may include, for example, the medication name, its dosage, its units, its frequency taken, its route of administration, the prescription start and stop dates, and instructions to the patient.

The "Other Medications" table 3720 of FIG. 37 includes information about non-prescription medications and other prescription medications, prescribed by non-clinic healthcare practitioners for the patient Thus, the "Other Medications" table 3720 of FIG. 37 provides the patient with a mechanism to enter outside medications the patient may be taking that the healthcare practitioner may not know about. This information is entered into the "Other Medications" table 3720 by the patient when he or she selects the "Add other medication" 3735 icon in the upper right corner of FIG. 37. The other medications are added to the table by the data entry tables discussed above in relation to the diabetic patient, as shown in FIG. 23.

Figure 38:
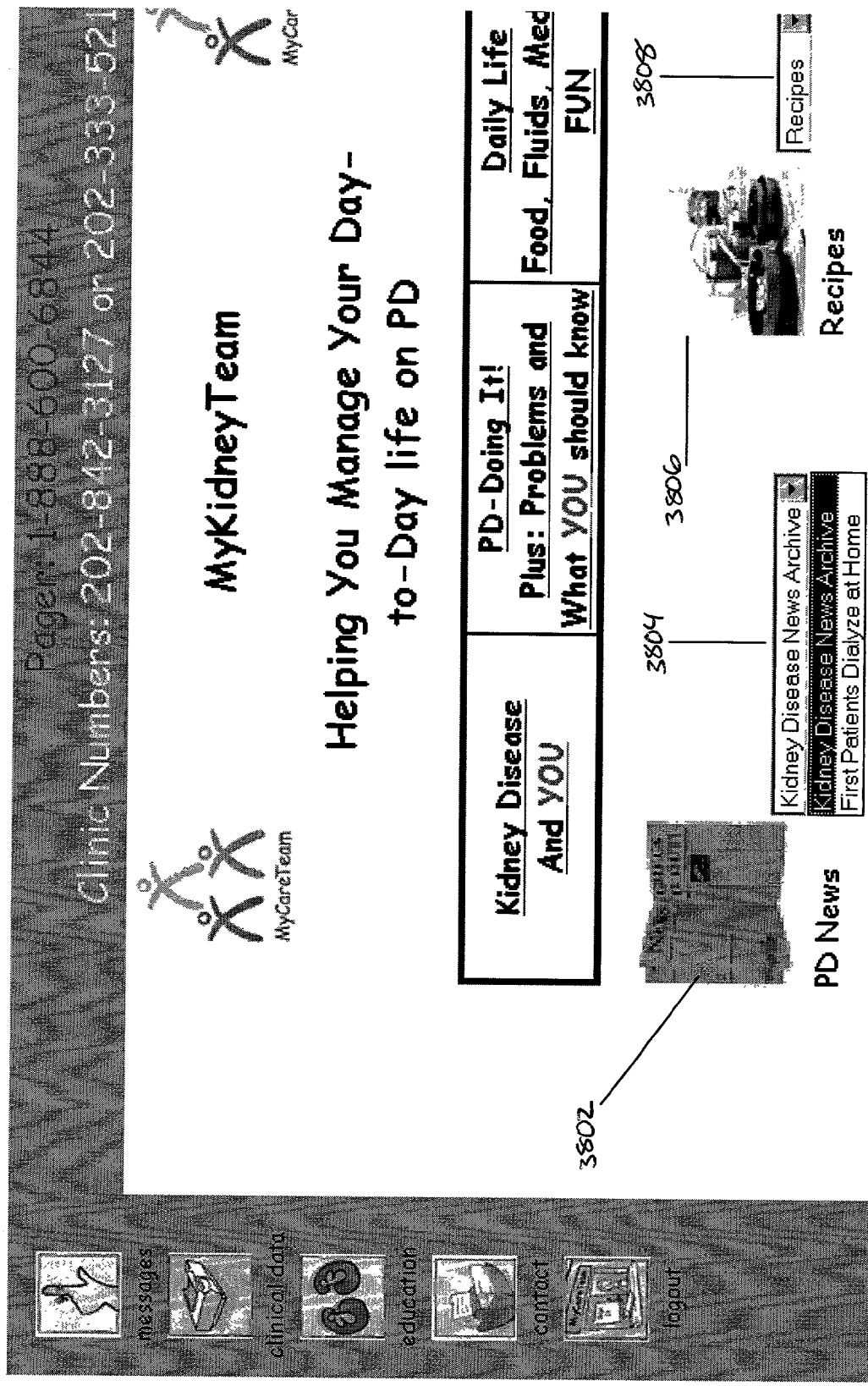
FIG. 38 shows a second exemplary embodiment of the screen of the graphical user interface displaying an educational page according to this invention for patients having a chronic kidney illness.
Figure 39:
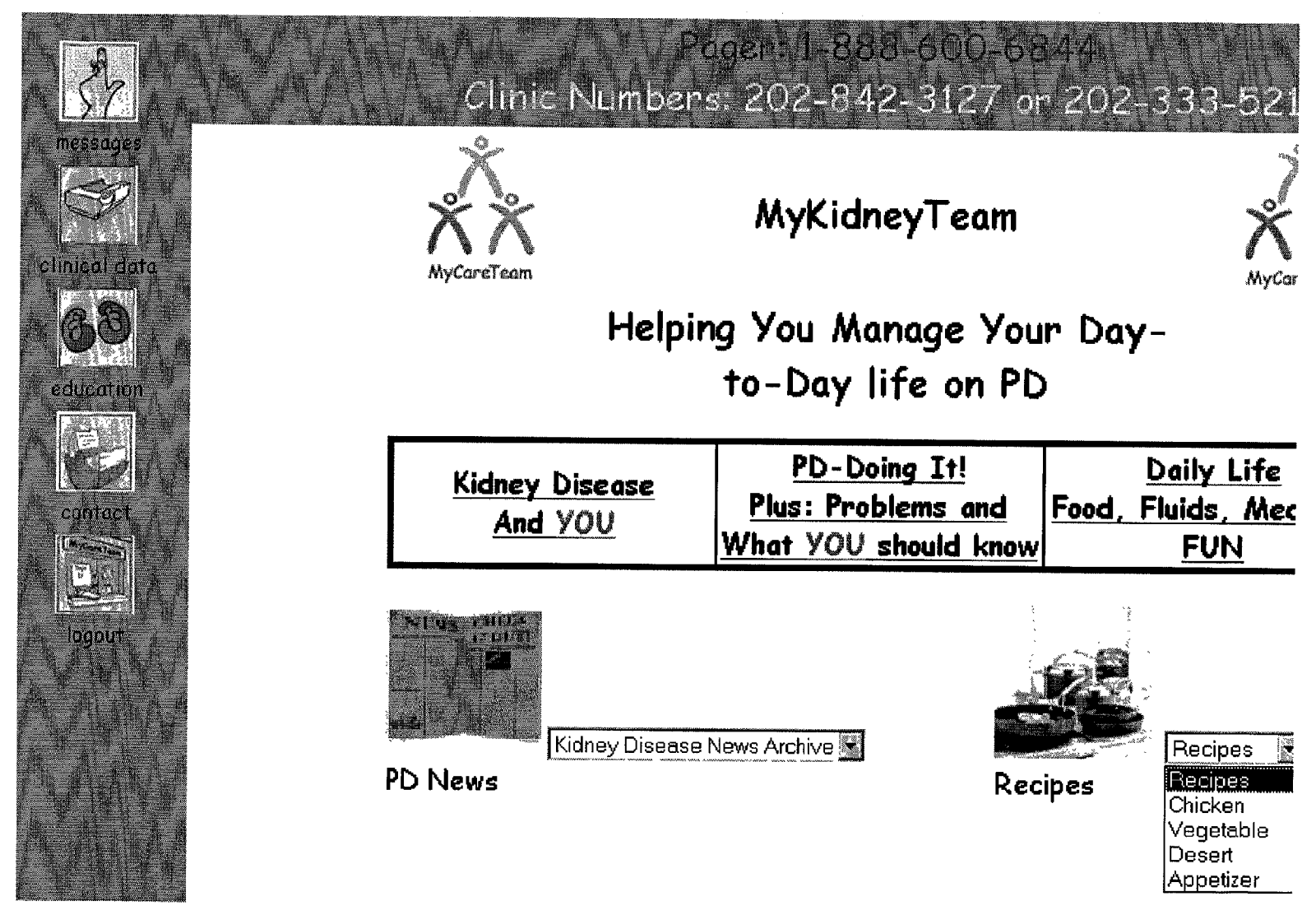

When a kidney disease patient selects the "education" icon 3236 of FIG. 32 or any other patient screen having a green frame, the upper border of the frame 3202 displays Pager and Clinic telephone numbers, while the central display area 3210 displays the main education page for kidney patients, as shown in FIG. 38. In the main education page of FIG. 38, the patient may select among the three underlined educational topics for display: "Kidney Disease and YOU"; "PD-Doing It Right!, Plus: Problems and What YOU should know"; and "Daily Life, Food, Fluids, Meds and FUN". The main education page of FIG. 38 may also display a "PD News" 3802 icon that when selected displays the latest news about kidney disease and/or peritoneal dialysis. A drop down list box 3804, labeled "Kidney Disease News Archive", may allow patients to access archival articles stored in the relational database 232 of the clinic system 200 for display. Additionally, the central display area may display a "Recipes" icon 3806 that when selected displays a current recipe. A drop down list box 3808, labeled "Recipes", may allow patients to access other recipes for display in the central display area, as shown in FIG. 39.

Figure 40:
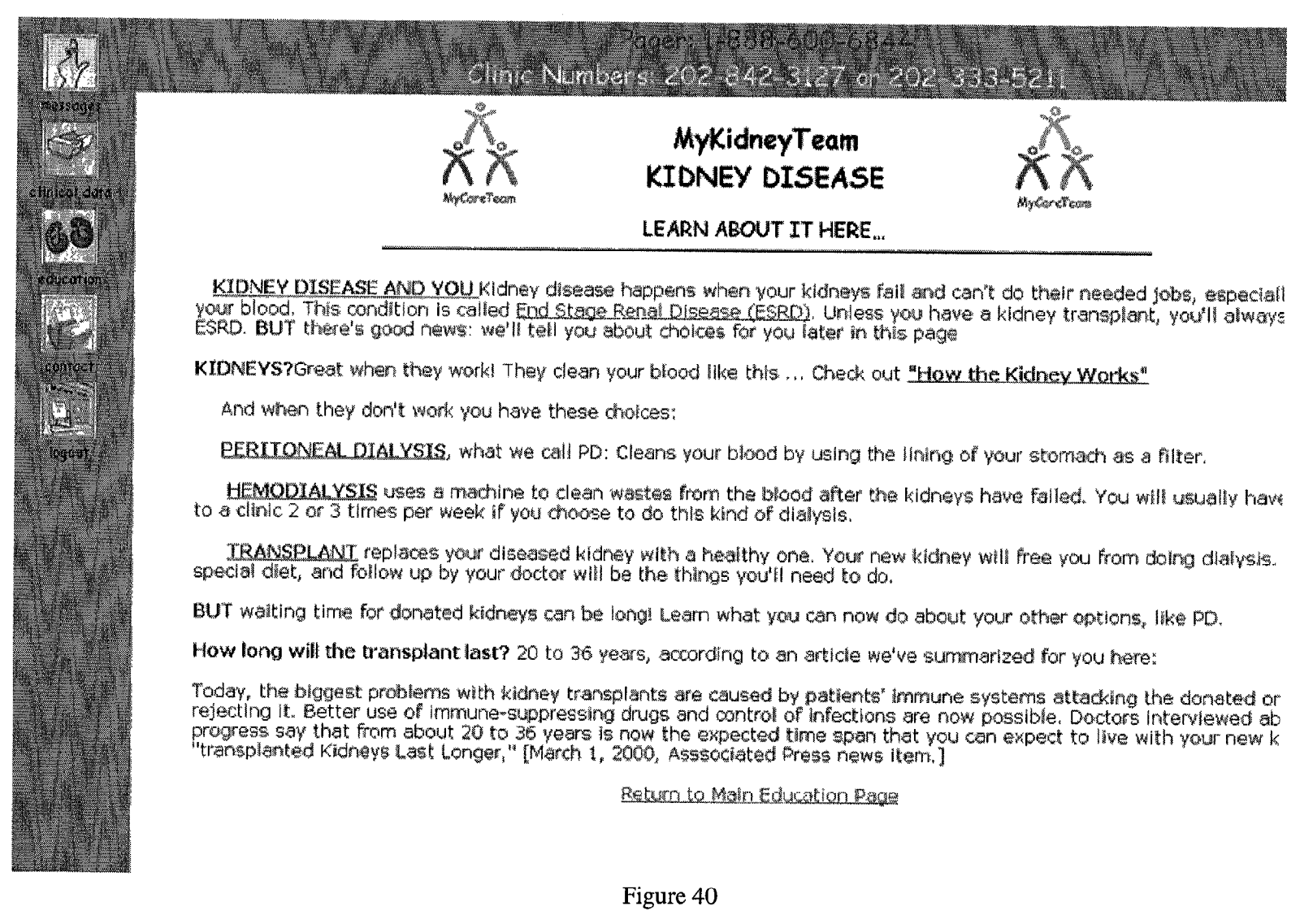

Selecting the underlined topic of "Kidney Disease and YOU" in FIG. 38 changes the screen to that shown in FIG. 40. Selecting an underlined word or phrase in the educational article of FIG. 40 may provide an on-screen contextually relevant message (not shown) that defines the word or phrase. By selecting the underlined, quoted article, " HowtheKidneyWorks" of FIG. 40, the system accesses a link to a Web site, for example, nephron.com, that explains the workings of the kidney to the patient. Selecting the underlined phrase "ReturntoMainEducationPage" allows the patient to return to the display of FIG. 38.

Selecting the underlined topic of "PD Doing It!, Plus: Problems and What YOU should know" in FIG. 38 changes the information displayed in the central display area to that shown in FIGS. 41A and 41B. Selecting an underlined word or phrase in the educational article shown in FIGS. 41A and 41B may provide an on-screen contextually relevant message (not shown) that defines the word or phrase. When other underlined sentences, such as, "Washing AND drying your hands—read about why it's so important here", of FIG. 41A are selected, an abstract of the article, "Washing AND drying your hands—read about why it's so important here", may be displayed, as shown in FIG. 42.

Figure 41A:
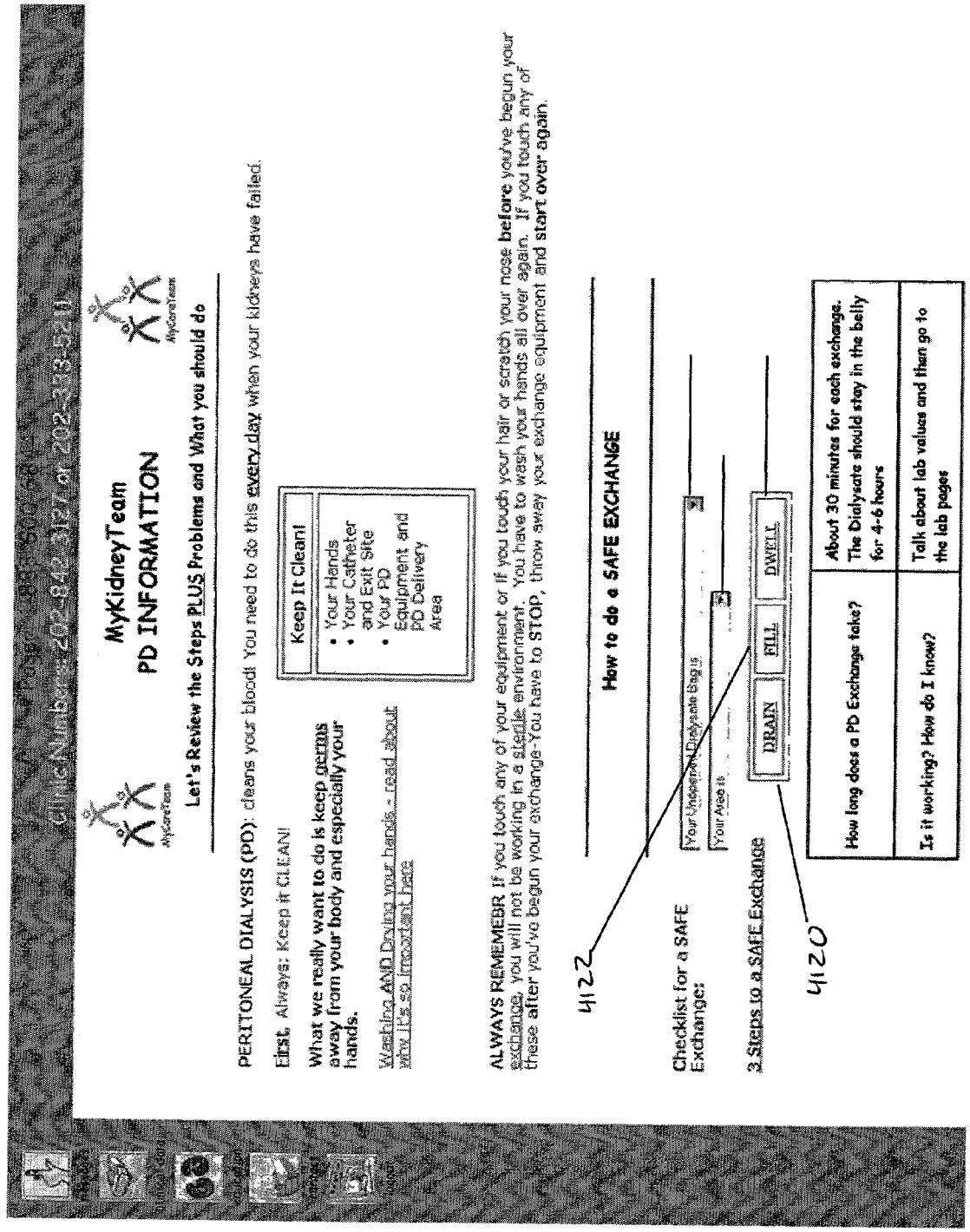
Figure 42:
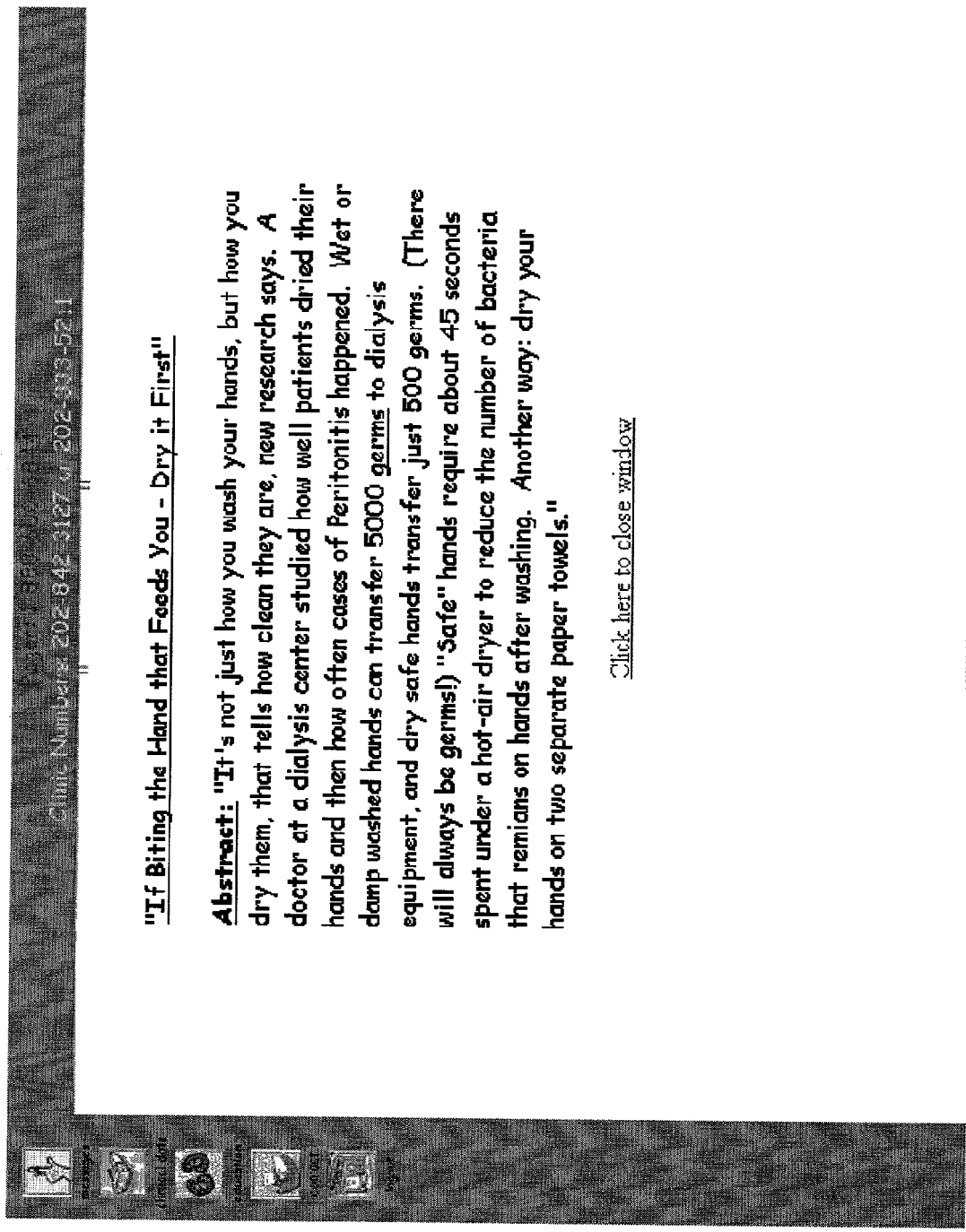
FIG. 42 shows one exemplary embodiment of a screen of a graphical user interface displaying an abstract of an educational article for patients having a chronic kidney illness according to this invention.

The section "PD INFORMATION" of FIG. 41A, entitled "How to do a SAFE EXCHANGE", may contain a drop down list box 4105, labeled "Your Unopened Dialysate Bag is", that provides a checklist 4310 for a patient to follow when checking his or her unopened dialysate bag to assure proper dialysis technique, as shown in FIG. 43. Similarly, selecting the drop down list box 4110, labeled "Your area is", provides a checklist 4410 for the area the patient selects for his or her peritoneal dialysis, as shown in FIG. 44.

Figure 45A:
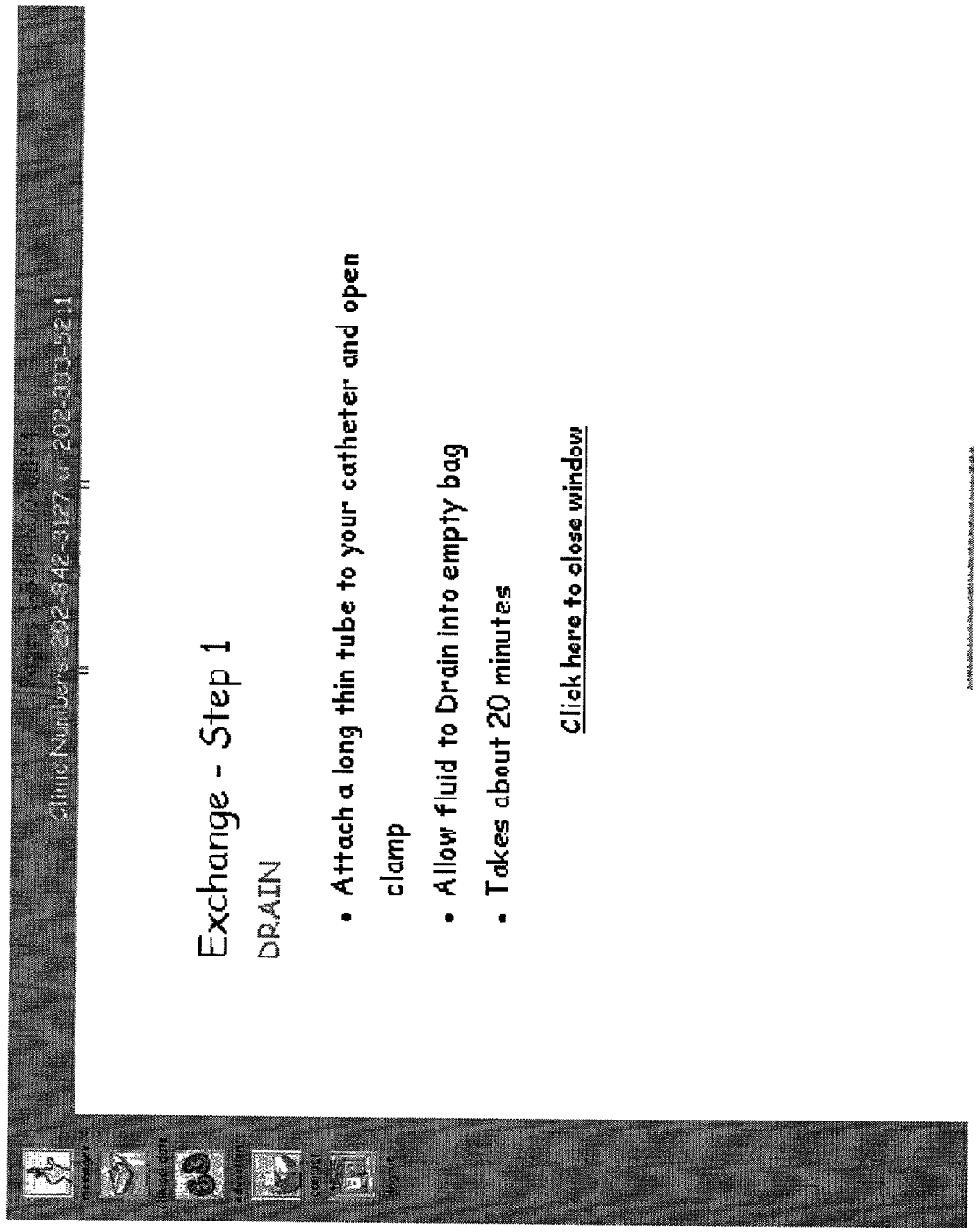
Figure 45B:
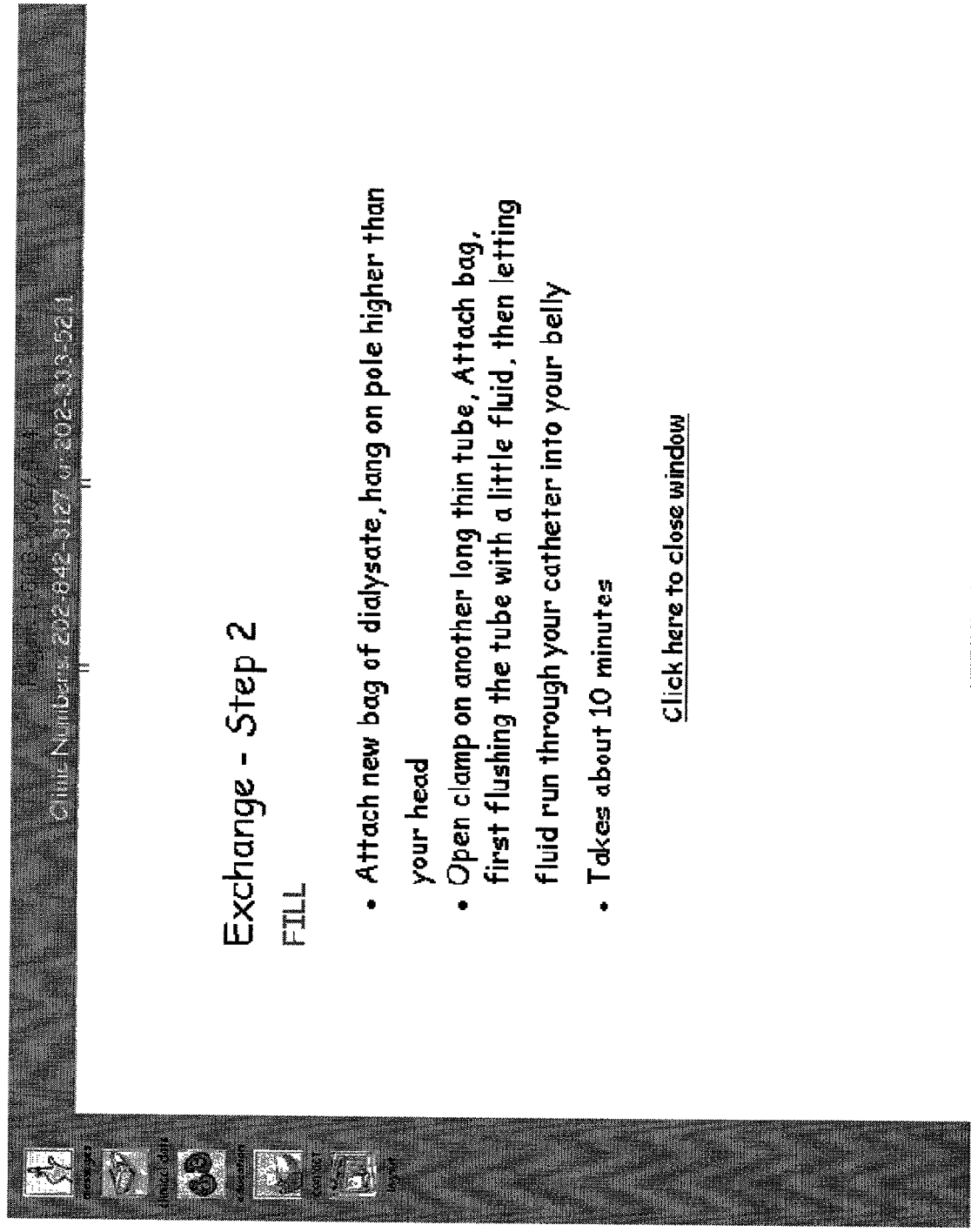
Figure 46A:
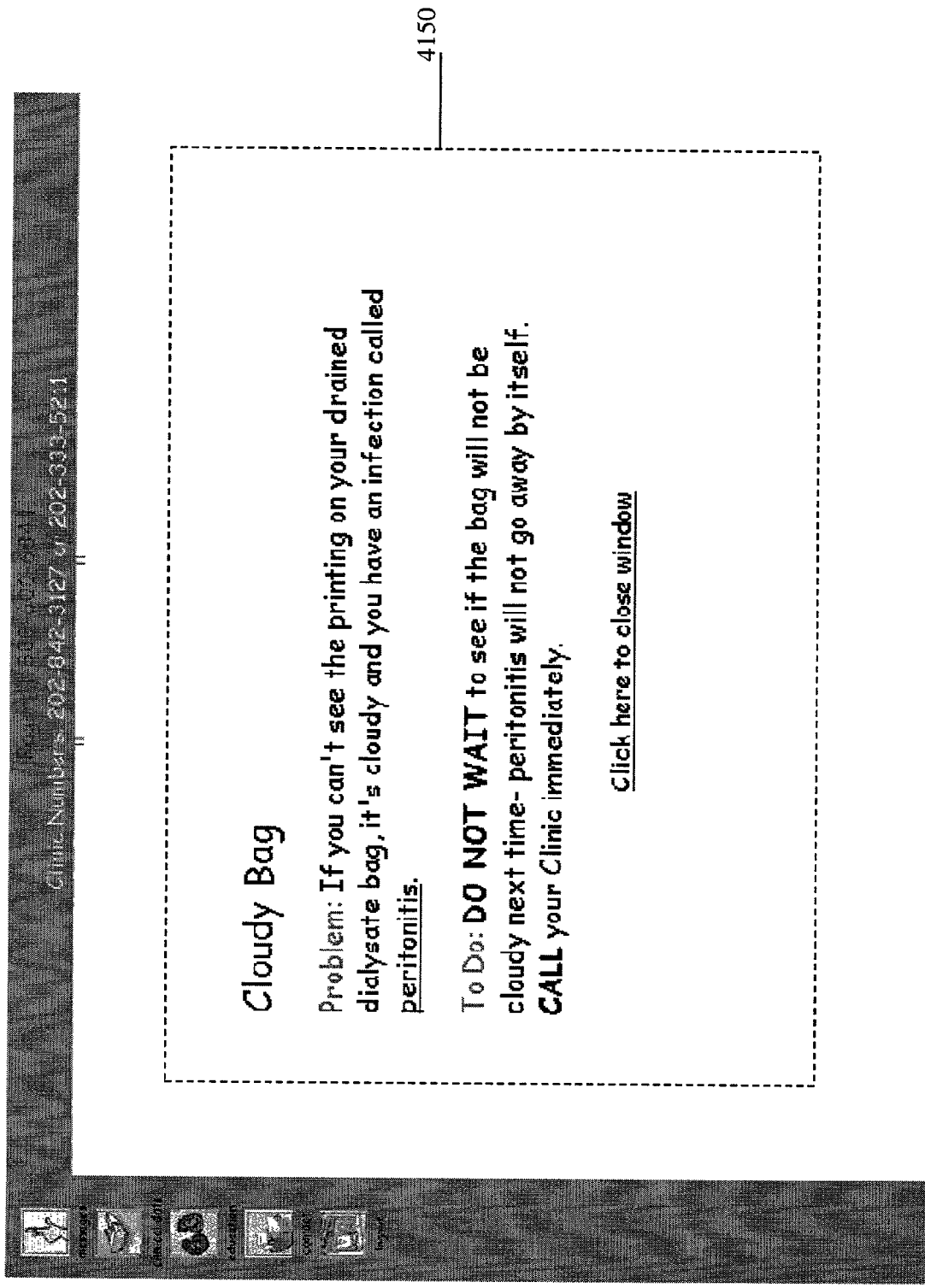
Figure 46B:
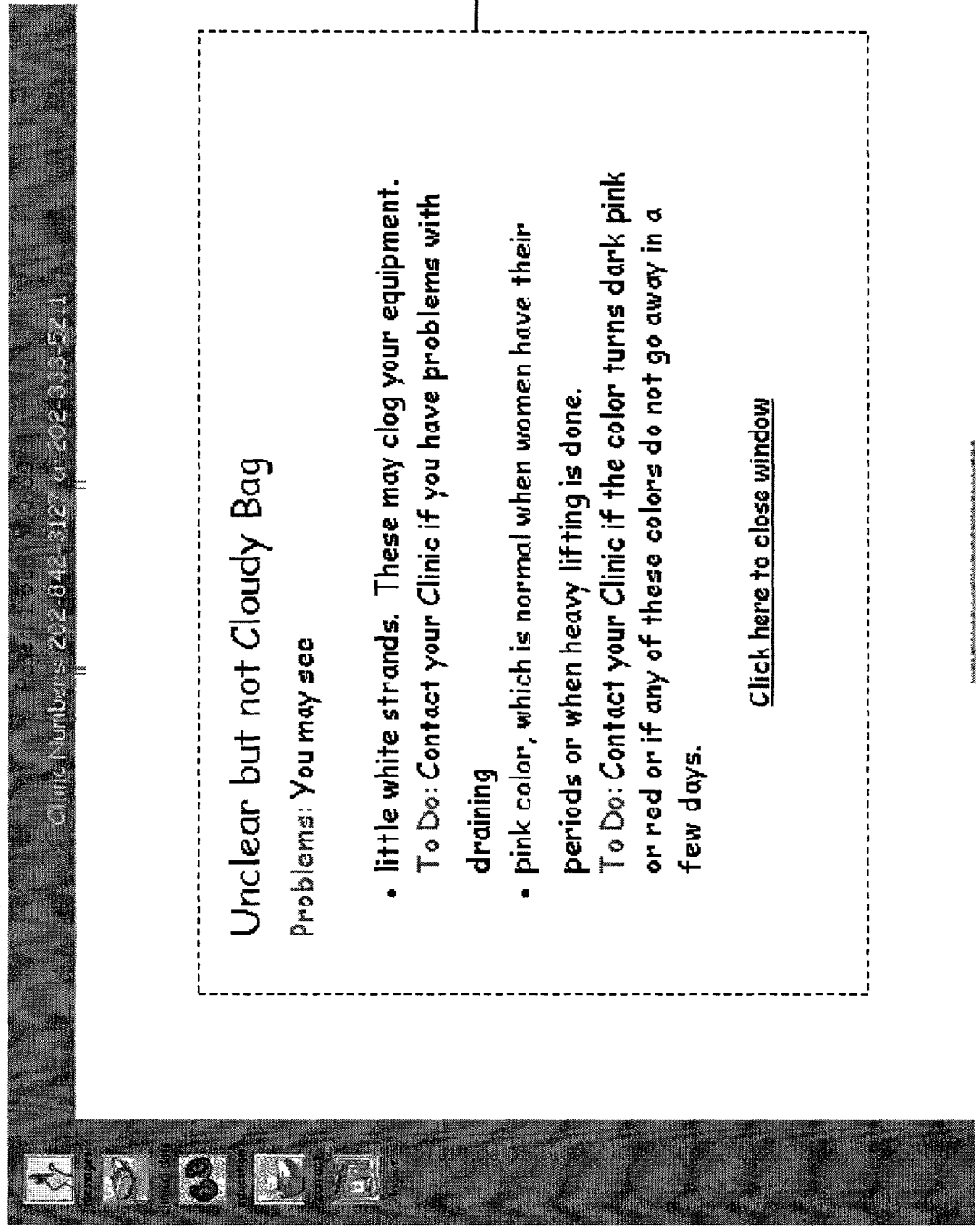
Figure 46C:
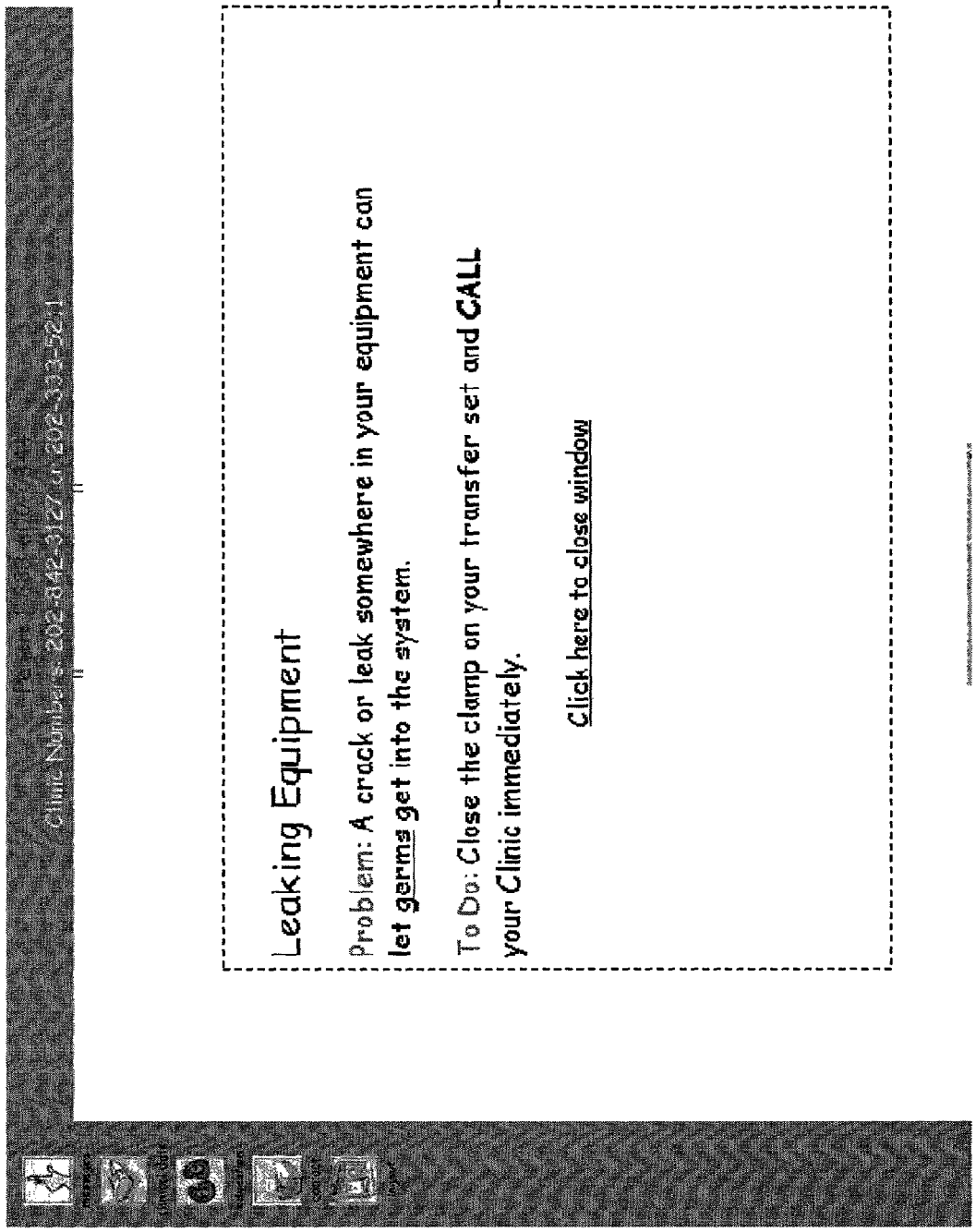
Figure 46D:
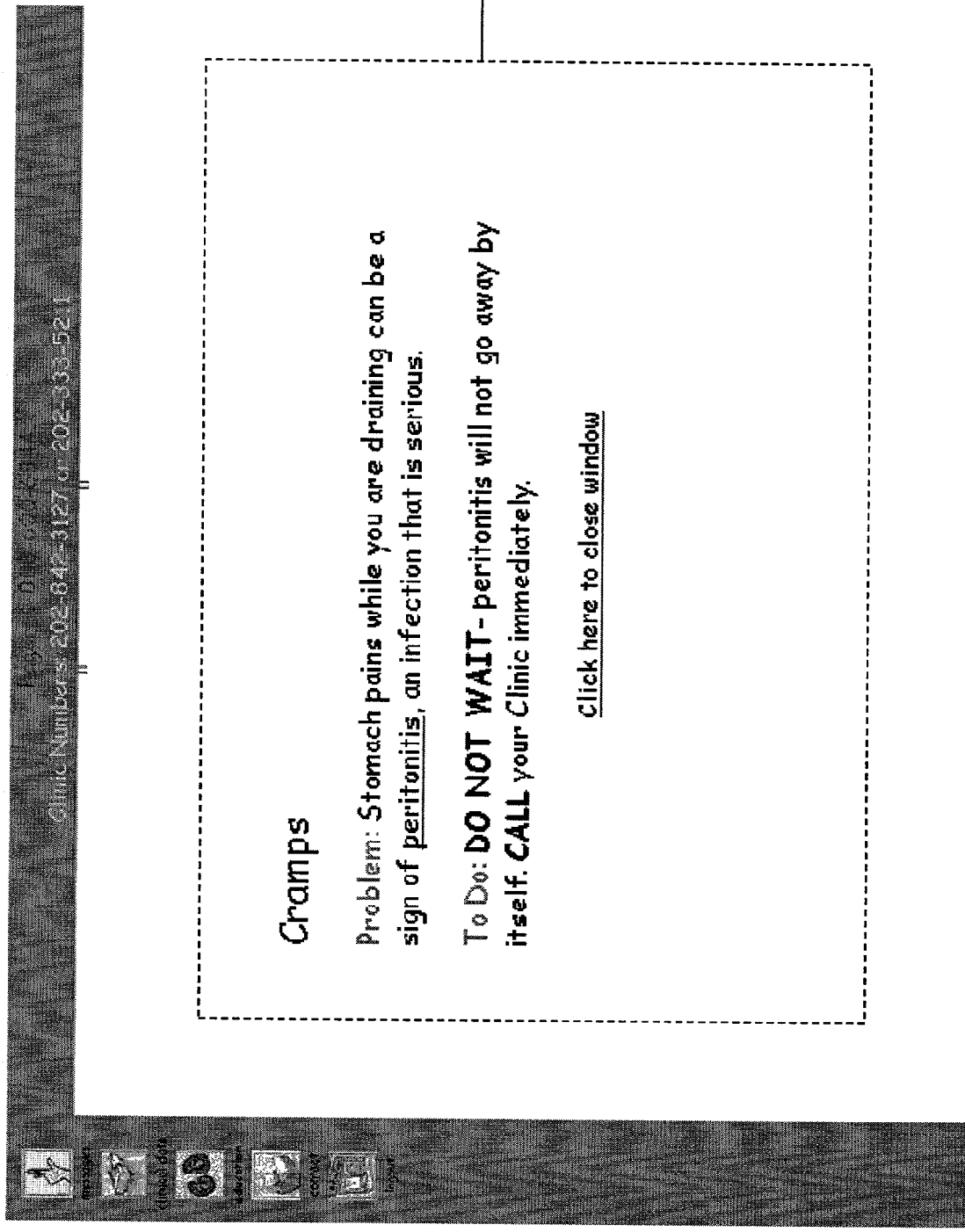
Figure 46E:
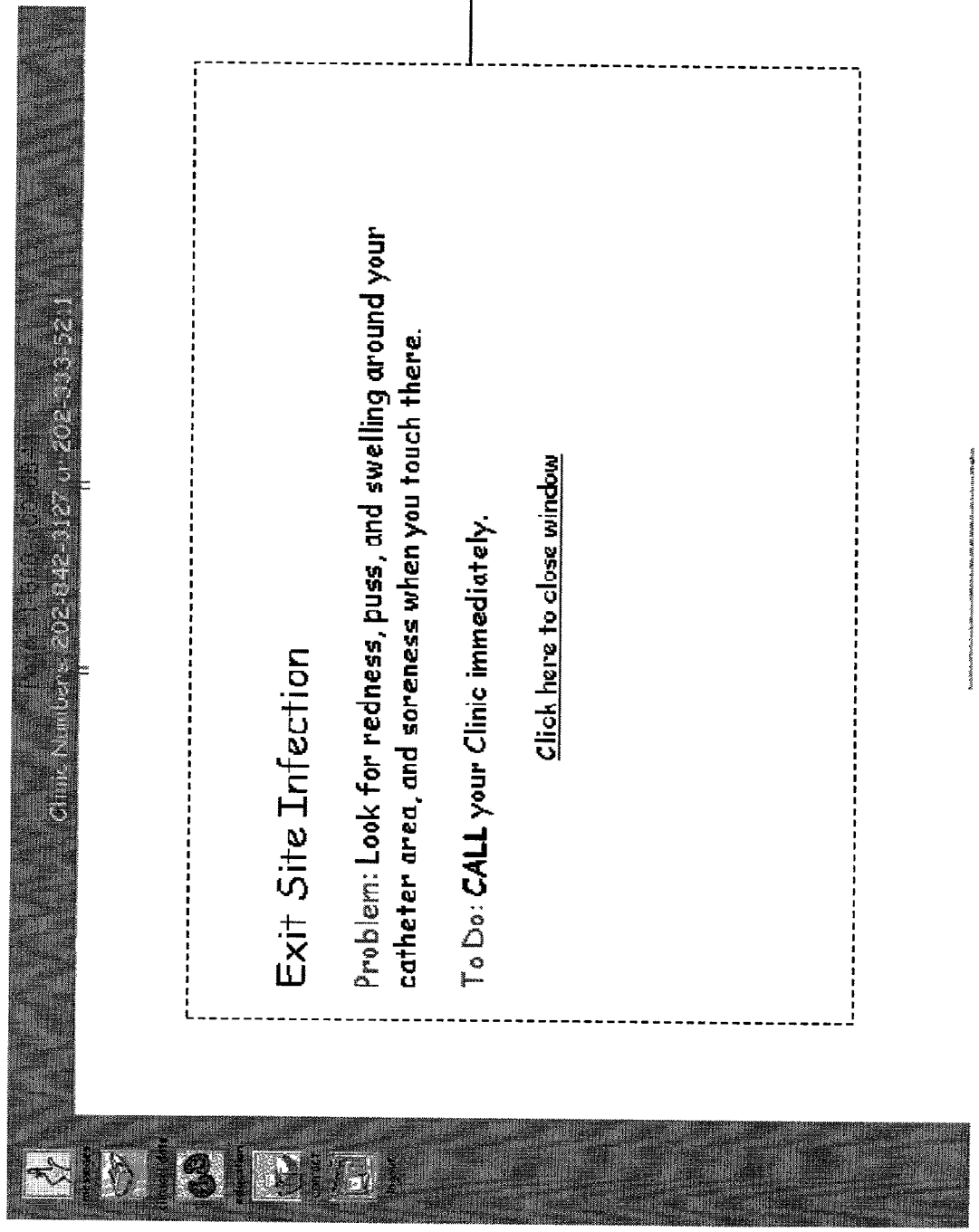

The section of "PD INFORMATION" of FIG. 41A, entitled "3StepstoaSAFEExchange", shows three underlined terms, that is, "DRAIN" 4120, "FILL" 4122 and "DWELL" 4124 in a horizontal row. Selecting an underlined term changes the screen to show the information concerning the selected underlined term, as shown for "DRAIN" 4120, " FILL" 4122 and "DWELL" 4124, in FIGS. 45A-45C, respectively. After reading any of the "3StepstoaSAFEExchange" in FIGS. 45A-45C, the patient may return to section entitled " 3StepstoaSAFEExchange" of FIG. 41A by selecting the phrase, "Click here to close window".

The section of "PD INFORMATION" of FIG. 41B, entitled "Problem List", shows five underlined phrases, that is, "Cloudy Bag" 4150, "Unclear but not Cloudy Bag" 4152, "Leaking Equipment" 4154, "Cramps" 4156. and "Exit Site Infection" 4158 in a horizontal row. Selecting an underlined phrase changes the screen to show the information concerning the underlined phrase, as shown for "Cloudy Bag" 4150, "Unclear but not Cloudy Bag" 4152, "Leaking Equipment" 4154, "Cramps" 4156, and "Exit Site Infection" 4158, in FIGS. 46A-46E, respectively. After reading about any of the problems of peritoneal dialysis, the patient may return to the section entitled "Problem List" of FIG. 41B by selecting the phrase, "Click here to close window".

Figure 47A:
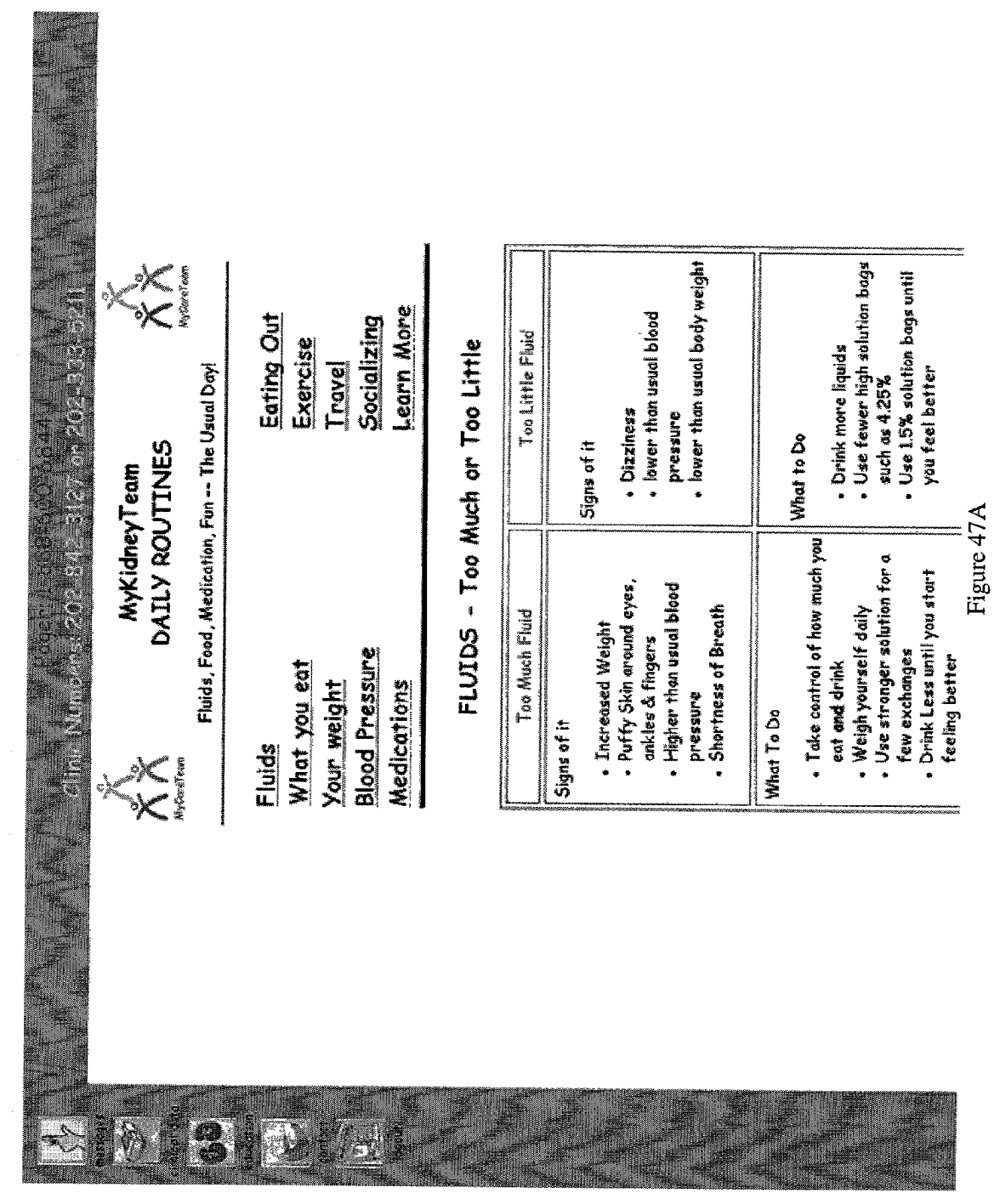
Figure 47D:
Figure 47E:
Figure 47H:

Selecting the underlined topic of "Daily Life, Food, Fluids, Meds and FUN" of FIG. 38 changes the information displayed in the central display area to that shown in FIGS. 47A-47I. The underlined topics presented under the "Daily Routines" of FIG. 47A may include but are not limited to " Fluids", "Whatyoueat", "Yourweight", "BloodPressure", " Medications", "EatingOut", "Exercise", "Travel", " Socializing", and "LearnMore". In FIG. 47A, selecting any of the underlined topics listed presents an on-screen contextually relevant message between the two columns of underlined topics. For example, FIG. 48 shows the contextually relevant message of "Here are some Tips" 4810 when the underlined topic of "EatingOut" is selected. Additionally, on-screen contextually relevant messages may be displayed for underlined words and phrases within the displayed texts of the underlined topics, shown in FIGS. 47A-47I. Links to other web sites, concerning kidney disease, may also be located within the texts of the underlined topics, shown in FIGS. 47A-47I. At the bottom of the text of each underlined topic, shown in FIGS. 47A-47I is an underlined phrase "ReturntoTop" that when selected returns the patient to the top of "Daily Life, Food, Fluids, Meds and FUN" shown in FIG. 47A.

Figure 49:
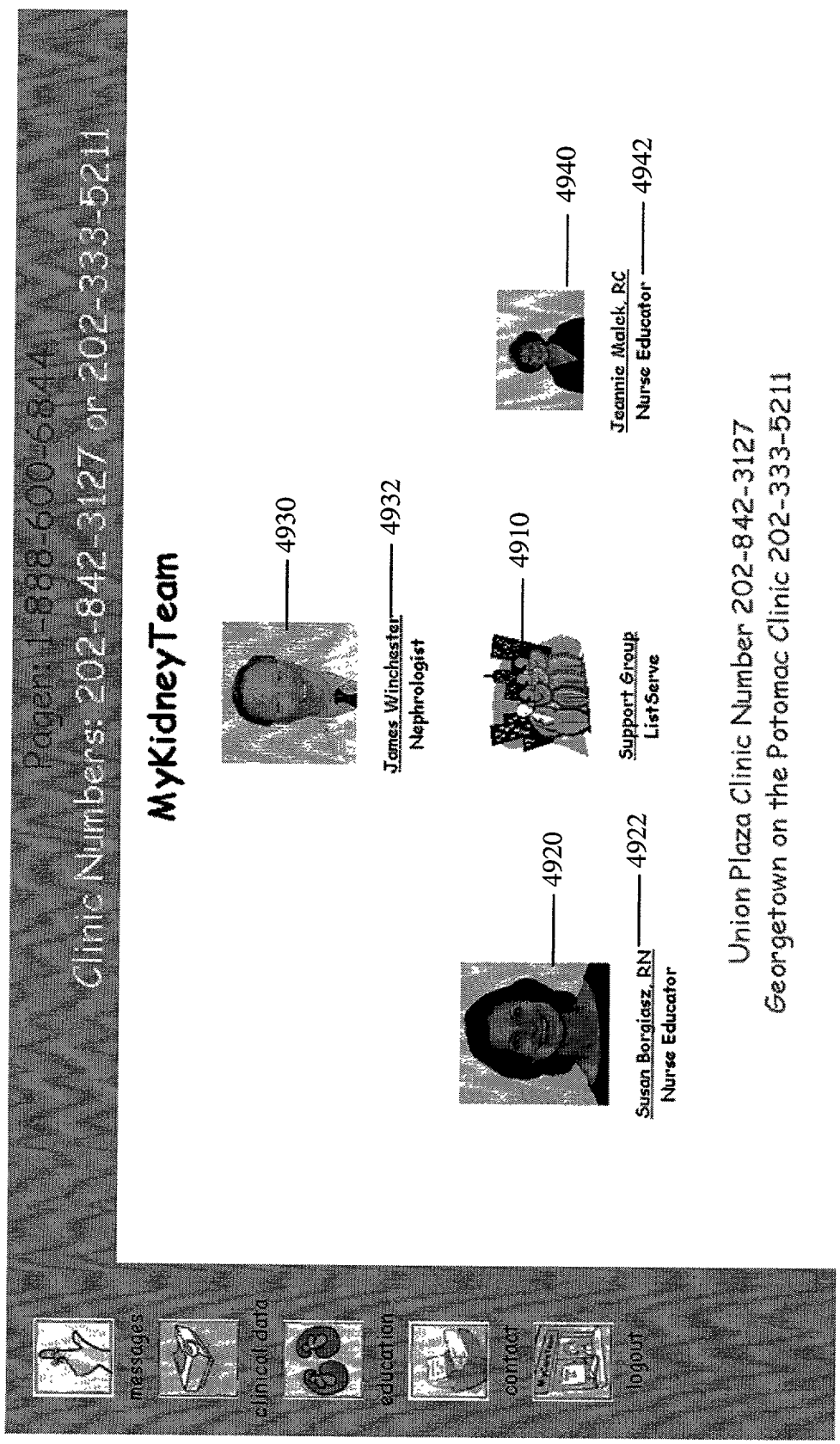
FIG. 49 shows one exemplary embodiment of a screen of a graphical user interface that enables access to the patient's healthcare practitioners over a distributed network according to this invention.

When a kidney disease patient selects the "contacts" icon 3238 of FIG. 32 or any other patient screen having a green frame 3202, the screen changes to that of a graphic and pictorial representation of the clinic's kidney disease treatment and monitoring team, as shown in FIG. 49. If the patient selects a team member's picture icon 4920-4940, a short biographical sketch (not shown) of the team member may appear on the screen. This biographical sketch helps to familiarize the patient with the clinicians handling the patient's case. If the email access icon 4922-4942 is selected, a dialog box containing the corresponding email or message address of the selected team member where that team member can be reached is displayed. If the patient selects the "Support Group" 4910 icon, the screen may show a dialogue box (not shown) containing the support group's e-mail or message address where the patient may chat with others having the same chronic illness.

Figure 50:
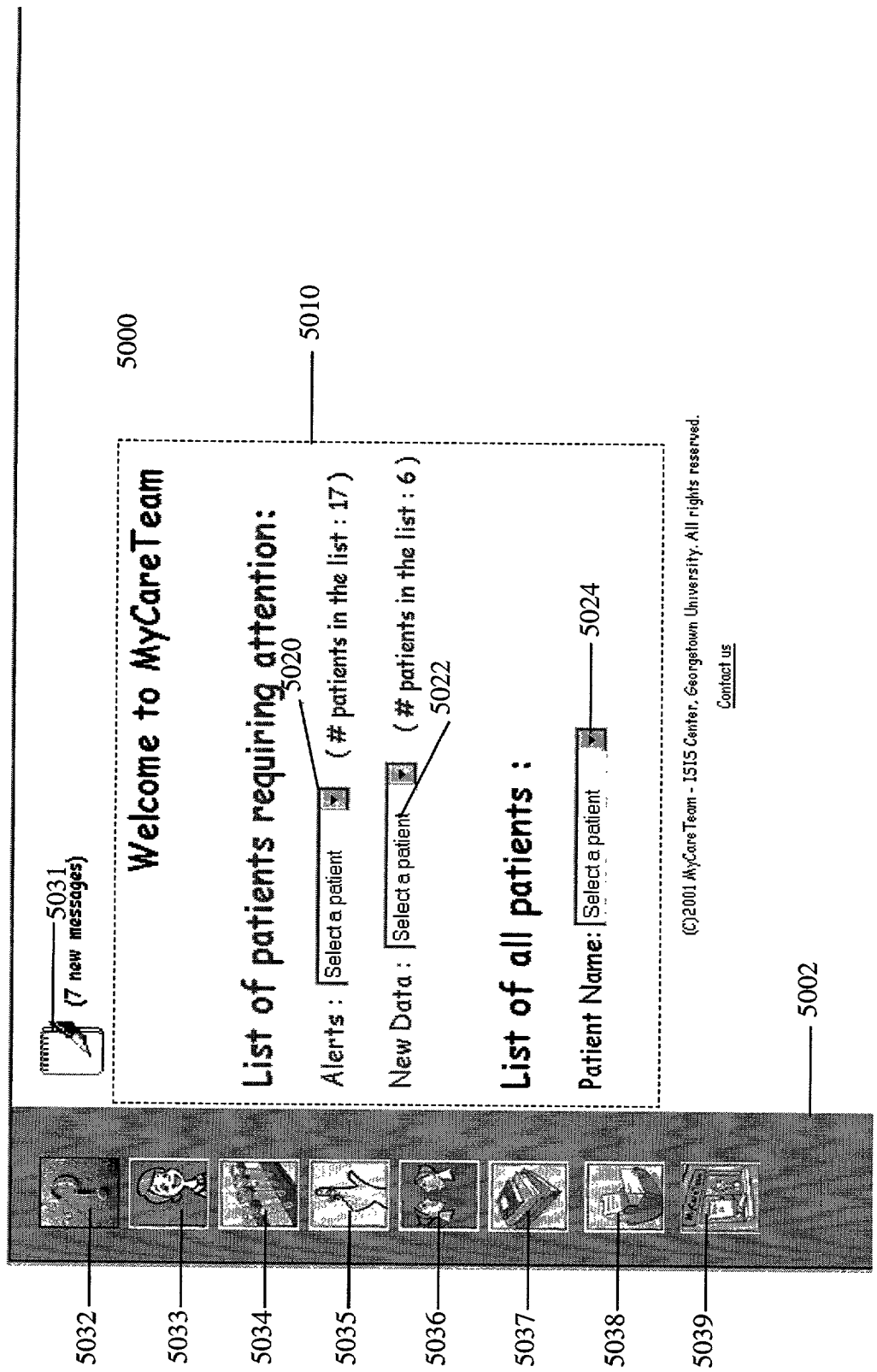
FIG. 50 shows one exemplary embodiment of a screen of a graphical user interface usable by a healthcare practitioner to access a patient's healthcare records according to this invention.

When an authorized healthcare practitioner of the clinic signs into the clinic by entering his or her name and a password on the clipboard shown in FIG. 7, the screen automatically changes to display information concerning the practitioner's patient selection in the central display area 5010 of the main practitioner data screen's 5000, as shown in FIG. 50. Information concerning the practitioner's patient selection may also be displayed by selecting the animated "alerts and reminders" 5032 icon. The background 810 of the left side border of the frame 5002 may be, for example, blue, indicating that the practitioner's patient selection is for those patients enrolled in the diabetes clinic, green, indicating that the practitioner's patient selection is for those patients enrolled in the kidney disease clinic, or another color for some other chronic illness or related clinic. In FIG. 50, for the practitioner's patients within the diabetes clinic, the main practitioner data screen 5000 can include a message list icon 5031, while the left side border of the frame 5002 may include, for example, icons for "alerts and reminders" 5032, "register patients or practitioners" 5033, "enter patient's lab results" 5034, "patient reminders" 5035, "On-line chatroom" 5036, "education" 5037, "contacts" 5038, and "logout" 5039, that change the information displayed in the central display area of the main practitioner data screen. When selected, each of the icons 5031-5039 may be identified by an on-screen contextually relevant message when the on-screen indicator is placed over that icon. Additionally, a cumulative count of new messages for the healthcare practitioner from all of the patients of that healthcare practitioner can be presented on this screen, for example, located on the message list. A link to the messaging screen 7100 is provided by the message list icon 5031 attached to the count.

The central display area 5010 of the main practitioner data screen 5000 is used by a healthcare practitioner to select a patient whose data the healthcare practitioner would like to review. As shown in FIG. 50, there are three lists of patients the healthcare practitioner can select a patient from. A first, an all patients list box 5024 lists all patients. A second, or alerts list box 5020, lists only those patients to whom alerts have been sent. A third, or new data list box 5022, lists only those patients that have submitted new data, such as, for example, blood glucose data, peritoneal dialysis data or clinical data from other chronic illness monitor device.

Selecting a patient's records for review by the healthcare practitioner may be prioritized by allowing the healthcare practitioner to choose patient records listed in, for example, the alerts list box 5020, that contains a list of those patients to whom alerts have been sent. For example, in various exemplary embodiments, such as that shown in FIG. 50, patients are prioritized based on those requiring attention and among all patients. Those patients requiring higher priority attention include those with active alerts and those with new data. The patients with active alerts and/or new data appear in the alerts list box 5020 or new data box 5022 and the label for the alerts list box 5020 is presented in red. New data, for example, includes blood glucose data (for a diabetic patient) sent in that has not been reviewed by a healthcare practitioner and lab data that has not been reviewed. Selecting a patient from the list contain in the alerts list box 5020 or new data box 5022 brings up the messages screen 5100, shown in FIG. 51, for that patient, displaying the alerts contained in the alerts list box 5020, any messages, and reminders sent to that patient. This also removes that patient from the list contained in the alerts list box 5020 and the new data box 5022.

In various exemplary embodiments, the reasons for alerts may include, for example, one or more of the average blood glucose level being greater than site/patient configurable value, the number of days since receiving new data being greater than site/patient configurable value, the HbA1C value being greater than site/patient configurable value, more than 3 hypoglycemic events having occurred within site/patient configurable time frame, and/or more than 6 hyperglycemic events having occurred within site/patient configurable time frame.

Additionally, patients are prioritized based on new data and appear in the new data list box 5022 with the label for the box presented in green. Selecting a patient from this list brings up the messages screen 5100, shown in FIG. 51A, for that patient. The messages screen 5100 displays that patient's alerts, messages, and reminders and removes that patient from the alert list box 5020 and the new data list box 5022. All patients assigned to the healthcare practitioner appear in the all patients list box 5024 and the label for all patients list the box is 5024 presented in blue. Selecting a patient from this list brings up the patient's log book as the initial screen, but does not remove that patient from the list contained in the alerts list box 5020 or the new data list box 5022 if that patient is contained in that list.

Figure 51A:
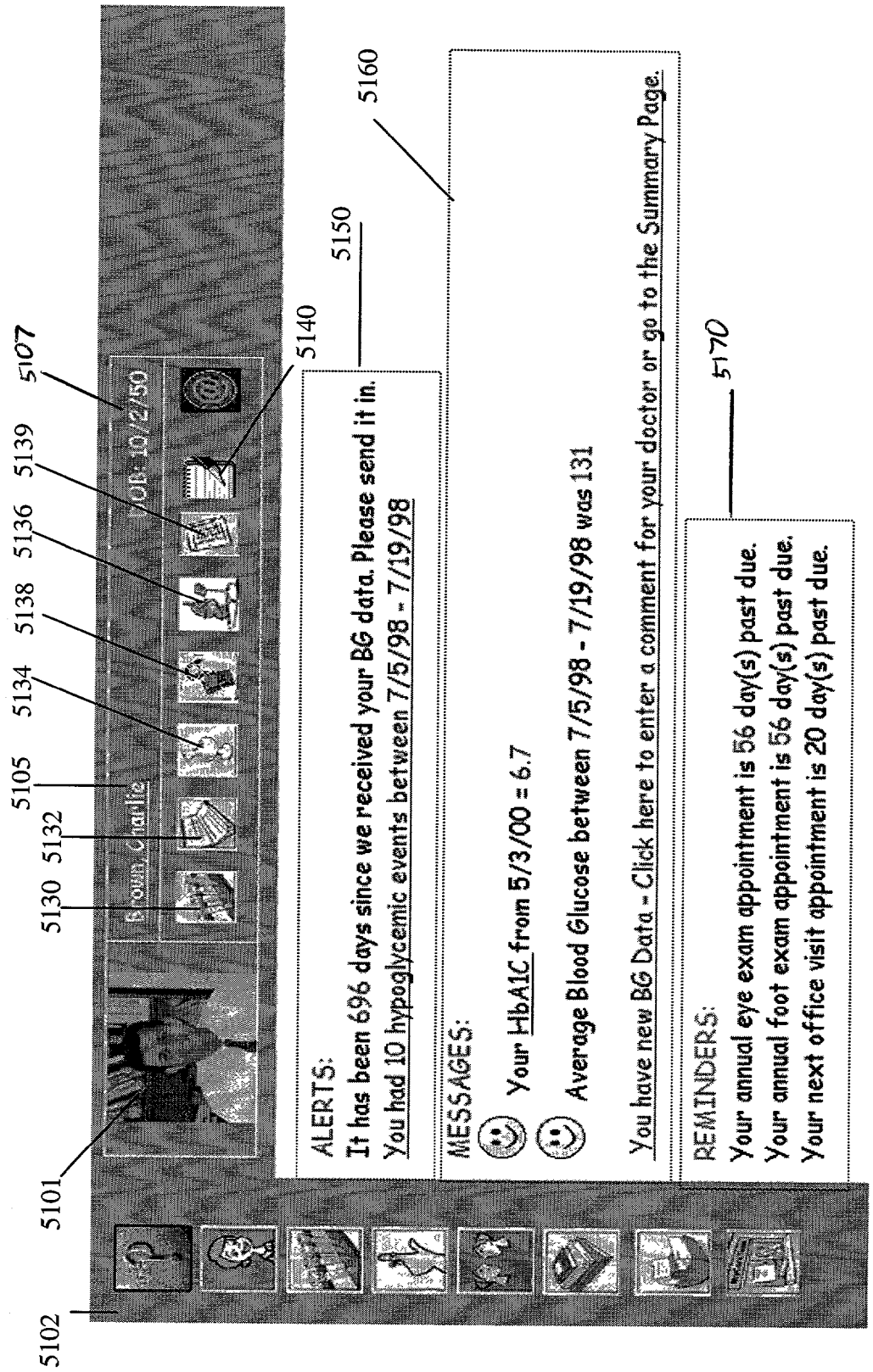
FIGS. 51A and 51B show various exemplary embodiments of a practitioner screen of a graphical user interface usable to display various exemplary embodiments of alerts, messages and reminders according to this invention.
Figure 51B:
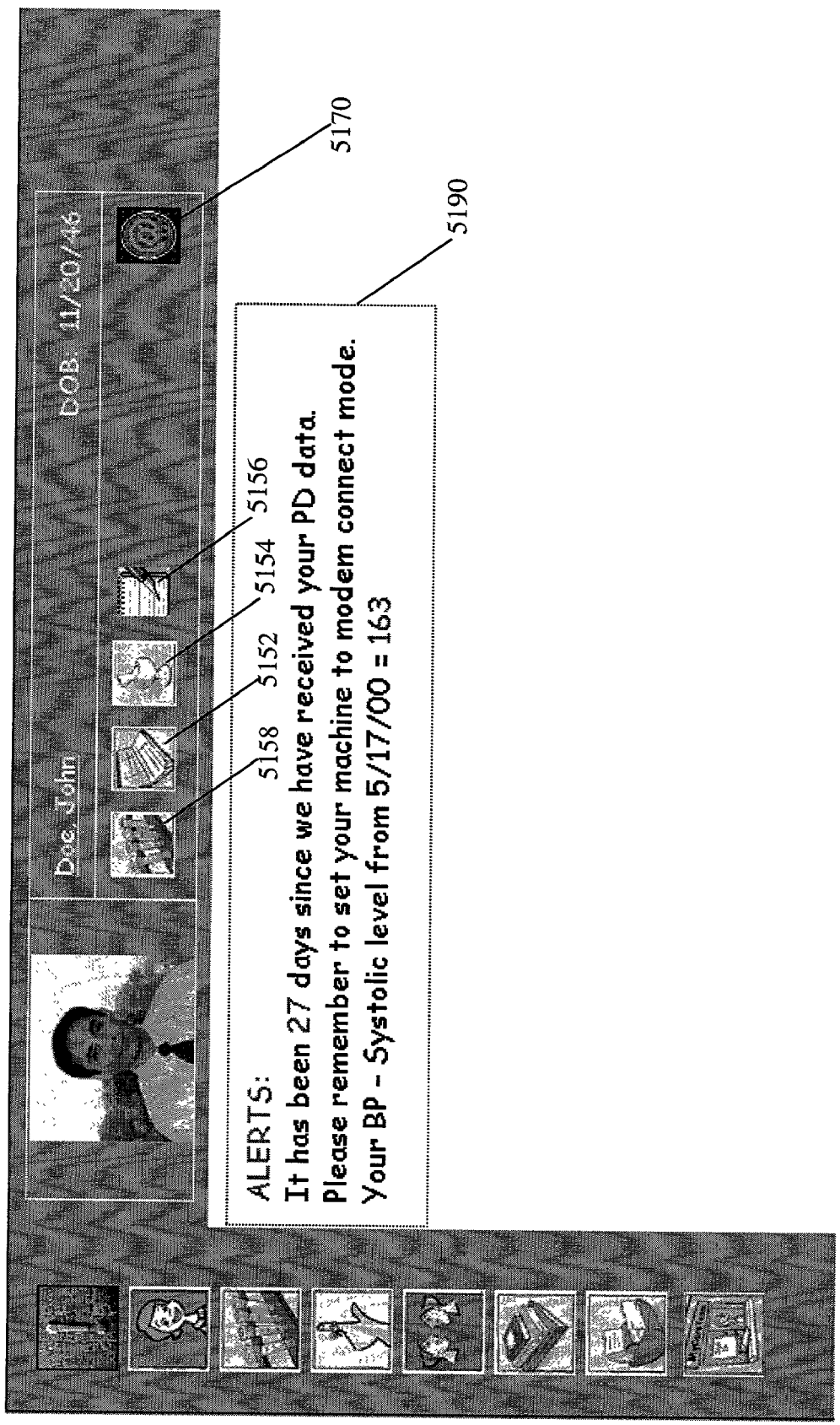

After selecting a patient's name from the list of patients contained in the alerts list box 5020 or the new data list box 5022, information concerning "ALERTS:" 5150, "MES- SAGES:" 5160 and "REMINDERS:" 5170 for the selected patient is displayed, as shown in FIG. 51A for a diabetic patient, and for "ALERTS:" 5190, as shown in FIG. 51B for a kidney disease patient. Alternatively, the healthcare practitioner may select patient records from, for example, the all patients list box 5024, as shown in FIG. 50.

In FIG. 51A, the upper border of the frame 5102 for diabetic patients may include a patient's picture 5101, the patient's underlined name 5105, date of birth 5107, and icons accessing the diabetic patient's "Lab Results" 5130 (see FIG. 21), "Blood Sugar Log" 5132 (see FIG. 15), "Medication" 5134 (see FIG. 22), "Blood Pressure Log" 5138 (see FIG. 25), "Exercise Log" 5136 (see FIG. 24), "Data Summary and Healthcare practitioner Comments" 5139 (see FIG. 26) and "Message List" 5140 (see FIG. 68) as described above for information displayed for diabetic patients. In FIG. 51B, the icons access the kidney patient's "Lab Results" 5158 (see FIG. 36), "Automated Cycler Flow Sheet" 5152 (see FIG. 34), and "Medications" 5154 (see FIG. 37) and the message list 5156. Selecting the patient's picture 5101 automatically presents a screen that allows the healthcare practitioner to send a message to the patient. When the on-screen indicator is placed over the primary care healthcare practitioner's icon 5170, the patient's primary care healthcare practitioner is identified by name. Selecting the primary care healthcare practitioner's icon 5170 may connect the clinic healthcare practitioner to the patient's primary care healthcare practitioner by automatically providing a screen which allows the clinic healthcare practitioner to send a message to the patient's primary care healthcare practitioner.

Figure 52:
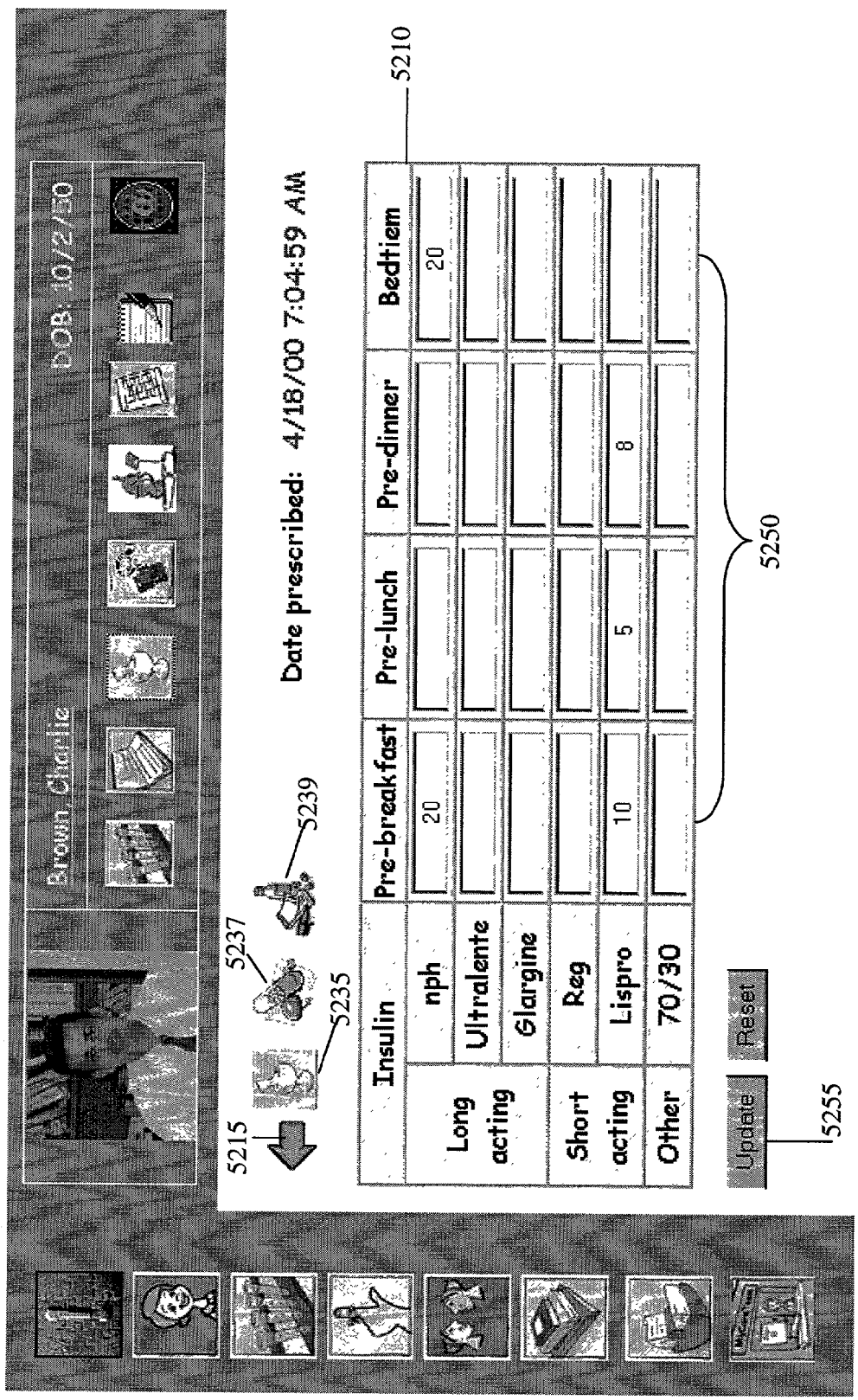

Selecting the "Medication" icon 5134 for the diabetic patient of FIG. 51A automatically changes the information displayed to an insulin prescription table 5210, a number of icons located above the insulin prescription table 5210 and the date the medication is being prescribed, as shown in FIG. 52. These icons include an insulin medication icon 5235, an oral medication icon 5237 and an other medications icon 5239. The date insulin is prescribed and the insulin prescription table 5210 is also displayed by selecting the insulin medication icon 5235, which is identified by an on-screen message when the on-screen indicator is placed over the insulin medication icon 5235. The patient's clinic healthcare practitioner may review previous insulin prescriptions by selecting the left-facing arrow 5215, which is identified by the on-screen message of "previous prescription" when the on-screen indicator is placed over the arrow 5215. After reviewing a previous insulin prescription, the healthcare practitioner may advance the prescription date and the insulin prescription table 5210 by selecting a right-facing arrow (not shown), which is identified by the on-screen message of "next prescription" when the on-screen indicator is placed over the right-facing arrow.

The healthcare practitioner enters a new insulin prescription for the diabetic patient into the insulin prescription table 5210 of FIG. 52 by entering data into, for example, data input entry boxes 5250, from the healthcare practitioner's data terminal 130. After entering data for a new prescription into the insulin prescription table 5210, the healthcare practitioner may select the "Update" button 5255 to create the new prescription table, which is automatically dated and timed at the time of the updated entry.

Figure 53:
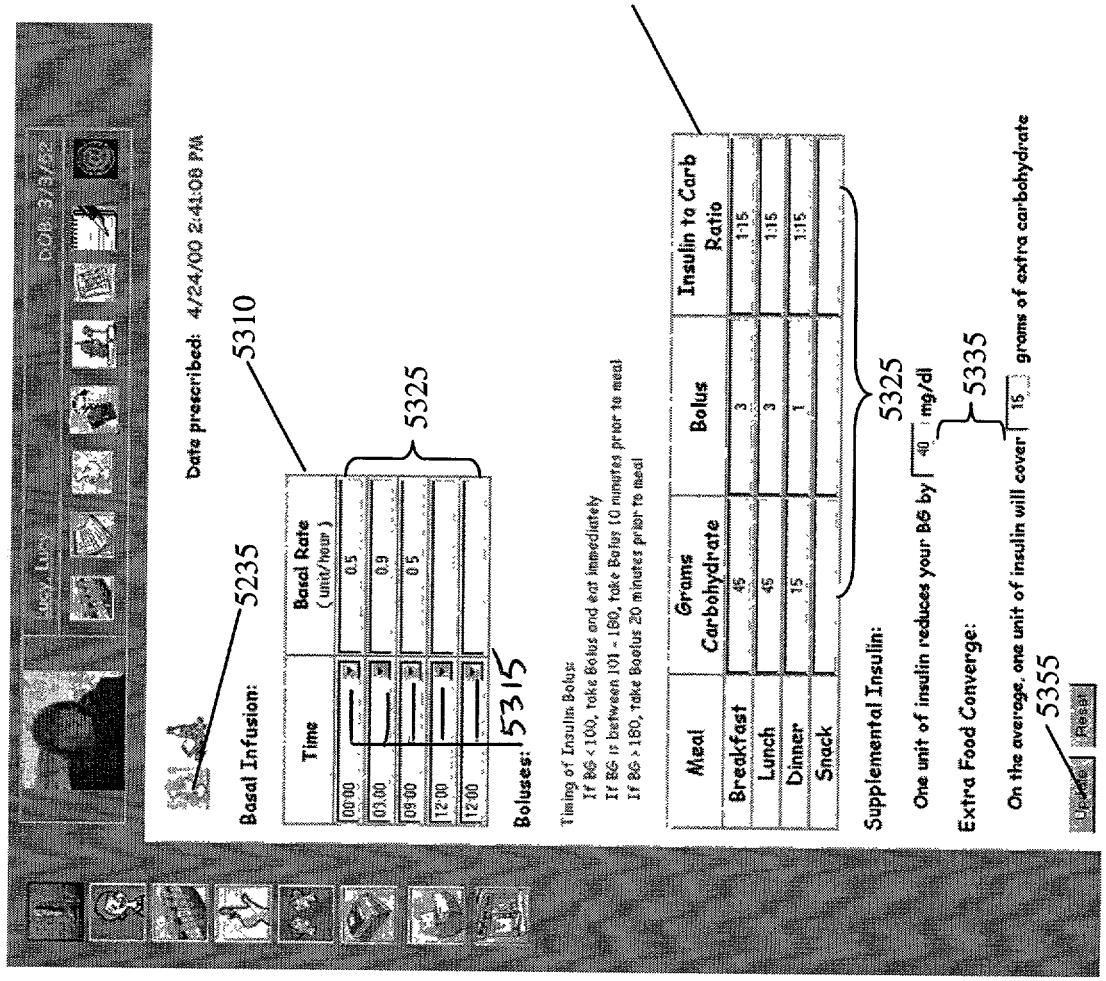
FIG. 53 shows one exemplary embodiment of a screen of a graphical user interface displaying insulin pump information to a practitioner according to this invention.

For diabetic patients having an insulin pump, the information displayed upon selection of the insulin medication icon 5235 automatically shows a basal infusion data table 5310, a meal/bolus table 5320, and information relating to supplemental insulin and extra food convergence, as shown in FIG. 53 The healthcare practitioner enters the new insulin pump prescription data into the basal infusion data table 5310 and meal/bolus table 5320 by, for example, drop down list boxes 5315 or data entry input boxes 5325, and the data relating to supplemental insulin and extra food convergence into their, for example, data entry boxes 5335. To create a new insulin pump prescription, the healthcare practitioner may select the "Update" 5355 button at the bottom of the display of FIG. 53.

Figure 55:
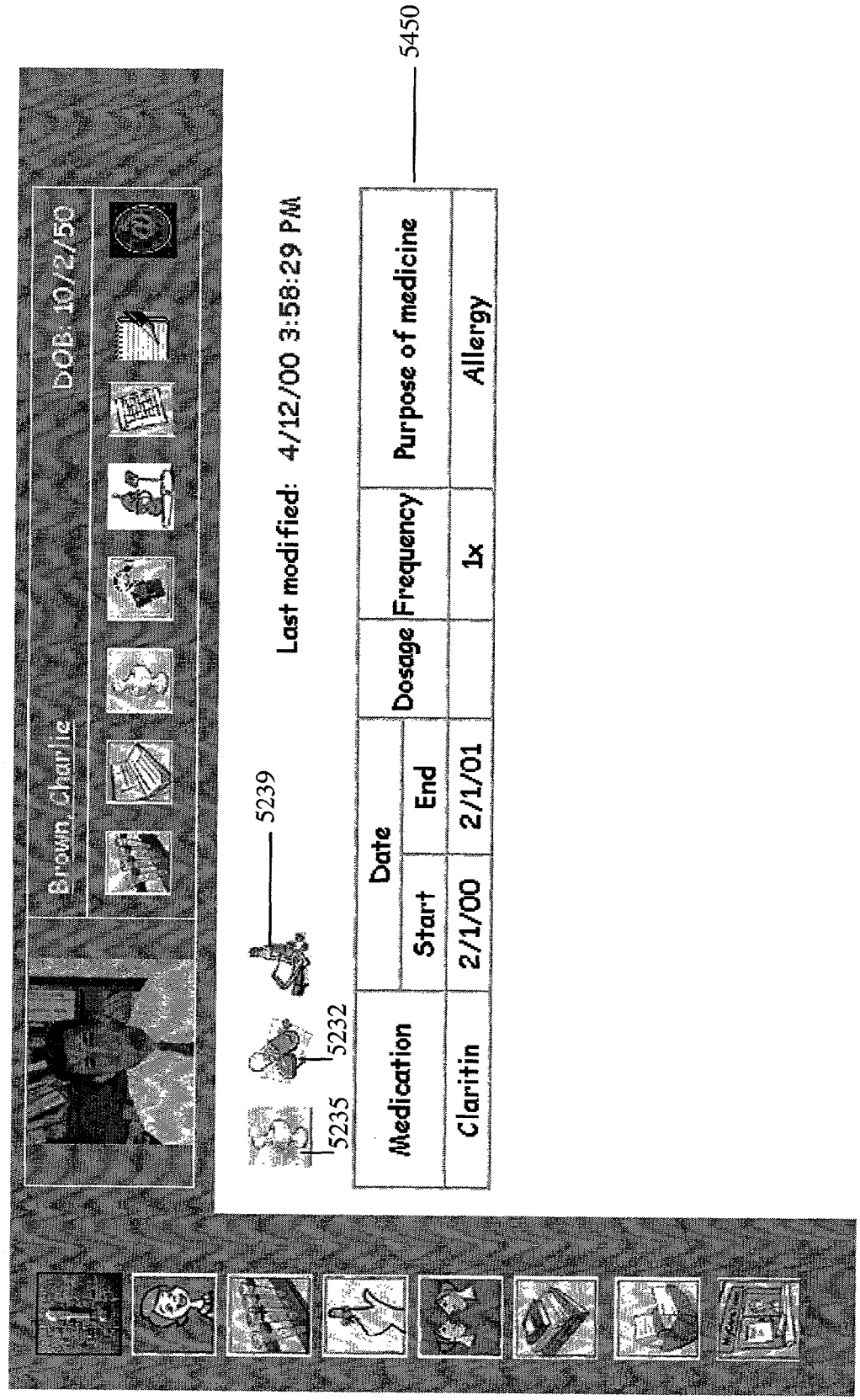

Selecting the oral medications 5237 icon, for diabetic patients, located above the insulin prescription table 5210 of FIG. 52, automatically changes the information displayed to a prescription date for oral medications and an oral medication prescription table 5410, as shown in FIG. 54. The healthcare practitioner may review previously prescribed oral medications by selecting the left-facing arrow 5415 and after review may return to the current oral medication prescription table 5410 by selecting the right-facing arrow (not shown), as described above. Entry of the new oral prescription information may be facilitated by prescribing drugs that are categorized by their function, for example, drugs which enhance insulin secretion, a drug which decreases glucose production by the liver, drugs which slow the absorption of sugars, and glitazones. Entry of data into the oral prescription table 5410 may also be facilitated by allowing the healthcare practitioner to rapidly select a particular drug within a functional category of drugs and to enter prescription information, for example, dosage, tablets per dose and frequency taken, into an appropriate, for example, drop down list box 545, as shown in FIG. 55 For example, a 500 mg dose of the drug, Glucophage, may be entered into the drop down list box 5450, as shown in FIG. 54.

Selecting the Medications icon 5154 for kidney disease patients, of FIG. 51B, automatically changes the information displayed to a "Medications" table 3710 and "Other Medications" table 3720, as described above and shown in FIG. 37. The healthcare practitioner may enter new prescriptions for medications by entering the appropriate data into the "Medications" table 3710 by, for example, a number of data entry input boxes (not shown), corresponding to the "Medications" table's 3710 data. The healthcare practitioner may, similarly, view the appropriate data entered by the patient into the "Other Medications" table 3720.

Selecting the "Other medications" icon 5239 of FIG. 52 automatically changes the information displayed to the "Other medications" table 5450, which corresponds to the diabetic patient's "Other medications" table 1730 or 1732, shown in FIG. 22, for a practitioner selected diabetic patient and to the kidney disease patient's "Other medications" table 3720, shown in FIG. 37, for a practitioner selected kidney disease patient. These other medications may be non-prescription medications or they may be medications that have been prescribed by other healthcare practitioners for medical conditions not related to the patient's chronic illnesses. The clinic healthcare practitioner may wish to review these medications for possible adverse drug interactions with those drugs the healthcare practitioner has prescribed, for possible side effects, or for other medical reasons.

Selecting the animated "Exercise Log" icon 5136 of FIG. 51A for the diabetic patient automatically changes the information displayed to a patient exercise log, as described above and shown in FIG. 24. The healthcare practitioner may view comments that the patient may have entered into the exercise log using, for example, a data entry input box, that is displayed above the patient's Exercise Log 1910 or 1928 of FIG. 24.

Selecting the "Blood Pressure" icon 5138 of FIG. 51A for the diabetic patient, automatically changes the information displayed to a patient's Blood Pressure Log 2010, as described above and shown in FIG. 25. The healthcare practitioner may view comments that the patient may have entered into the blood pressure log using, for example, a data entry input box, that is displayed above the patient's Blood Pressure Log 2010 of FIG. 25.

Selecting the "Data Summary and Healthcare practitioner Comments" icon 5139 shown in FIG. 51A for any data screen of the diabetic clinic portion of the clinic system 200 automatically changes the information displayed to a table 5610, as shown in FIG. 56, corresponding to the patient's tabular summary 2610 of the blood glucose values for a range of dates, as described above and shown in FIG. 26. The clinic healthcare practitioner may enter comments into the "Healthcare practitioner Comments" column of the table 5610 by, for example, a data input entry box 5650, via the keyboard of the healthcare practitioner data terminal 130, as shown in FIG. 56. In various exemplary embodiments, if a healthcare practitioner writes a comment to the patient in the table 5610, then the record appears with a yellow background in the healthcare practitioner's view until the patient views the comment. Such communication between the healthcare practitioner and patient enhances the patient's compliance in the monitoring program and reflects the type of communication between healthcare practitioner and patient that would occur during an actual clinic visit.

The healthcare practitioner may also review the data presented in the table 5610 of FIG. 56 that corresponds to the data of the patient's blood sugar log 1510 of FIG. 15, by selecting the data presentation icons 5620-5626 above the table 5610.

The "Line Chart" icon 5620 allows the blood sugar log data to be presented as a linear graph; the "Histograms" icon 5622 as histograms; the "Pie Chart" icon 5624 as a pie chart; and the "Multiple pie charts" icon 5626 as multiple pie charts, as described above and shown in FIGS. 17-20

Selecting the healthcare practitioner "Message List" icon 5140 of FIG. 51A changes the display to the healthcare practitioner message list screen 7100 as shown in FIG. 71. The healthcare practitioner is presented with a list of messages sent by the healthcare practitioner's patients or by the healthcare practitioner, as shown in FIG. 71. Information, such as the date a message was sent, to whom the message was sent, who sent the message, and the subject/title of the message may be presented. However, if the healthcare practitioner has selected a particular patient to review that patient's records using one of the list boxes 5020-5024, only those messages concerning that particular patient are presented in a patient-specific healthcare message list screen 7100, as shown in FIG. 73. Additionally, in various exemplary embodiments, to distinguish unread from read messages, the unread messages in the list can be preceded by an asterisk, which can be color coded to increase its visibility.

Figure 72:
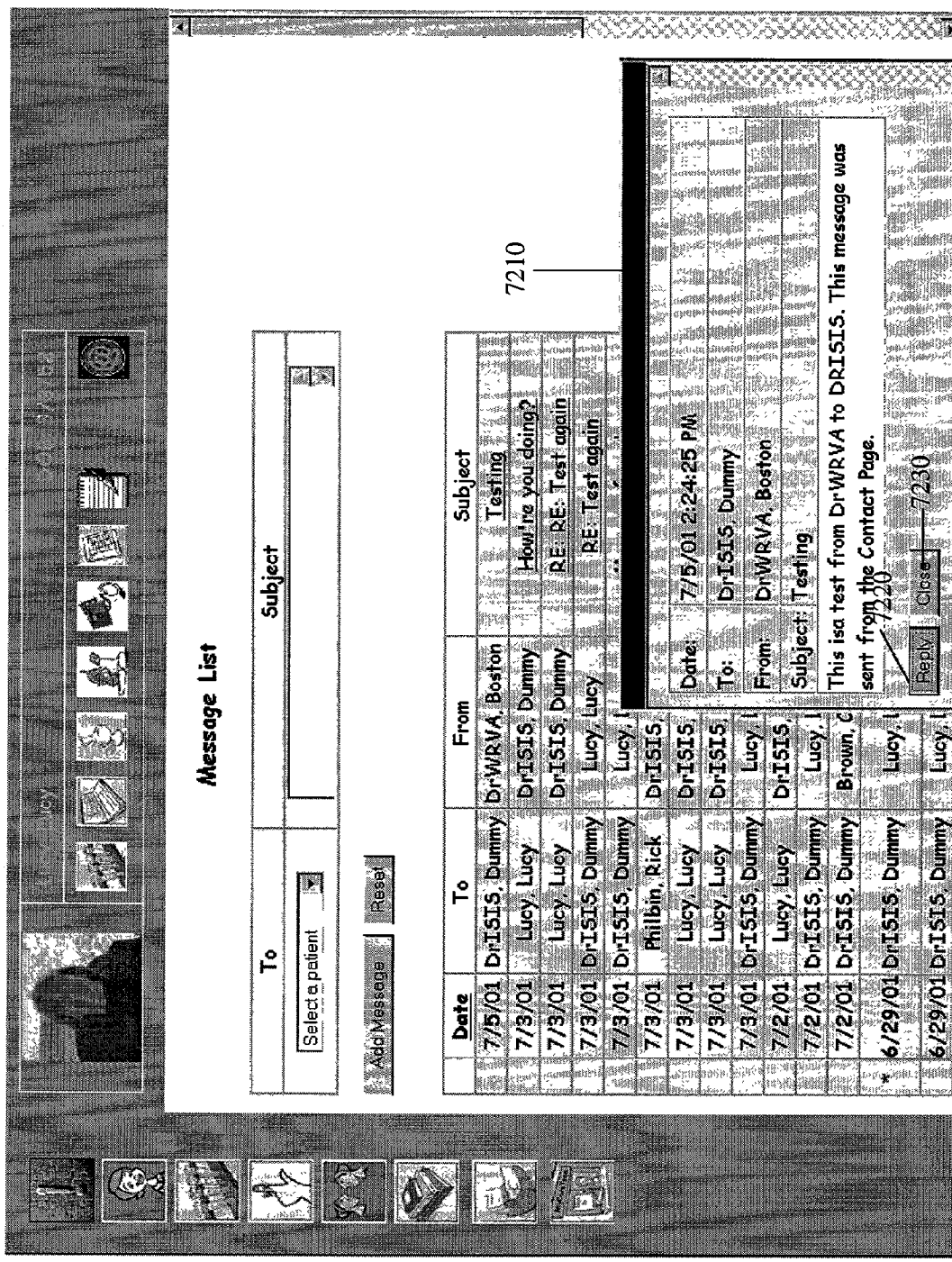
FIG. 72 shows one exemplary embodiment of a healthcare practitioner message list window of a graphical user interface according to this invention.

When the healthcare practitioner selects one of the underlined subject/titles, the clinical management system retrieves the selected message for the healthcare practitioner, as shown in FIG. 72. A message screen 7210 appears with information such as the date the message was sent, to whom the message is addressed, who sent the message, the subject/title of the message and the message itself. If the entire message does not fit within the message screen 7210, horizontal and/or vertical scroll bars are presented for the healthcare practitioner to scroll through the message (not shown). At the end of the message there is a "Reply" button 7220 and a "Close" button 7230. When selected, the "Reply" button 7220 allows the healthcare practitioner to send a response message to whomever sent the message. The "Close" button 7230 allows the healthcare practitioner to exit the message list screen 7210 and return the healthcare practitioner to the healthcare practitioner message list screen 7100 of FIG. 73

Figure 74:
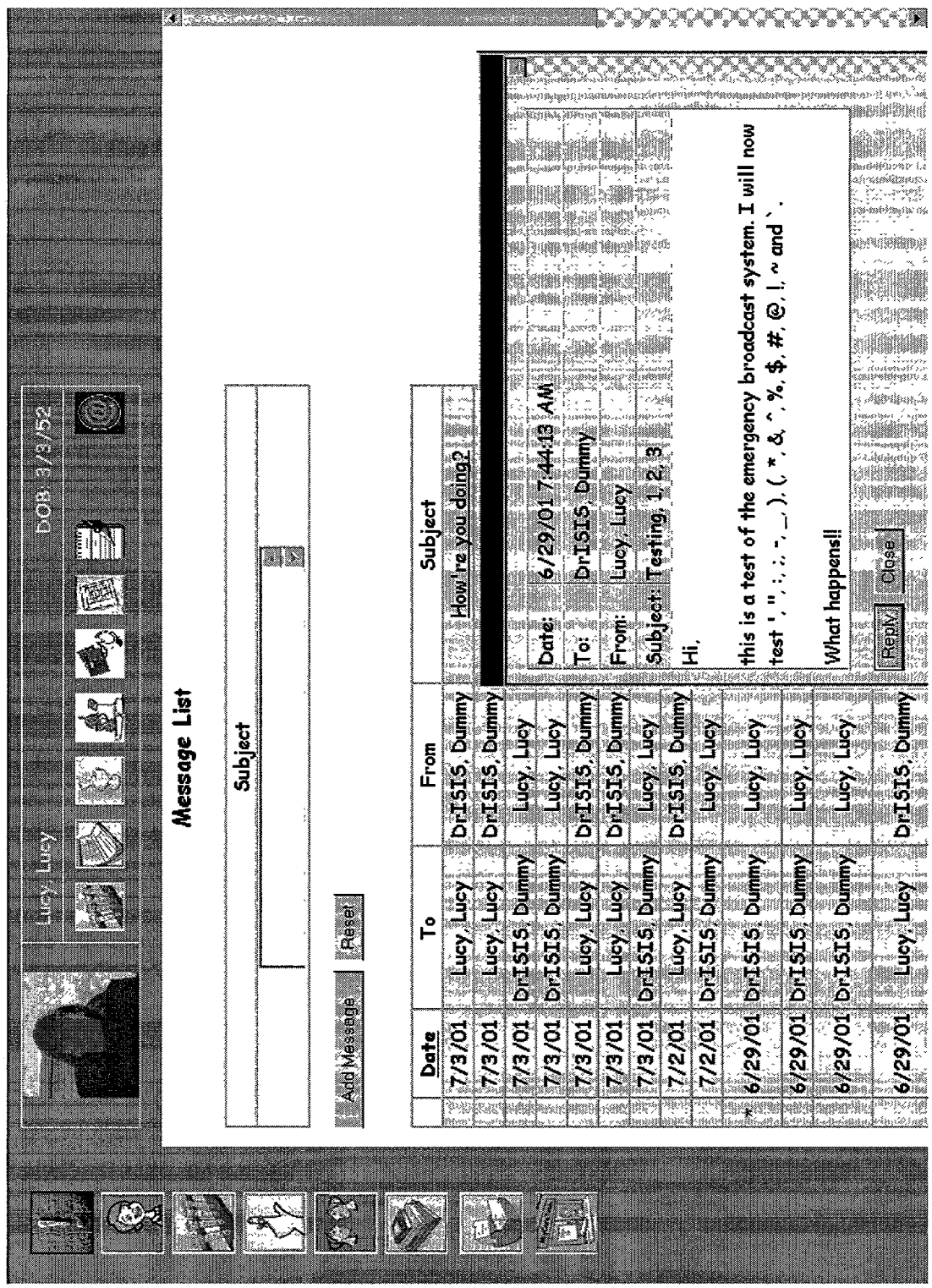
FIG. 74 shows one exemplary embodiment of a healthcare practitioner message list window of a graphical user interface according to this invention after a patient has been selected by a healthcare practitioner.

The healthcare practitioner may also create and add a new message using the healthcare practitioner message list screen 7100. The healthcare practitioner can use this screen to create a message directed to any patient that is assigned to that healthcare practitioner. The healthcare practitioner selects a "Select a Patient" drop down list box 7110. The "Select a Patient" drop down list box 7110 provides a lists of the patients in the clinical management system for chronic diseases 100 assigned to that healthcare practitioner. The healthcare practitioner then selects the patient that the healthcare practitioner wishes to address the message to using the list box 7110. However, if the healthcare practitioner has already selected a particular patient using one of the list boxes 5020-5024, the message is automatically addressed to that patient and the patient-specific healthcare practitioner message list screen 7100 is displayed, as shown in FIG. 73. The healthcare practitioner does not need to provide this information. Accordingly, the "Select a Patient" drop down list box 7110 does not need to be shown in the patient-specific healthcare practitioner message list screen 7100 shown in FIGS. 73 and 74. The healthcare practitioner may also provide a subject/title for the message, but this is not required. The healthcare practitioner does this by simply typing in the subject/title in the "Subject" data entry box 7120.

If the healthcare practitioner decides to discard the message, has made an error, or wants to change to whom the message is addressed to and/or the subject/title of the message, the healthcare practitioner can select the "Reset" button 7130. When selected, the "Reset" button 7130 clears to whom the message is addressed to as selected from the "Select a Patient" drop down list box 7110 and clears the "Subject" data entry box 7120. The function of the "Reset" button 7130 can also be accomplished by selecting a different individual from the "Select a Patient" drop down list box 7110 for whom the message is addressed and by backspacing over the incorrect data entry and then typing the correct data in the "Subject" data entry box 7120.

After the healthcare practitioner has selected the patient to address the message and typed a subject/title for the message (optional), the healthcare practitioner selects the "Add Message" button 7140. When the healthcare practitioner selects the "Add Message" button 7140, the display changes to the "Add a Message" screen, which is similar to that shown in FIG. 70. The healthcare practitioner's "Add a Message" screen displays the healthcare practitioner's name as who the message is from, the name of the patient to whom the message is addressed and the subject/title, if provided by the healthcare practitioner. Additionally, there is a message data entry box 7010, a "Submit" button 7020, a "Reset" button 7030, and a "Cancel" button 7040. The healthcare practitioner then enters his or her message into the message data entry box 7010 by using the keyboard or some other data entry device. Once finished, the healthcare practitioner selects the "Submit" button 7020 to send the message. If the healthcare practitioner is unsatisfied with the inputted message and wishes to discard all of its contents, the healthcare practitioner simply selects the "Reset" button 7030 or backspaces over the undesired portions of the message. However, if the healthcare practitioner wishes to disregard sending a message all together, the healthcare practitioner can select the "Cancel" button 7040. This returns the healthcare practitioner to the healthcare practitioner message list screen 7100 shown in FIGS. 71-74.

Figure 58:
FIG. 58 shows one exemplary embodiment of a screen of a graphical user interface usable to submit practitioner registration information.

Selecting the "register patients or practitioners" icon 5033 of FIG. 50 of the main practitioner data screen automatically changes the display to that shown in FIG. 57. When the healthcare practitioner selects the underlined "Practitioners" 5710 of FIG. 57, the display automatically changes to a "Practitioner Registration" form, as shown in FIG. 58. The "Practitioner Registration" form 5800 may include data entry input boxes 5810 for the entry of, for example, enrollment date, last name, first name, address, city, state, zip code, home and cell phones, pager, and e-mail or message address. The "Practitioner Registration" form 5800 may also include drop down list boxes 5820 for the entry of, for example, the healthcare practitioner's specialty and the occupation of the healthcare practitioner, for example, healthcare practitioner, nurse, etc. The specialty and the occupation of the healthcare practitioner dictate which patients they will interact with through the system and their permissions, for example, viewing types of patient data, and privileges, for example, entering new prescriptions for medications, on the system.

Figure 59:
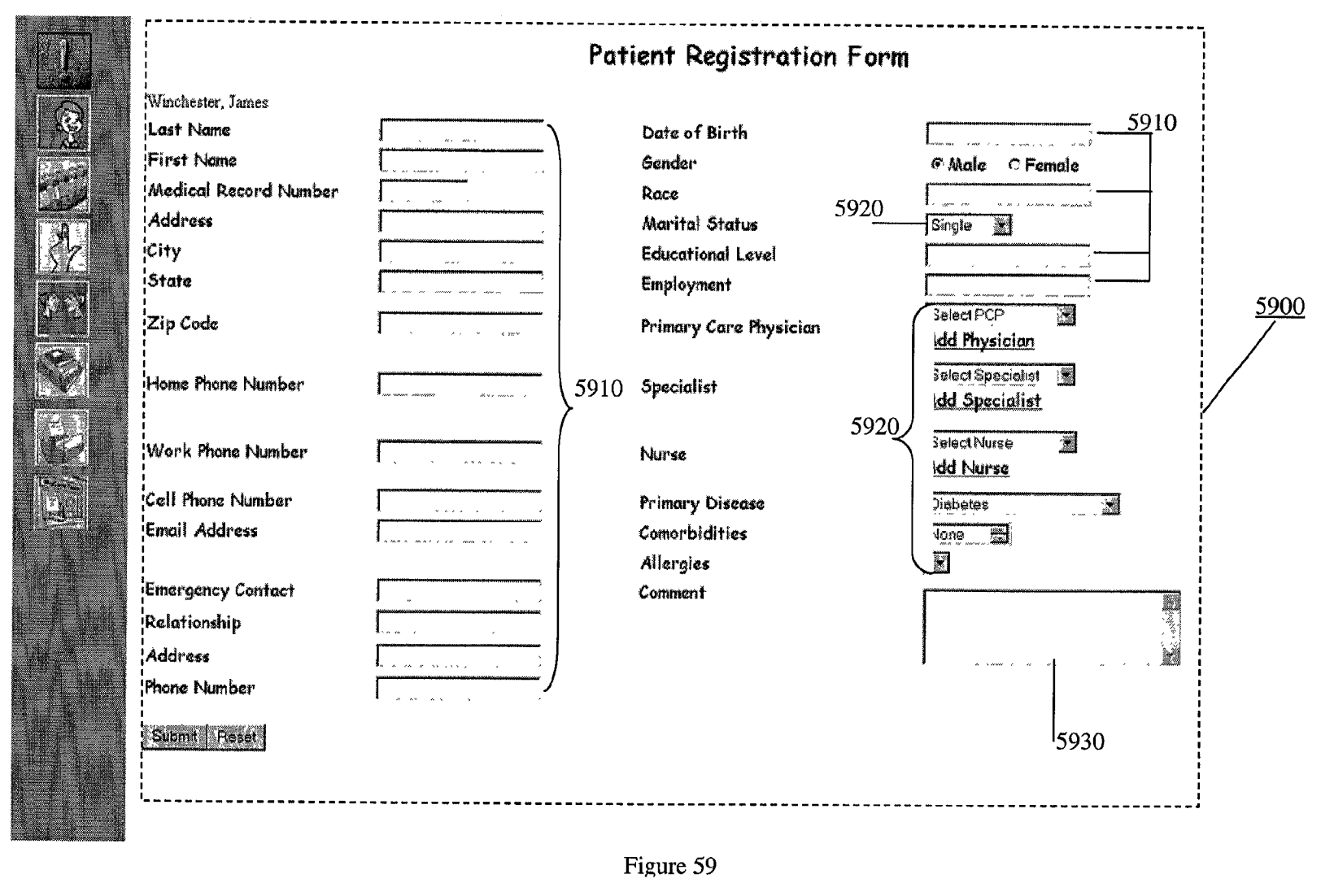

When the healthcare practitioner selects the underlined "Patients" icon 5720 shown in FIG. 57, the display automatically changes to a "Patient Registration Form", as shown in FIG. 59. The "Patient Registration Form" 5900 may include data entry input boxes 5910 for the entry of, for example, last name, first name, medical record number, address, city, state, zip code, home phone number, work phone number, cell phone number, e-mail or message address, emergency contact, relationship, address, phone number, date of birth, race, gender, educational level, and employment. The "Patient Registration Form" 5900 may also include drop down list boxes 5920 for the entry of, for example, marital status, primary care healthcare practitioner, specialist, nurse, primary disease, comorbidities, and allergies. Selecting the underlined phrases of "AddPhysician", "AddSpecialist", and "AddNurse" may allow these healthcare practitioners to be added to their respective drop down list boxes 5920 for entry into the "Patient Registration Form" 5900. A dialogue box 5930 may also be available to add comments. Selection of a specialist dictates which healthcare practitioner and associated healthcare practitioners are responsible for the patient's care.

Figure 60:
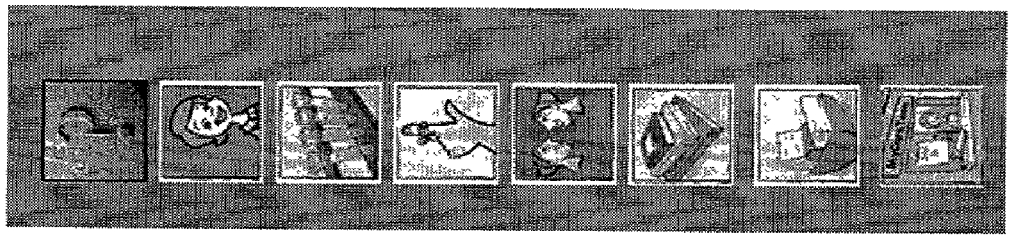
Figure 61:
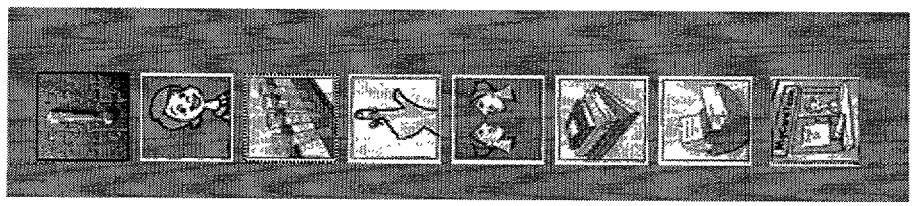

Selecting the "enter patient's lab results" icon 5034 of FIG. 50 of the main practitioner data screen 5000 automatically changes the display to that shown in FIG. 60 for diabetic patients, and to that shown in FIG. 61 for kidney disease patients. The "Lab Values Entry for Diabetes Patients" screen 6000 shown in FIG. 60 may include, for example, drop down list boxes 6010, usable to enter the date for which the lab values are being entered, and usable to select the patient whose lab values are being entered. Additionally, the "Lab Values Entry for Diabetes Patients" display 6000 may include, for example, data entry input boxes 6020, for the entry of lab values, such as, HbA1C, cholesterol, HDL, LDL, triglyceride and urine microalbumin, as described above in relation to the patient's "Lab Results" table 2110 shown in FIG. 21.

In the "Lab Values Entry for Dialysis Patients" screen 6100 shown in FIG. 61, the healthcare practitioner may also enter the date for which the lab values are being entered using, for example, drop down list boxes 6110, and may select the patient whose lab values are being entered using, for example, a drop down list box 6120. Additionally, a first option button 6130 indicates that no hospitalization is required for the test and a second option button 6134 indicates that hospitalization is required for the test. After selecting the "Go" button 6138, the screen changes to display the continued "Lab Values Entry for Dialysis Patients" screen 6200.

As shown in FIG. 62, the "Lab Values Entry for Dialysis Patients" screen 6200 shows, for example, multiple data entry input boxes 6210, by which laboratory test results may be entered by the healthcare practitioner. The entered laboratory test results may include but are not limited to, for example, Kt/V, albumin, calcium, creatinine, ferritin, glucose, HGB×3, iron, phosphate, potassium, PTH, TIBC, TSH, T3 uptake, T4 total, T7/FTI, cholesterol, HDL, LDL, triglycerides, HBSAG, HBSAB, HEPCAB, and HgbA1C. The entered laboratory results are then displayed to the kidney disease patient in the "Lab Results" table 3610, discussed above and shown in FIG. 36.

Figure 63:
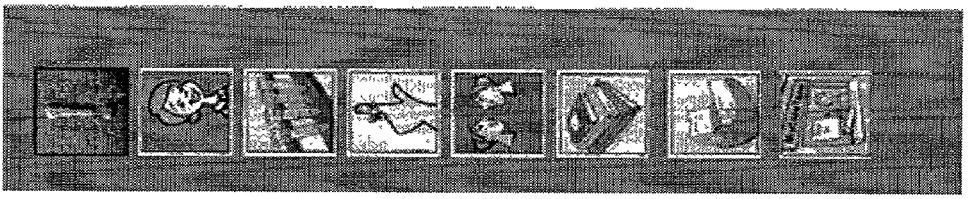

Selecting the "patient reminders" icon 5035 of FIG. 50 of the main practitioner data screen 5000 automatically changes to that shown in FIG. 63 for diabetic patients, and to that shown in FIG. 64 for kidney disease patients.

The "Patient Reminders" screen 6300 shown in FIG. 63 for the diabetic patient may include the current date and data which is to be entered by the healthcare practitioner including, but not limited to, for example, the selected patient, the date of the patient's visit and when the next visit is scheduled, the date of requested lab work and when the next lab work is scheduled, the date of requested HbA1C test values and when the next HbA1C test is scheduled, the date of a foot exam and the next scheduled foot exam, the date of an eye exam and the next scheduled eye exam. Selecting the patient and entering scheduled dates for visits, tests and exams may be facilitated by, for example, drop down list boxes 6310 that provide selections for the month, date and year, as shown in FIG. 63. Selecting the next scheduled date for visits, tests and exams may be facilitated by, for example, option buttons 6340 or data entry input boxes 6320, as also shown in FIG. 63. The entered patient reminders are displayed to the patient in the main patient data screen for diabetic patients 700, as described above and shown in FIG. 10.

Figure 65:
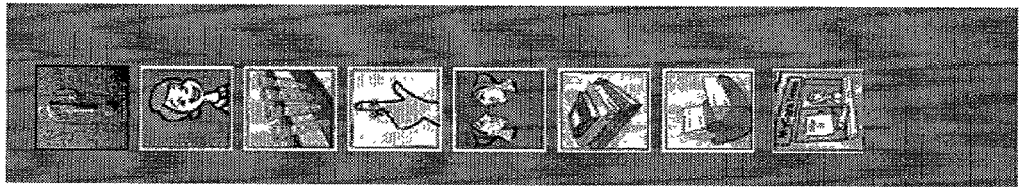

The "Patient Reminders" screen 6400 shown in FIG. 64 for the kidney disease patient may include the current date and, for example, a drop down list box 6410 for selecting the patient to whom the reminder is to be addressed. After selecting a patient, the main practitioner data screen changes to that shown in FIG. 65. The continued "Patient Reminders" screen 6500 shown in FIG. 65 may include the current date and the selected patient's name, and a number of, for example, drop down list boxes 6510, that facilitate entries of month, date and year for various reminders. The reminder dates that are entered for the kidney disease patient may include, but are not limited to a clinic visit, Kt/V test, lab work, chest X-ray, EKG, PPD/TB risk appraisal, a home visit, gynecology/mammogram exam, patient continuing education, medical history and physical, nursing assessment, long term care plan/conference, short term care plan/conference, and transfer set change. The entered patient reminders are displayed to the patient in the main patient data screen 3200 for kidney disease patients, as described above but not shown in FIG. 32.

Selecting the "On-line chatroom" icon 5036 of FIG. 50 of the main practitioner data screen 5000 automatically changes the screen to that of a message dialogue box (not shown) including the e-mail or message address of the patient support group for the particular chronic illness that the healthcare practitioner is managing. The healthcare practitioner may then interact with the patient support group, offering suggestions for daily living, explaining medical procedures, correcting misunderstandings, etc.

Figure 66:
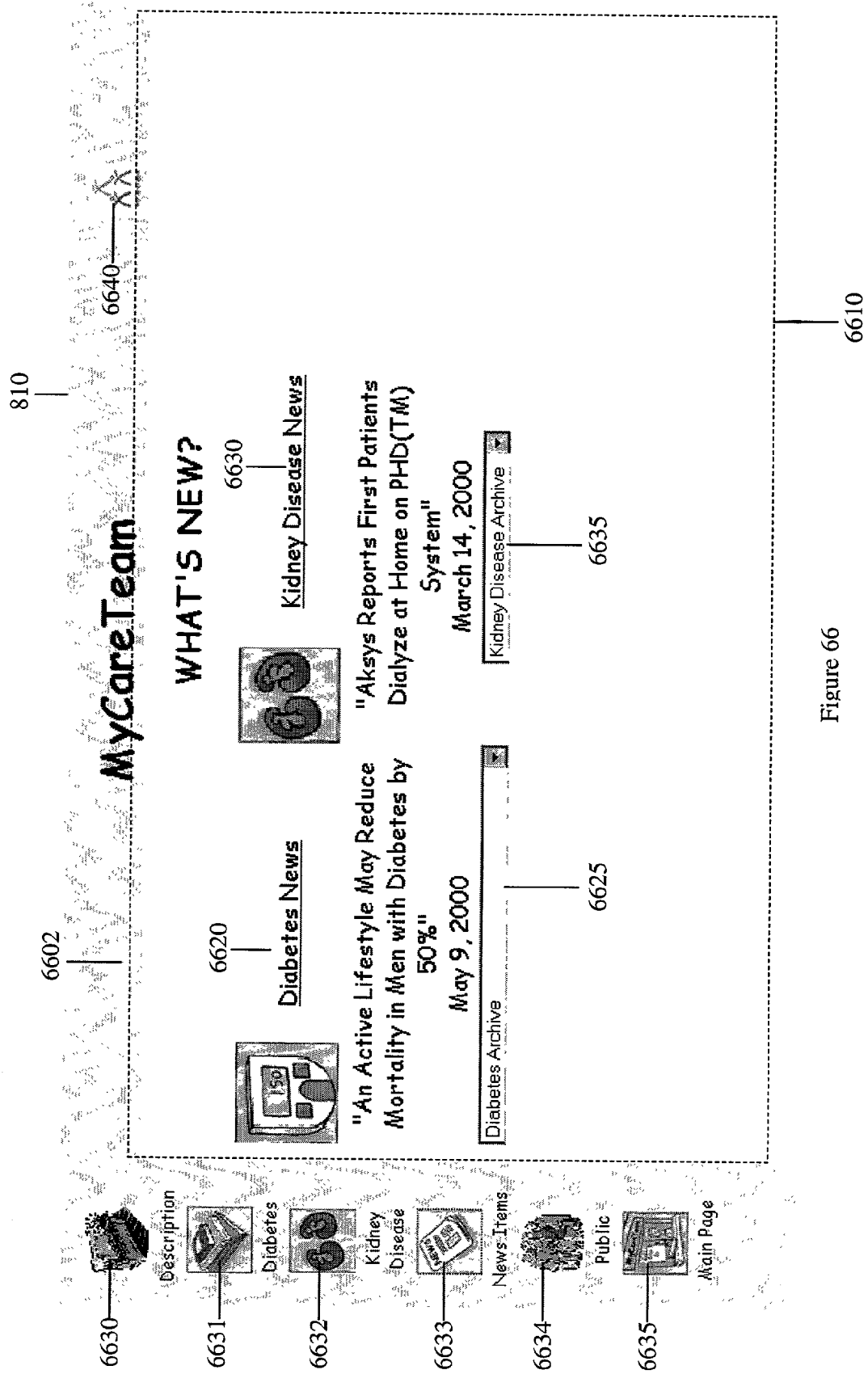
FIG. 66 shows one exemplary embodiment of a main visitor data screen of a graphical user interface according to this invention.
Figure 67A:
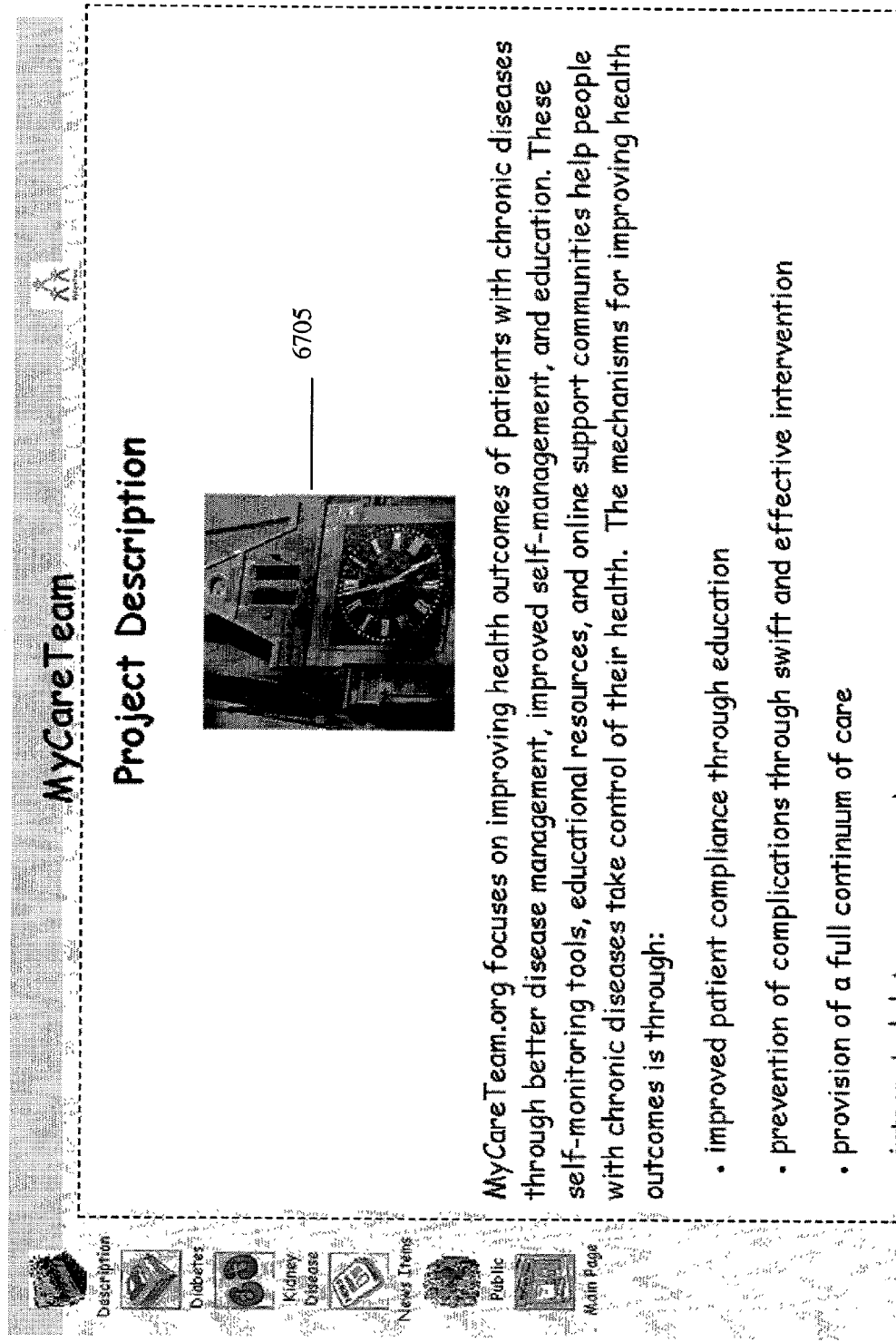
Figure 67F:
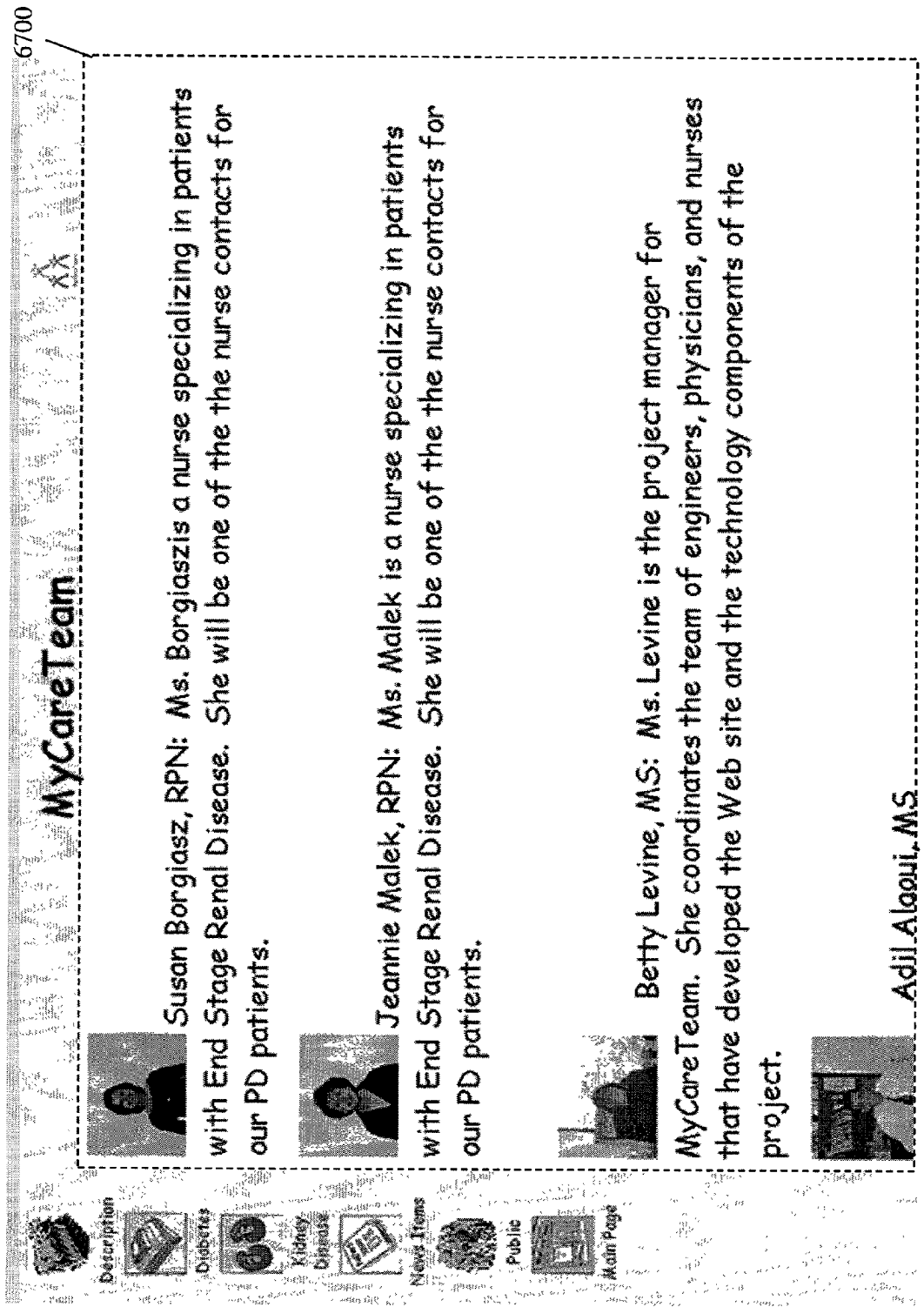
Figure 67G:

When a visitor logs on to the system, he or she may enter the clinic lobby 400 of FIG. 4 and proceed to open the door icon 404 of the public library, as shown in FIG. 5. Selecting the door icon 404 changes the screen to that of the main visitor data screen 6600, as shown in FIG. 66. The main visitor data screen 6600 includes, for example, a frame 6602 along its upper and left-side borders that has a light green background 810 and a central display area 6610.

The upper border of the frame 6602 may include the name of the project and an icon 6640 that, when selected, connects the visitor to another screen (not shown) that is accessible to visitors. The left side of the border of the frame 6602 may include, for example, icons for "Description" 6630, "Diabetes" 6631, "Kidney Disease" 6632, "News Items" 6633, "Public" 6634, and "Main Page" 6635. The central display area 6610 may include the latest news items concerning the chronic illnesses that the clinic manages. For example, if the underlined "DiabetesNews" 6620 is selected, the screen will change to display the latest diabetes news in the central display area 6610, corresponding to that news displayed in the patient's education site, as shown in FIG. 13. The visitor may also select archival news by selecting the archival article from, for example, a drop down list box 6625, labeled "Diabetes Archive". The visitor may similarly access the latest news item and archival news items by selecting the underlined "KidneyDiseaseNews" 6630 or the drop down list box 6635, labeled "Kidney Disease Archive".

Selecting the "Description" icon 6630 of FIG. 66 changes the screen to display a project description screen 6700, as shown in FIGS. 67A-67G. The project description may include multiple pictures 6705 which are sequentially displayed while the project description is displayed. The project description may also include links to other sites within the clinic system 200, Internet sites or World Wide Web sites for further description of the project.

Selecting the "Diabetes" icon 6631 of FIG. 66 changes the screen to display the diabetes education site, as described above and shown in FIG. 29

Selecting the "Kidney Disease" icon 6632 of FIG. 66 changes the screen to display the PD education information, as described above and shown in FIG. 38.

Selecting the "News Item" icon 6633 changes the screen to display the main visitor data screen 6600 of FIG. 66.

By selecting the "Main Page" icon 6635 of FIG. 66, the visitor returns to the clinic lobby 400 of FIG. 4.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and the scope of the invention.

What is claimed is:

1. A computerized method for managing chronic illnesses, comprising:
   outputting a first set of at least one graphical user interface screen usable by a user who has at least one chronic illness and by others including at least one healthcare practitioner to input or review user-provided information;
   wherein the user-provided information includes (i) clinical data obtained from the user usable to manage the at least one chronic illness, and (ii) comments describing contemporaneous activities of the user;
   automatically analyzing the clinical data to determine an alert value;
   outputting a second set of at least one graphical user interface screen usable by the user and the others to access management information usable to manage the at least one chronic illness, at least some of the management information being derived from the user-provided information;
   outputting a third set of at least one graphical user interface screen usable by the others to review the user-provided information obtained from the user and the derived management information; and
   receiving additional management information from the at least one healthcare practitioner for inclusion in the management information,
   wherein the user and the others remotely and asynchronously interact to manage on a near-daily basis the at least one chronic illness.

2. The method of claim 1, further comprising:
   outputting a fourth set of at least one graphical user interface screen that graphically depicts a clinic that the user would visit to manage, supply or review the management information and the clinical data for the at least one chronic illness, the first set of at least one graphical user interface screen simulating an interaction of the user with the clinic, and wherein the first and second sets of at least one graphical user interface screens are accessible through the third set of at least one graphical user interface screen.

3. The method of claim 1, wherein providing the third set of at least one graphical user interface screen includes providing a user interface screen to solicit a selection from the at least one healthcare practitioner to view at least one of the following lists: a first list of patients with alert value based on their respective clinical data, a second list of patients with new data, and a third list listing all patients.

4. The method of claim 3, wherein providing the third set of at least one graphical user interface screen includes providing a user interface for the at least one healthcare practitioner to view information related to a patient based on the selection.

5. The method of claim 4, wherein the information is related to an alert if the patient is on the first list.

6. The method of claim 4, wherein the information is related to the new data if the patient is on the second list.

7. The method of claim 4, wherein the information is related to at least one of the following if the patient is on the third list: lab results information of the patient, blood glucose information of the patient, medication information related to medications taken by or prescribed to the patient, blood pressure information of the patient, and exercise information of the patient.

8. The method of claim 7, wherein providing the third set of at least one graphical user interface screen includes providing a user interface for the at least one healthcare practitioner to modify the medication information.

9. The method of claim 1, wherein providing the third set of at least one graphical user interface screen includes providing a user interface for the at least one healthcare practitioner to access a summary of data for the user for the at least one chronic illness.

10. The method of claim 9, wherein providing the third set of at least one graphical user interface screen includes providing a user interface for the at least one healthcare practitioner to provide comments to the user.

11. The method of claim 10, further comprising providing a user interface for the user to access the comments provided by the at least one healthcare practitioner.

12. The method of claim 11, wherein providing the user interface for the at least one healthcare practitioner to access a summary of data for the user for the at least one chronic illness includes indicating a status of whether the comments have been accessed by the user.

13. The method of claim 1, further comprising providing a user interface for the user to send messages to or receive messages from the at least one healthcare practitioner.

14. The method of claim 1, further comprising providing a user interface for the at least one healthcare practitioner to send messages to or receive messages from the user.

15. The method of claim 14, wherein providing the user interface for the at least one healthcare practitioner to send messages to or receive messages from the user includes providing the user interface when the at least one healthcare practitioner logs into a management system.

16. The method of claim 15, wherein providing the third set of at least one graphical user interface screen usable by the at least one healthcare practitioner to review the clinical data includes providing an icon for linking to the user interface for the at least one healthcare practitioner to send messages to or receive messages from the user.

17. The method of claim 1, wherein providing the third set of at least one graphical user interface screen includes allowing the at least one healthcare practitioner to review messages sent to or received from the user when reviewing the clinical data associated with the user.

18. The method of claim 1, further comprising providing a user interface for the at least one healthcare practitioner to send messages to or receive messages from other healthcare practitioners.

19. The method of claim 1, further comprising providing a user interface for the at least one healthcare practitioner to track information associated with the user related to at least one of the following:
    past office visits;
    at least one upcoming office visit appointment;
    at least one upcoming examination appointment;
    at least one overdue office visit appointment; and
    at least one overdue examination appointment.

20. A graphical healthcare management system comprising:
    a first set of at least one graphical user interface screen usable by a user who has at least one chronic illness and others including at least one healthcare practitioner to input or review user-provided information stored in a database, the user-provided information including (i) clinical data obtained from the user usable to manage at least one of the user's chronic illnesses, and (ii) comments relating to contemporaneous personal activities of the user;
    a second set of at least one graphical user interface screen usable by the user and the others to access management information usable to manage the at least one chronic illness, at least some of the management information being derived from the clinical data and the comments describing contemporaneous activities of the user included in the user-provided information obtained from the user and stored in the database; and
    a third set of at least one graphical user interface screen usable by the at least one healthcare practitioner to review the user-provided information obtained from the user and the derived management information and to supply additional management information from the at least one healthcare practitioner to the database for inclusion in the management information,
    wherein the third set of at least one graphical user interface screen includes a user interface screen to solicit a selection from the at least one healthcare practitioner to view at least one of the following lists: a first list of patients with an alert value based on their respective clinical data, a second list of patients with new data, and a third list listing all patients, and
    wherein the user and the at least one healthcare practitioner remotely and asynchronously interact to manage on a near-daily basis the at least one chronic illness.

21. The graphical healthcare management system of claim 20, wherein the third set of at least one graphical user interface screen includes a user interface for the at least one healthcare practitioner to view the user-provided information related to a patient based on the selection.

22. The graphical healthcare management system of claim 21, wherein the user-provided information is related to the new data if the patient is on the second list.

23. The graphical healthcare management system of claim 21, wherein the user-provided information is related to at least one of the following if the patient is on the third list: lab results information of the patient, blood glucose information of the patient, medication information related to medications taken by or prescribed to the patient, blood pressure information of the patient, and exercise information of the patient.

24. The graphical healthcare management system of claim 23, wherein the third set of at least one graphical user interface screen includes a user interface for the at least one healthcare practitioner to modify the medication information.

25. The graphical healthcare management system of claim 21, wherein the user-provided information is related to the alert if the patient is on the first list.

26. The graphical healthcare management system of claim 20, wherein the third set of at least one graphical user interface screen includes a user interface for the at least one healthcare practitioner to access a summary of data for the user for at least one of the user's chronic illness.

27. The graphical healthcare management system of claim 26, wherein the third set of at least one graphical user interface screen includes a user interface for the at least one healthcare practitioner to provide comments to the user.

28. The graphical healthcare management system of claim 27, further includes a user interface for the user to access the comments provided by the at least one healthcare practitioner.

29. The graphical healthcare management system of claim 28, wherein the user interface for the at least one healthcare practitioner to access a summary of data for the user for at least one of the user's chronic illness indicates a status of whether the comments have been accessed by the user.

30. The graphical healthcare management system of claim 20, further comprising a user interface for the user to send messages to or receive messages from the at least one healthcare practitioner.

31. The graphical healthcare management system of claim 20, further comprising a user interface for the at least one healthcare practitioner to send messages to or receive messages from the user.

32. The graphical healthcare management system of claim 31, wherein the user interface for the at least one healthcare practitioner to send messages to or receive messages from the user is accessible by the at least one healthcare practitioner when the at least one healthcare practitioner logs into the management system.

33. The graphical healthcare management system of claim 31, wherein the third set of at least one graphical user interface screen usable by the at least one healthcare practitioner to review the clinical data includes an icon for linking to the user interface for the at least one healthcare practitioner to send messages to or receive messages from the user.

34. The graphical healthcare management system of claim 20, wherein the third set of at least one graphical user interface screen allows the at least one healthcare practitioner to review messages sent to or received from the user when reviewing the clinical data associated with the user.

35. The graphical healthcare management system of claim 20, further comprising a user interface for the at least one healthcare practitioner to send messages to or receive messages from other healthcare practitioners.

36. The graphical healthcare management system of claim 20, further comprising a user interface for the at least one healthcare practitioner to track user-provided information related to at least one of the following:

past office visits;
at least one upcoming office visit appointment;
at least one upcoming examination appointment;
at least one overdue office visit appointment; and
at least one overdue examination appointment.

* * * * *